US011484558B2

(12) United States Patent
Ehrlich et al.

(10) Patent No.: US 11,484,558 B2
(45) Date of Patent: Nov. 1, 2022

(54) EPIZOOTIC HEMORRHAGIC DISEASE VIRUS—TEL AVIV UNIVERSITY (EHDV-TAU)—ONCOLYTIC VIRUS FOR TREATING CANCER

(71) Applicant: Ramot at Tel-Aviv University Ltd., Tel Aviv (IL)

(72) Inventors: Marcelo Ehrlich, Tel Aviv (IL); Eran Bacharach, Tel Aviv (IL); Ben Shai, Tel Aviv (IL); Oded Danziger, Tel Aviv (IL)

(73) Assignee: RAMOT AT TEL-AVIV UNIVERSITY LTD, Tel Aviv (IL)

( * ) Notice: Subject to any disclaimer, the term of this patent is extended or adjusted under 35 U.S.C. 154(b) by 947 days.

(21) Appl. No.: 16/018,601

(22) Filed: Jun. 26, 2018

(65) Prior Publication Data

US 2018/0369302 A1 Dec. 27, 2018

Related U.S. Application Data

(60) Provisional application No. 62/525,289, filed on Jun. 27, 2017.

(51) Int. Cl.

| | |
|---|---|
| ***A61K 35/765*** | (2015.01) |
| ***A61P 35/00*** | (2006.01) |
| ***A61K 45/06*** | (2006.01) |
| ***C12N 7/00*** | (2006.01) |

(52) U.S. Cl.
CPC ............ *A61K 35/765* (2013.01); *A61K 45/06* (2013.01); *A61P 35/00* (2018.01); *C12N 7/00* (2013.01); *C12N 2720/12121* (2013.01); *C12N 2720/12132* (2013.01); *C12N 2720/12151* (2013.01); *C12N 2720/12171* (2013.01)

(58) Field of Classification Search
CPC ....... A61K 35/765; A61K 45/06; A61P 35/00; C12N 7/00; C12N 2720/12121
See application file for complete search history.

(56) References Cited

PUBLICATIONS

Shai et al., "Epizootic Hemorrhagic Disease Virus Induces and Benefits from Cell Stress, Autophagy, and Apoptosis", 2013, Journal of Virology 87(24), p. 13397-13408.*
Danzinger et al., "Combined genetic and epigenetic interferences with interferon signaling expose prostate cancer cells to viral infection", Oncotarget 2(32), p. 52115-52134.*
Dellac et al., Int. J. Cancer, 2021, 148: 2321-2334.*
Hu et al., Acta Oncologica, 2008, 47: 124-134.*
Russell et al., PNAS, 2008, 105: 4370-4375.*
Koudelka et al., Current Opinion in Chemical Biology, 2010, 14: 810-817.*
Meulenbroek et al., Mol. Ther., 2004, 9: 618-624.*
"Combined genetic and epigenetic interferences with interferon signaling expose prostate cancer cells to viral infection" Oded Danziger et al.Department of Cell Research and Immunology, George S. Wise Faculty of Life Sciences, Tel Aviv University, Tel Aviv, Israel Published: Oncotarget, Advance Publications, Jun. 28, 2016 (20 pages).

* cited by examiner

*Primary Examiner* — Ileana Popa
(74) *Attorney, Agent, or Firm* — Wenderoth, Lind & Ponack, L.L.P.

(57) ABSTRACT

The present invention relates to a unique oncolytic virus, Epizootic Hemorrhagic Disease virus-Tel Aviv University (EHDV-TAU), and to methods and pharmaceutical compositions comprising thereof for preventing or treating cancer exhibiting an alteration in interferon signaling and/or the innate immune antiviral response.

10 Claims, 31 Drawing Sheets

Specification includes a Sequence Listing.

| EHDV-TAU | - | + | + | + | - | - |
|---|---|---|---|---|---|---|
| Q-VD-OPH | - | - | + | - | - | + |
| Necrostatin-1 | - | - | - | + | - | - |
| STS (20h) | - | - | - | - | + | + |

| | LNCaP | LNCaP-JAK1 | | LNCaP-JAK1 +EHDV-TAU | | |
|---|---|---|---|---|---|---|
| IL-6 | + | + | - | - | - | + |
| IFNα | - | - | + | - | + | - |
| IFIT2 | 0.0 | 1.1 | 1.0 | 0.0 | 2.4 | 3.4 |
| IFIT1 | 0.0 | 0.7 | 1.9 | 0.0 | 2.4 | 3.0 |
| GBP2 | 0.2 | 2.0 | 0.4 | 0.0 | 0.3 | 2.8 |
| APOL2 | 0.8 | 1.0 | 0.0 | -0.4 | 1.5 | 2.7 |
| IFIT3 | 0.0 | 1.0 | 1.8 | 0.0 | 2.6 | 2.6 |
| B2M | 0.2 | 0.3 | 0.5 | -0.4 | 1.5 | 2.6 |
| ISG20 | 0.0 | 1.5 | 0.2 | 0.0 | 3.4 | 2.5 |
| LGMN | 0.1 | 1.3 | 0.2 | -0.7 | 0.6 | 2.4 |
| OAS1 | 0.0 | 0.1 | 1.5 | 1.2 | 0.5 | 2.3 |
| DTX3L | 0.7 | 0.4 | 0.7 | 0.1 | 1.6 | 2.2 |
| HLA-B | 0.0 | 0.2 | 0.6 | -0.3 | 1.3 | 1.9 |
| AHNAK2 | 0.0 | 0.3 | -0.1 | 0.0 | 0.0 | 1.8 |
| HLA-C | 0.0 | 0.3 | 1.0 | 0.1 | 1.2 | 1.6 |
| HK2 | 0.3 | 0.6 | -0.3 | 0.4 | 0.0 | 1.5 |
| DDX58 | 0.0 | 0.4 | 0.3 | 0.0 | 1.5 | 1.5 |
| ISG15 | 0.1 | 0.1 | 1.7 | 0.3 | 3.6 | 1.3 |
| STAT3 | 0.6 | 0.7 | 0.1 | -0.3 | 0.6 | 1.3 |
| STAT1 | 0.4 | 0.1 | 1.2 | 0.2 | 2.6 | 1.2 |
| IFIT5 | 0.0 | 0.0 | 1.2 | 0.2 | 2.4 | 1.0 |
| SAMHD1 | -0.5 | 0.4 | 0.7 | 0.0 | 1.7 | 0.9 |
| SLC16A1 | 0.0 | 0.5 | 0.2 | 0.1 | 0.1 | 0.9 |
| SP100 | 0.0 | 0.1 | 0.0 | 0.0 | 1.6 | 0.8 |
| EIF2AK2 | 0.2 | 0.2 | 0.0 | 0.0 | 1.5 | 0.7 |
| GLRX | 0.0 | 0.1 | 0.5 | -0.5 | 0.7 | 0.7 |
| OGFR | -0.3 | 0.2 | 0.5 | -0.6 | 0.1 | 0.6 |
| IRF6 | -0.3 | -0.1 | 0.2 | -0.1 | 0.4 | 0.6 |
| STAT2 | 0.0 | 0.4 | 1.1 | 0.0 | 2.4 | 0.5 |
| TRAFD1 | 0.0 | 1.2 | 0.0 | 0.0 | 1.4 | 0.4 |
| CHMP5 | 0.2 | -0.6 | 0.4 | 0.2 | 0.3 | 0.2 |
| ADAR | 0.1 | -0.1 | 0.2 | 0.1 | 0.5 | 0.2 |
| TRIM25 | 0.0 | 0.1 | 0.3 | 0.1 | 1.0 | 0.2 |
| PNPT1 | -0.1 | 0.0 | 0.3 | -0.2 | 0.6 | 0.2 |
| LAP3 | 0.0 | 0.0 | 0.3 | 0.0 | 1.0 | 0.2 |
| WARS | 0.1 | 0.9 | 0.0 | 0.1 | 1.1 | 0.1 |
| IFIH1 | 0.0 | 0.6 | 0.8 | 0.0 | 2.8 | 0.0 |
| NUB1 | -0.2 | 1.0 | 0.0 | 0.0 | 1.3 | 0.0 |
| TAP1 | 0.0 | 0.4 | 0.2 | 0.0 | 1.4 | 0.0 |
| DDX60 | 0.0 | 0.2 | 0.0 | 0.0 | 2.3 | 0.0 |
| OAS3 | 0.1 | 0.0 | 0.4 | 0.0 | 2.3 | 0.0 |
| GBP1 | 0.0 | 0.0 | 0.0 | 0.0 | 1.2 | 0.0 |
| BST2 | 0.0 | 0.0 | -0.1 | 0.0 | 0.6 | 0.0 |
| GBP4 | 0.0 | 0.0 | 0.0 | 0.0 | 0.8 | 0.0 |
| OASL | 0.0 | 0.1 | 0.5 | 0.0 | 0.6 | 0.0 |
| OAS2 | 0.0 | 0.0 | 0.0 | 0.0 | 2.7 | 0.0 |
| APOL1 | 0.0 | 1.3 | 0.0 | 0.0 | 0.3 | 0.0 |
| PLSCR1 | 0.0 | 1.6 | 0.0 | 0.0 | 0.0 | 0.0 |
| HLA-A | 0.0 | 0.5 | -0.1 | 0.6 | 1.0 | -0.3 |
| SCO2 | -0.8 | 0.0 | -0.3 | 0.2 | 0.0 | -0.2 |
| PRKCD | 0.0 | -0.2 | -0.1 | 0.1 | 0.0 | -0.6 |
| ARG2 | -0.2 | -0.1 | -0.1 | 0.1 | 0.0 | -1.2 |

| LNCaP-JAK1 +IFNγ | |
|---|---|
| ISG20 | 3.6 |
| IFIH1 | 3.1 |
| OAS3 | 3.0 |
| IFIT2 | 3.0 |
| ISG15 | 3.0 |
| GBP1 | 2.8 |
| IFIT3 | 2.7 |
| DDX60 | 2.6 |
| STAT1 | 2.6 |
| IFIT1 | 2.5 |
| IFIT5 | 2.3 |
| TRAFD1 | 2.3 |
| WARS | 2.3 |
| GBP4 | 2.2 |
| TAP1 | 2.2 |
| DDX58 | 2.2 |
| STAT2 | 2.1 |
| APOL2 | 2.1 |
| DTX3L | 1.8 |
| SAMHD1 | 1.8 |
| BST2 | 1.6 |
| STAT3 | 1.6 |
| SP100 | 1.5 |
| NUB1 | 1.5 |
| B2M | 1.5 |
| LGMN | 1.3 |
| APOL1 | 1.2 |
| EIF2AK2 | 1.1 |
| TRIM25 | 0.9 |
| HLA-C | 0.8 |
| HLA-B | 0.8 |
| LAP3 | 0.8 |
| GLRX | 0.8 |
| HLA-A | 0.6 |
| GBP2 | 0.6 |

EPIZOOTIC HEMORRHAGIC DISEASE VIRUS—TEL AVIV UNIVERSITY (EHDV-TAU)—ONCOLYTIC VIRUS FOR TREATING CANCER

FIELD OF THE INVENTION

The present invention relates to the fields of oncology and virology. More specifically, the invention relates to a unique oncolytic virus, and to methods and pharmaceutical compositions comprising thereof for treating cancer.

BACKGROUND OF THE INVENTION

Oncolytic viruses are viral strains that can infect and kill malignant cells without harming healthy cells. Oncolytic viruses can access cells through binding to receptors on their surface or through fusion with the plasma membrane, and establish a lytic cycle in tumors. Several viruses have been investigated in humans, and the first oncolytic virus approved for use in the United States and the European Union for patients with locally advanced or non-resectable melanoma is a genetically engineered Herpes Simplex Virus, named IMLYGIC™ (T-VEC/Talimogene Laherparepvec).

Cancer is driven by genetic and epigenetic alterations that allow cells to over-proliferate and escape mechanisms that normally control their survival and migration. Many of these alterations map to signaling pathways that control cell growth, division, and cell death, and can promote cancer progression, such as changes in the tumor microenvironment, angiogenesis, and inflammation.

For example, the Janus kinase/signal transducers and activators of transcription (JAK/STAT) pathway is the principal signaling mechanism for a wide array of cytokines and growth factors. JAK activation stimulates cell proliferation, differentiation, cell migration and apoptosis. In different cancers, JAK signaling plays a dual role, as exacerbated signaling is typical of certain types of leukemia, while many solid tumors, including prostate cancer (PCa), are characterized by defects in interferon-induced JAK/STAT signaling.

Therefore, it is an object of the invention to provide an oncolytic virus that selectively replicates in and kills cancer cells exhibiting any alteration in the interferon signaling and/or the innate immune antiviral response.

It is another object of the invention to provide methods for treating cancer using an oncolytic virus.

It is still another object of the invention to provide pharmaceutical compositions comprising an oncolytic virus for treating cancer.

Further purposes and advantages of this invention will appear as the description proceeds.

SUMMARY OF THE INVENTION

In one aspect, the present invention provides a method for preventing or treating cancer exhibiting an alteration in interferon signaling and/or the innate immune antiviral response, comprising administering an oncolytic Epizootic Hemorrhagic Disease virus-Tel Aviv University (EHDV-TAU) virus, or a pharmaceutical composition comprising thereof, to a subject.

In some embodiments, the cancer is selected from prostate cancer, melanoma, renal cancer, breast cancer, lung cancer, liver cancer, colorectal cancer, gastric cancer, pancreatic cancer, bladder cancer, glioblastoma, head and neck cancer, myeloma, lymphoma and leukemia.

In other embodiments of the invention, the EHDV-TAU or a pharmaceutical composition comprising thereof, is administered to the subject by a parenteral, intra-tumoral, intradermal, transdermal, intravenous, intramuscular, intranasal, subcutaneous, percutaneous, intratracheal, intraperitoneal, intravesical, inhalation, perfusion, lavage, or oral administration.

In further embodiments, the method of the invention further comprises administering to the subject a second cancer therapy. The second cancer therapy is selected from virotherapy with another virus, chemotherapy, radiotherapy, immunotherapy, biological therapy, anti-angiogenic therapy, hormone therapy, anti-vascular therapy, therapy with a cytostatic agent, therapy with an epigenetic modifying agent, cryotherapy, toxin therapy, surgery and a chemical modification of the interferon response.

In a specific embodiment of the method of the invention, the oncolytic EHDV-TAU virus is EHDV-TAU-LNCaP comprising the RNA sequence set forth in SEQ ID NO: 3.

In another specific embodiment, the sequence of the oncolytic EHDV-TAU virus comprises at least the following mutations compared to the sequence of Epizootic Hemorrhagic Disease Virus 2-Ibaraki (EHDV2-Ibaraki) of SEQ ID NO: 1:

(i) point mutations at T2666C, G3713A, G3888A, C3953T, A4893G, A7024G, A11751G, T16056C, G16094A, G18617A and G18920A of SEQ ID NO: 1;

(ii) deletion of CTACAC at positions 6984-6989, deletion of G at position 14526 and deletion of G at position 14618 of SEQ ID NO: 1;

(iii) insertion of G at position 14519 and insertion of G at position 14608 of SEQ ID NO: 1.

In another aspect, the present invention provides an oncolytic EHDV-TAU virus for preventing or treating cancer exhibiting an alteration in interferon signaling and/or the innate immune antiviral response.

In a specific embodiment, the oncolytic EHDV-TAU virus is EHDV-TAU-LNCaP comprising the RNA sequence as set forth in SEQ ID NO: 3.

In some embodiments, the oncolytic EHDV-TAU virus is obtained by a chemical modification, site-directed mutagenesis, in-vitro evolution of EHDV2-IBA. The site directed mutagenesis comprises addition of a fluorescent protein, arming of the virus with immune modifiers, or inactivation of viral proteins that mediate antagonism to anti-viral defenses. The chemical modification comprises fluorescent tagging and/or chemical conjugation of biochemically active molecules.

In a further aspect, the present invention provides a cell infected ex-vivo with the oncolytic EHDV-TAU virus of the invention, for preventing or treating cancer exhibiting an alteration in interferon signaling and/or the innate immune antiviral response, by administering the cell to a subject.

In a still further aspect, the present invention provides a pharmaceutical composition comprising an effective amount of the oncolytic EHDV-TAU virus of the invention and a pharmaceutically acceptable carrier or vehicle, for preventing or treating cancer exhibiting an alteration in interferon signaling and/or the innate immune antiviral response.

In some embodiments, the pharmaceutical composition comprises from about $10^1$ pfu to about $1\times10^{15}$ pfu of the oncolytic EHDV-TAU virus.

In further embodiments, the pharmaceutical composition is formulated for intra-tumoral, intra-venous or parenteral administration, alone or in combination with additional delivery agents.

In another aspect, the present invention provides a process for the preparation of a cancer-specific oncolytic virus, comprising infecting human cells with Epizootic Hemorrhagic Disease Virus 2-Ibaraki (EHDV2-Ibaraki), to obtain a cell adapted EHDV2-Ibaraki (EHDV2-IBA) and further modifying EHDV2-IBA to target the specific cancer by a chemical modification, site-directed mutagenesis, in-vitro evolution or any combination thereof.

In some embodiments, the present invention relates to a process or the preparation of a cancer-specific oncolytic virus comprising:

infecting human cells with Epizootic Hemorrhagic Disease Virus 2-Ibaraki (EHDV2-Ibaraki), to obtain a cell adapted EHDV2-Ibaraki (EHDV2-IBA); and serially passaging EHDV2-IBA in vitro in cancer cells exhibiting defects in interferon signaling and/or the innate immune antiviral response.

In certain embodiments of the process of the invention, the cancer is selected from prostate cancer, melanoma, renal cancer, breast cancer, lung cancer, liver cancer, colorectal cancer, gastric cancer, pancreatic cancer, bladder cancer, glioblastoma, head and neck cancer, myeloma, lymphoma and leukemia.

In a specific embodiment of the process of the invention, the step of serially passaging EHDV2-IBA in vitro in prostate cancer cells comprises the steps of:

(i) infecting LNCaP cells by EHDV2-IBA;

(ii) sonicating the infected cells obtained in step (i) to release a viral progeny;

(iii) performing a plaque assay of the viral progeny obtained in step (ii) on naive LNCaP cells;

(iv) selecting and purifying a clonal viral strain from a plaque; repeating steps (i)-(iv) for between 10 to 20 times.

BRIEF DESCRIPTION OF THE DRAWINGS

FIG. 1A shows chromatograms of a portion of exon 5 sequence of JAK1 in DU145 cells and LNCaP cells. Genomic DNA was extracted from LNCaP and DU145 cells. JAK1 specific primers were used to amplify, by PCR, exons 5 and 9 and the amplified DNA was sequenced. The sequence that appears above the chromatogram of the LNCaP cells represents the mutant sequence; the arrow marks the site of frameshift mutations (insertion of A). The chromatogram of LNCaP cells shows the mixture of wild-type and mutated sequences.

FIG. 1B shows chromatograms of a portion of exon 9 sequence of JAK1 in DU145 cells and LNCaP cells. The sequence that appears above the chromatogram of the LNCaP cells represents the mutant sequence; the arrow marks the site of frameshift mutations (insertion of C). The chromatogram of LNCaP cells shows the mixture of wild-type and mutated sequences.

FIG. 1C shows defective IFN-mediated phosphorylation of signal transducer and activator of transcription 1 (STAT1) in LNCaP cells. DU145 and LNCaP cells were incubated with IFNα (200 U/ml for 4 hours). Cells were extracted; protein lysates were separated by sodium dodecyl sulfate-polyacrylamide gel electrophoresis (SDS-PAGE) and immunoblotted with antibodies against the indicated proteins. Actin served as a loading control.

FIG. 1D shows an impaired nuclear localization of phosphorylated STAT1 in LNCaP cells. LNCaP and DU145 cells grown on glass coverslips were treated with IFNα (200 U/ml for 4 hours). Cells were fixed, permeabilized and stained with 4',6-diamidino-2-phenylindole (DAPI) and anti-pSTAT1/Alexa555-Goat-anti-Rabbit antibodies. Cells were imaged by immunofluorescence microscopy. Micrographs depict typical fields of the different cell lines prior to or following IFNα stimulation (−IFNα or +IFNα, respectively). A glowing signal indicates the merging of pSTAT1 and DAPI immunofluorescence. Bars indicate 10 μm.

FIG. 1E shows a defective IFN-mediated induction of IFN-stimulated genes (ISGs) in LNCaP cells. Graph depicts the fold change in gene expression in DU145 (black) and LNCaP (grey) cells, following IFNα stimulation (200 U/ml, for 4 hours) as measured by quantitative reverse transcription-polymerase chain reaction (qRT-PCR). Expression of ISGs in independent experiments (n=4) was normalized to measured expression levels of glyceraldehyde 3-phosphate dehydrogenase (GAPDH) housekeeping gene). Expression levels in unstimulated cells were taken as 1. *$p<0.005$.

Abbreviations: ERG (erythroblast transformation-specific (ETS)-related gene); ETV (ETS variant); FLI1 (Friend leukemia integration 1); FOXA1 (forkhead box protein A1); IDH1 (isocitrate dehydrogenase 1); IRF7 (interferon regulatory factor 7); MX1 (myxoma resistance protein 1, also known as interferon-induced GTP-binding protein Mx1); PKR (Protein kinase RNA-activated); pSTAT1 (phosphorylated STAT1); SPOP (Speckle-type pox virus and Zinc finger (POZ) protein); tSTAT1 (total STAT1).

FIGS. 2A-2D show the contribution of epigenetic mechanisms to the negative regulation of ISGs expression in prostate cancer patient samples and in LNCaP cells.

Figure 2A:
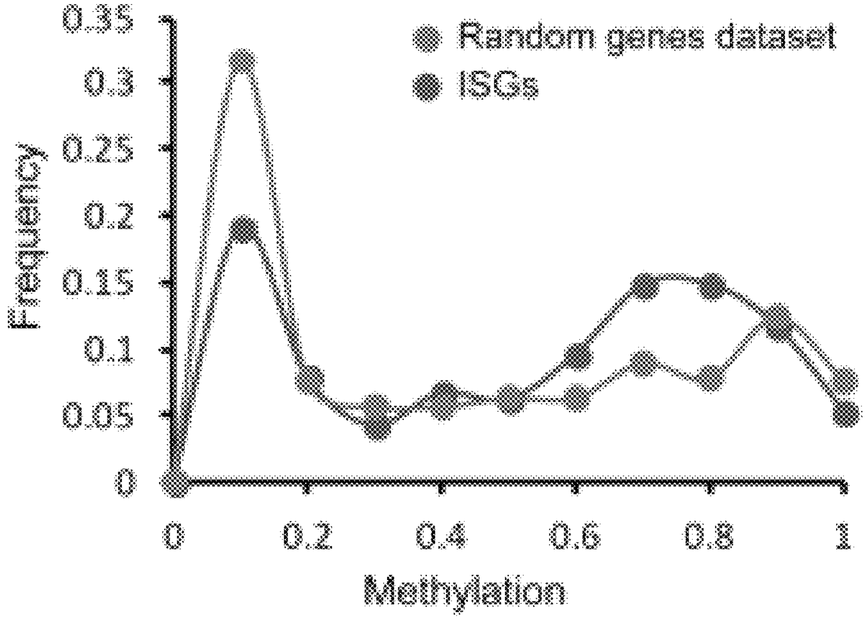

FIG. 2A shows the frequency of β values (methylation) of 500 randomly selected human genes (light grey) or 500 ISGs (dark grey) in prostate cancer patient samples (TCGA, cBioPortal).

Figure 2B:
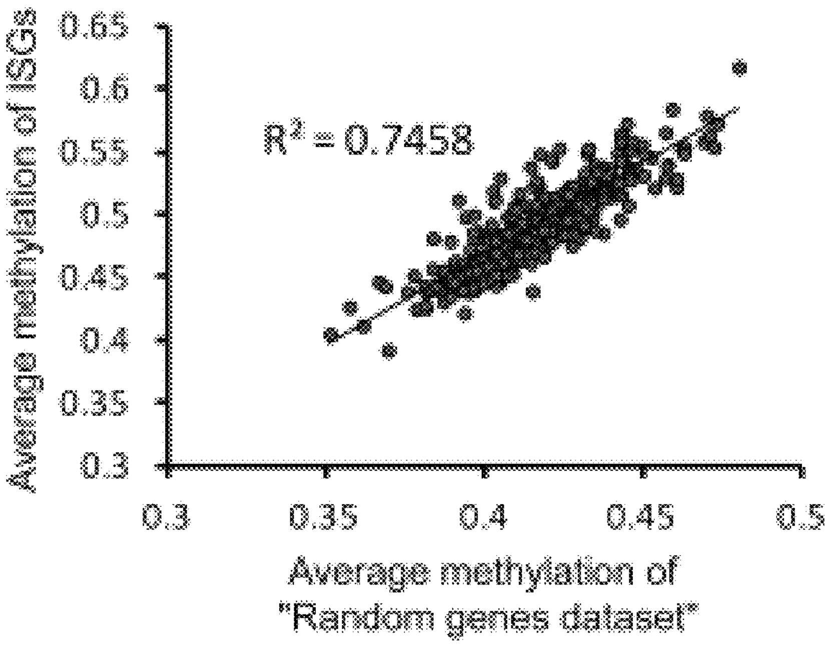

FIG. 2B shows a per-patient correlation between the average β values of 500 randomly selected human genes and 500 ISGs (same data sets as in FIG. 2A).

Figure 2C:
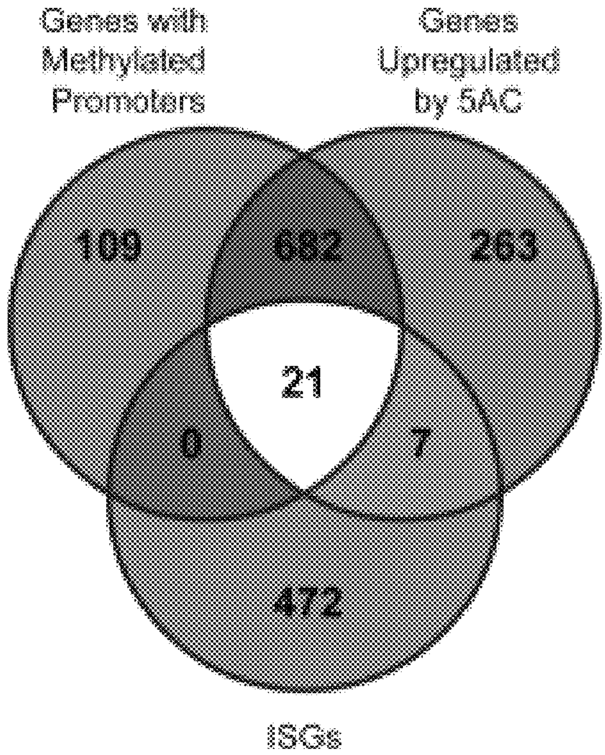

FIG. 2C is a Venn diagram showing intersections among gene lists of: "genes with methylated promoters" in LNCaP cells, "genes up-regulated by 5AC treatment" in LNCaP cells, and 500 ISGs.

Figure 2D:
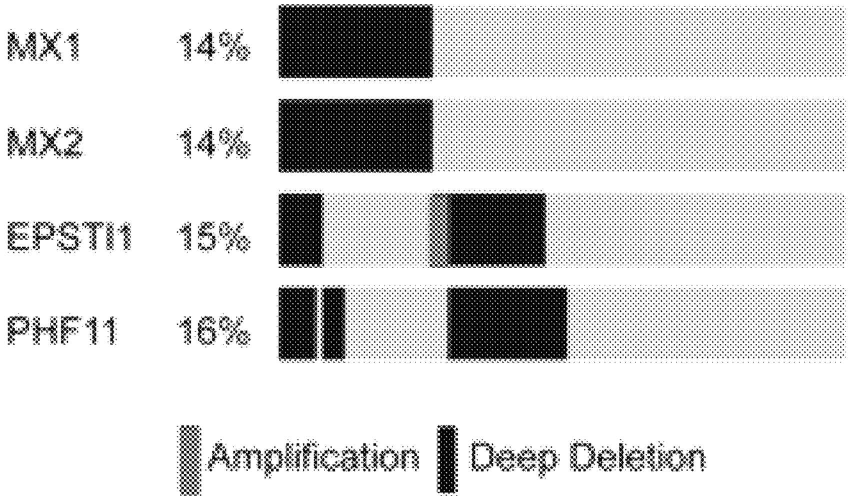

FIG. 2D is a graphical depiction of prostate cancer patient samples (TCGA, cBioPortal) with deep deletion (black), amplification (dark grey), or no alteration (light gray) of the genetic content of the indicated genes. The percentages of these alterations in the cohort are shown on the left. Patient samples are distributed along the bars; mutations that appear in the same sample are aligned above each other.

Abbreviations: 5AC (5-Aza-2'-deoxycytidine); EPSTI1 (epithelial stromal interaction 1); ISGs (interferon-stimulated genes); MX1 (myxoma resistance protein 1, also known as interferon-induced GTP-binding protein Mx1); MX2 (myxoma resistance protein 2, also known as interferon-induced GTP-binding protein Mx2); PHF11 (plant homeodomain (PHD) finger protein 11).

Figure 3A:
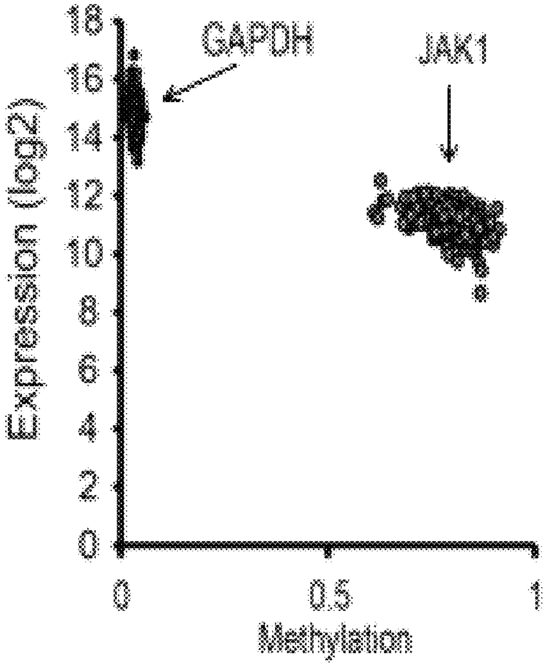
Figure 3B:
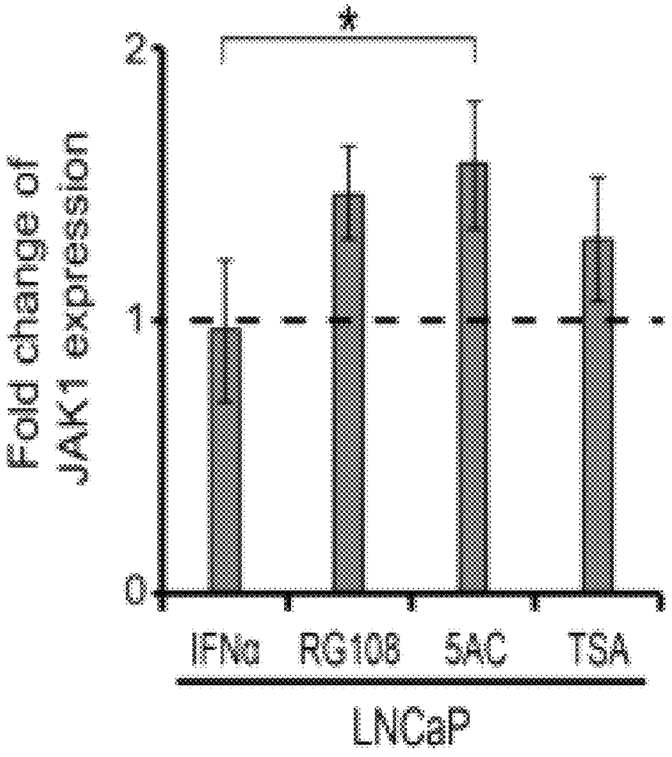
Figure 3C:
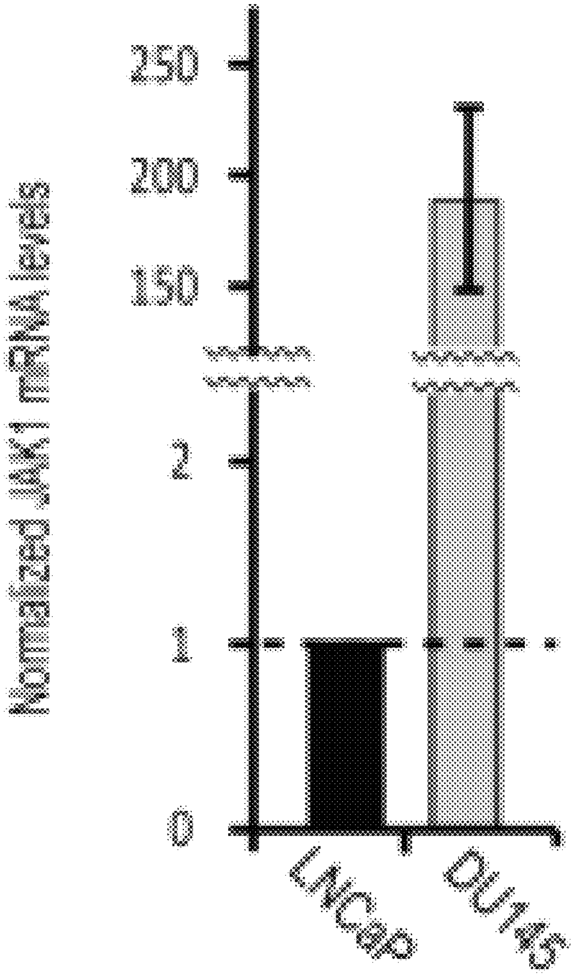

FIGS. 3A-3C show the epigenetic regulation of JAK1 in prostate cancer patient samples and in LNCaP cells.

FIG. 3A shows a per-patient correlation between the β values (methylation) and the mRNA expression of JAK1 or GAPDH.

FIG. 3B shows the relative mRNA levels of JAK1 (normalized to GAPDH mRNA, average±SD, n=3, *p<0.05) in LNCaP cells, stimulated with IFNα (200 U/ml for 4 hours), or treated with one of the indicated epigenetic modifiers (EpMs) at the concentrations as described in "materials and methods" section herein below for 24 hours. Expression of JAK1 mRNA was analyzed by qRT-PCR. The expression levels in untreated and unstimulated cells in each independent measurement were taken as 1 (dashed line).

FIG. 3C shows the normalized mRNA levels of JAK1 (relative to GAPDH mRNA) in LNCaP and DU145 cells (average±SD, n=3, ***p<0.005).

Abbreviations: 5AC (5-Aza-2'-deoxycytidine); RG108 (also known as N-phthalyl-L-tryptophan); TSA (trichostatin A).

FIGS. 4A-4G show differential infection of LNCaP and DU145 or immortalized, non-transformed prostate cells (EP cells) by serially passaged EHDV-TAU-LNCaP.

Figure 4A:
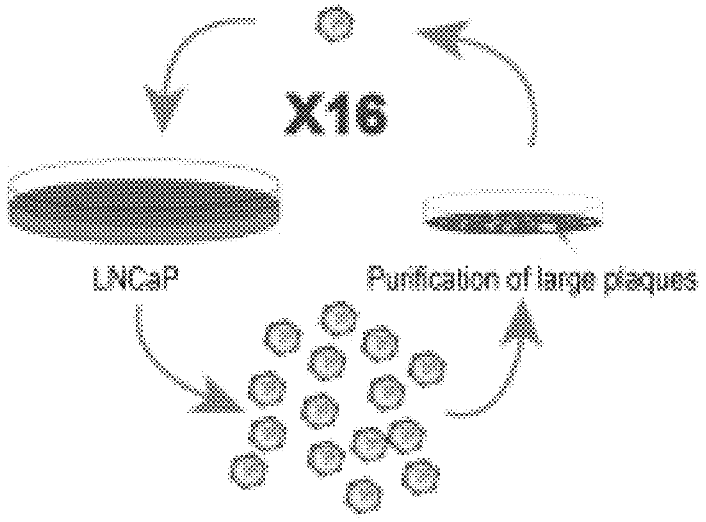

FIG. 4A schematically illustrates the selection procedure. A single virion represents a selected clonal, plaque-purified virus; whereas multiple virions represent diverse virus populations (quasispecies).

Figure 4B:
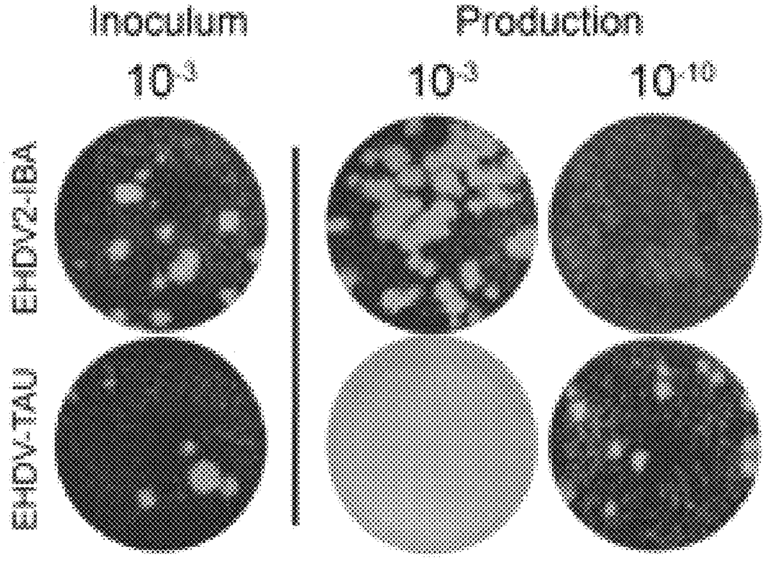

FIG. 4B shows plaque assay analysis (by crystal-violet staining) of the fold increase in titer for EHDV-TAU-LNCaP, compared to EHDV2-IBA, in LNCaP cells. The dilution employed is mentioned above the respective wells. Left inoculum ($10^{-3}$ dilution); right, dilutions ($10^{-3}$ and $10^{-10}$) of the virions (of the indicated viruses) produced in LNCaP cells (60 hours post infection).

Figure 4C:
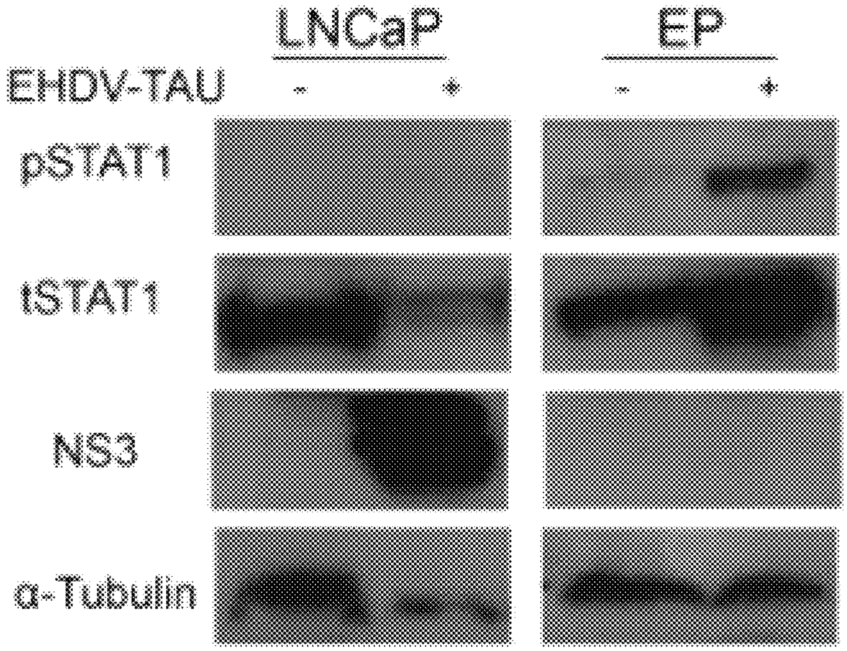

FIG. 4C shows immunoblot analysis of EHDV-TAU-LNCaP infection of EP and LNCaP cells. Lysates (100 μg protein) of EP or LNCaP cells, infected (0.05 plaque forming unit (PFU)/ml, at 45 hours post infection (hpi)) with EHDV-TAU-LNCaP were separated by 10% SDS-PAGE, blotted on nitrocellulose and probed with antibodies against the indicated proteins (pSTAT1, tSTAT1, non-structural protein 3 (NS3) and α-tubulin).

Figure 4D:
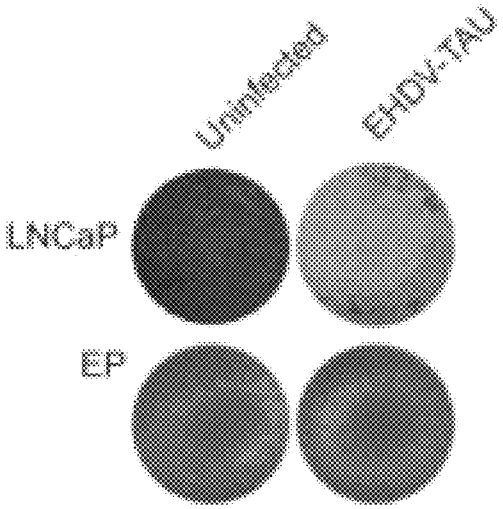

FIG. 4D shows crystal violet assessment of EHDV-TAU-LNCaP-induced death of cell cultures. LNCaP and EP cells were plated (70,000 cells/well) in 24 well plates. 24 hours post plating, cells were infected with EHDV-TAU-LNCaP (0.05 PFU/ml). At 45 hpi, cells were fixed and stained with crystal violet.

Figure 4E:
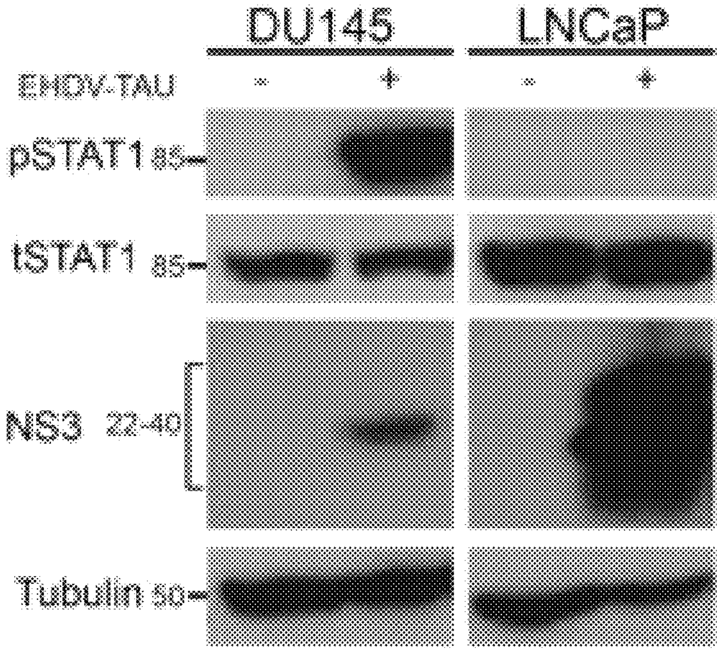

FIG. 4E shows immunoblot analysis of NS3 production and STAT1 phosphorylation in EHDV-TAU-LNCaP-infected cells. Lysates (100 μg protein) of DU145 or LNCaP cells, infected or not with EHDV-TAU-LNCaP (0.05 PFU/cell, for 45 hours) were separated by SDS-PAGE, blotted and probed with antibodies against the indicated proteins. α-tubulin was used as a loading control.

Figure 4F:
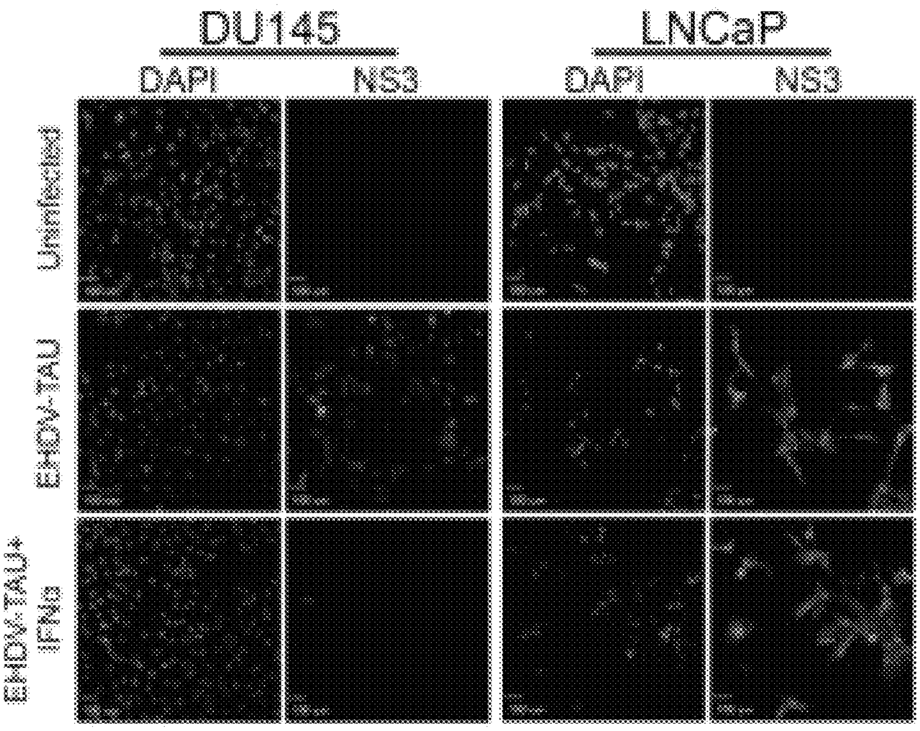

FIG. 4F shows typical fields of DU145 and LNCaP cells, stained for DAPI NS3 under the indicated conditions: uninfected, EHDV-TAU-LNCaP-infected (45 hours post infection (hpi), 0.05 PFU/cell), or EHDV-TAU-LNCaP infected (45 hpi, 0.05 PFU/cell) treated with IFNα (200 U/ml for 45 hours). Bars indicate 100 μm.

Figure 4G:
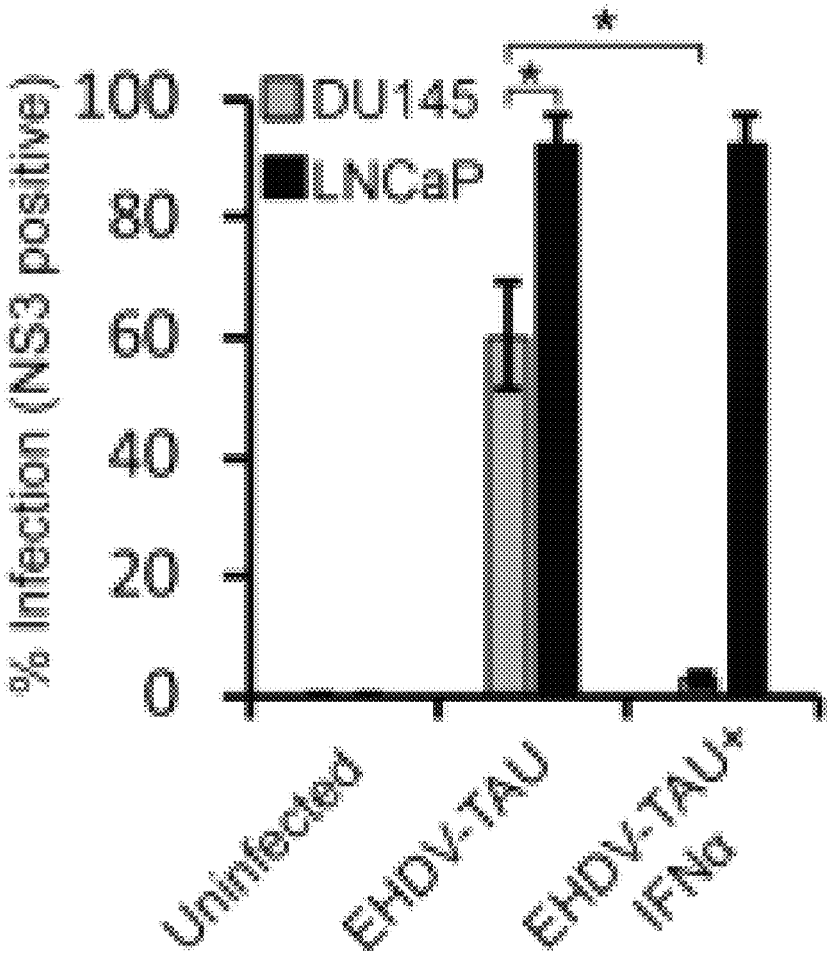

FIG. 4G shows the mean±SE percentage of NS3 positive cells. Quantification of percentage NS3 positive cells was from multiple (n=5) randomly selected fields, imaged under the same conditions as in FIG. 4D; *p<0.05.

Figure 5A:
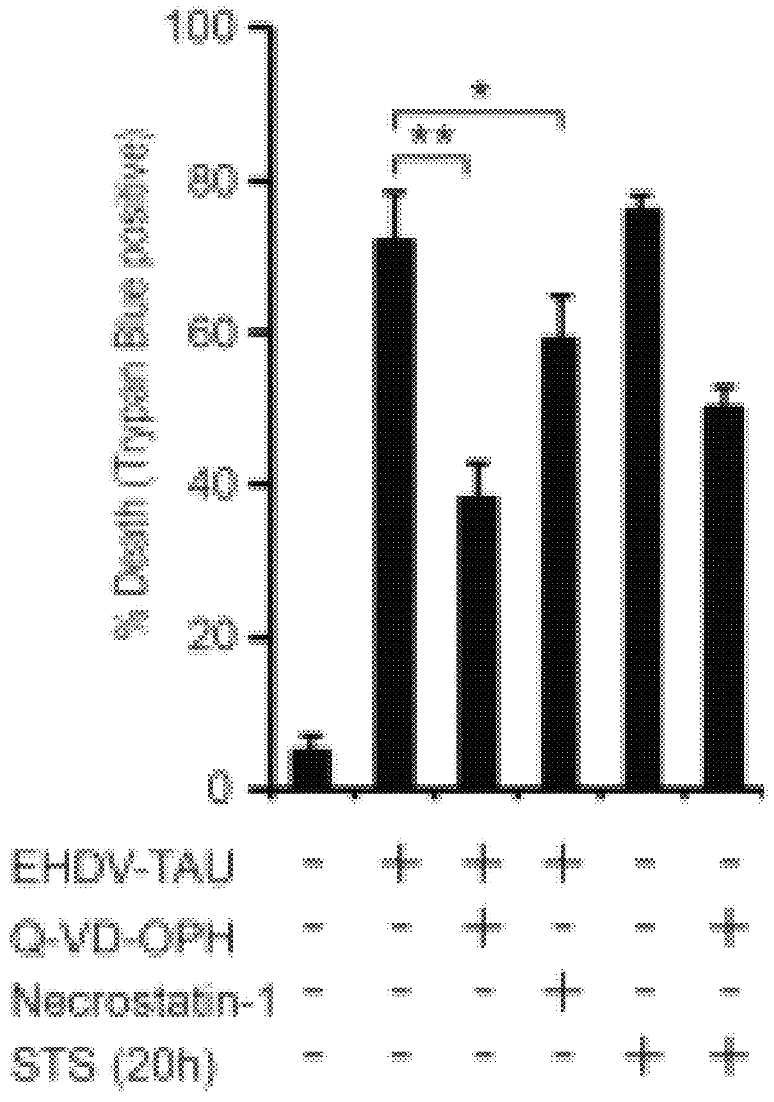
Figure 5B:
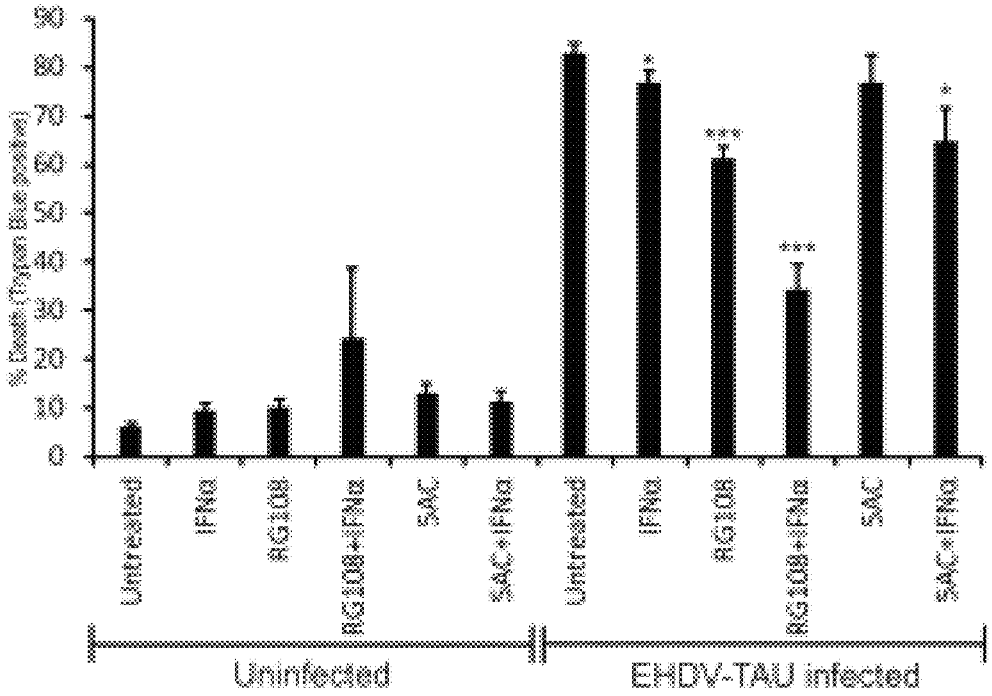

FIGS. 5A-5B show induction of apoptotic and non-apoptotic cell death by EHDV-TAU-LNCaP infection and partial inhibition of cell death by EpMs and IFNα.

FIG. 5A shows percentage of dead LNCaP cells analyzed by trypan blue exclusion assay. LNCaP cells were infected (+) or not (−) with EHDV-TAU-LNCaP (0.05 PFU/cell, for 45 hours) and treated (+) or not (−) with Q-VD-OPH (20 μM, for 45 hours during infection, or 20 hours during STS treatment), Necrostatin-1 (75 μM, for 45 hours) or staurosporine (STS, 1 μM, for 20 hours; serves as positive control of apoptosis induction). Graph depicts mean±SE (n=3) of the percentage of cell death under the indicated conditions. *p<0.05; **p<0.005.

FIG. 5B shows percentage of dead LNCaP cells analyzed by trypan blue exclusion assay. LNCaP cells were infected or not with EHDV-TAU-LNCaP (0.05 PFU/cell, for 45 hours) and treated, or not, with IFNα or the indicated EpMs. Graph depicts mean±SE (n=5) of percentage of cell death under the indicated conditions; *p<0.05; ***p<0.0005.

FIGS. 6A-6E show the IFN-stimulated restriction of EHDV-TAU-LNCaP infection in LNCaP cells in which JAK1 expression is restored (LNCaP-JAK1 cells).

Figure 6A:
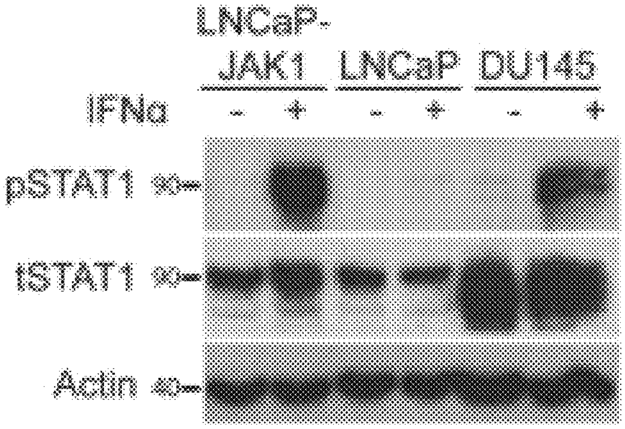

FIG. 6A shows immunoblot analysis of pSTAT1 and tSTAT1 in LNCaP-JAK1, LNCaP and DU145 cells, activated with 200 U/ml of IFNα for 2 hours.

Figure 6B:
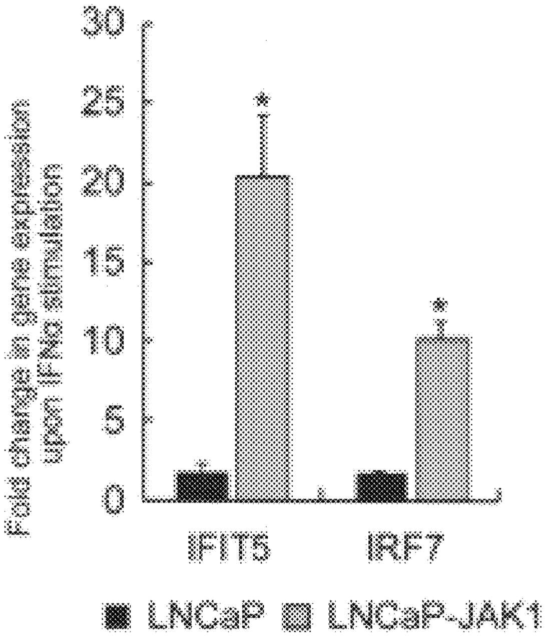

FIG. 6B shows qRT-PCR analysis of fold change in mRNA expression (normalized to GAPDH expression) of IFIT5 and IRF7 in LNCaP-JAK1 and LNCaP cells, following IFNα stimulation (200 U/ml for 24 hours). The average expression level of untreated cells was taken as 1. *p<0.05.

Figure 6C:
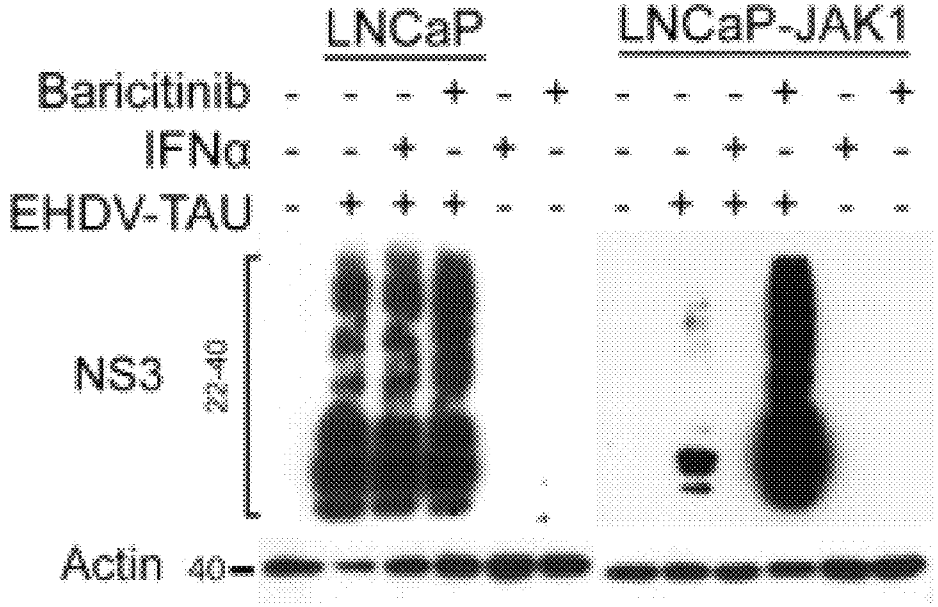

FIG. 6C shows immunoblot analysis of NS3 protein. LNCaP or LNCaP-JAK1 cells were treated with either IFNα (200 U/ml for 14 hours), or Baricitinib (0.5 μM for 14 hours), prior to, and during, infection with EHDV-TAU-LNCaP (moi 0.5, 48 hours).

Figure 6D:
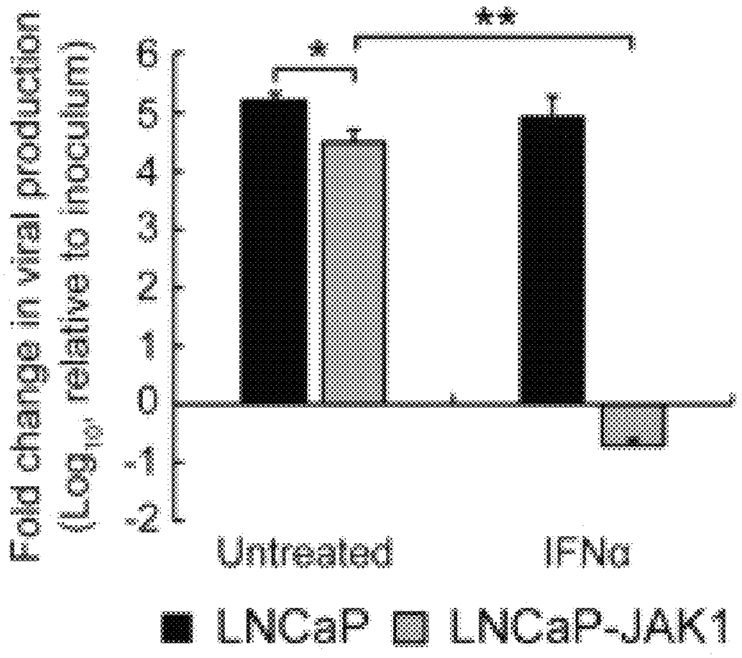

FIG. 6D shows the fold change in viral titer (relative to inoculum), following EHDV-TAU-LNCaP infection. Indicated cells were treated as in FIG. 6C and infected with EHDV-TAU-LNCaP (moi 0.05, 72 hours). Viral titer was measured by plaque assay. *p<0.05; **p<0.005.

Figure 6E:
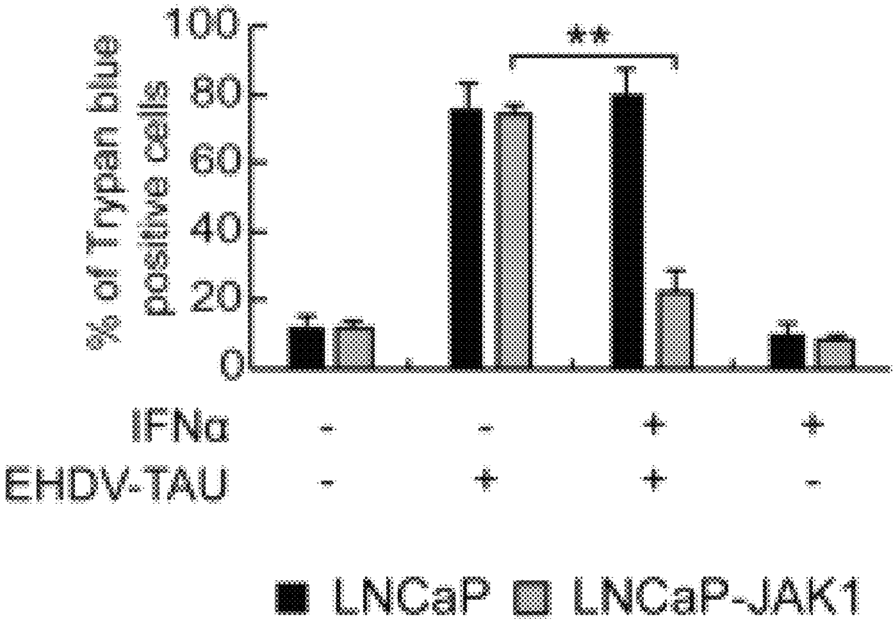

FIG. 6E shows trypan blue exclusion assay. LNCaP or LNCaP-JAK1 cells, were treated and infected as in FIG. 6C, and analyzed by trypan blue exclusion assay to determine percentages of dead cells. Graph depicts mean±SE (n=5) of the percentage of trypan blue permeable cells with and without IFNα. **p<0.005.

Abbreviations: IFIT5 (interferon induced protein with tetratricopeptide repeats 5); IRF7 (interferon regulatory factor 7).

FIGS. 7A-7F show oncolysis absent of productive viral infection in IL-6-treated LNCaP-JAK1 cells.

Figure 7A:
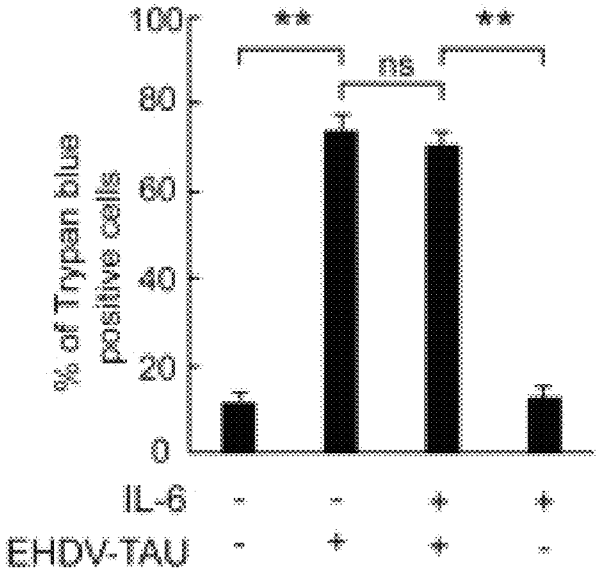

FIG. 7A shows trypan blue exclusion assay of LNCaP-JAK1 cells. The cells were treated, or not, with IL-6 (5 ng/ml, 14 h pretreatment and throughout infection), and infected (or not) with EHDV-TAU-LNCaP (moi 0.5, 48 hours). Graph depicts mean±SE (n=10).**p<0.005; ns, non-significant.

Figure 7B:
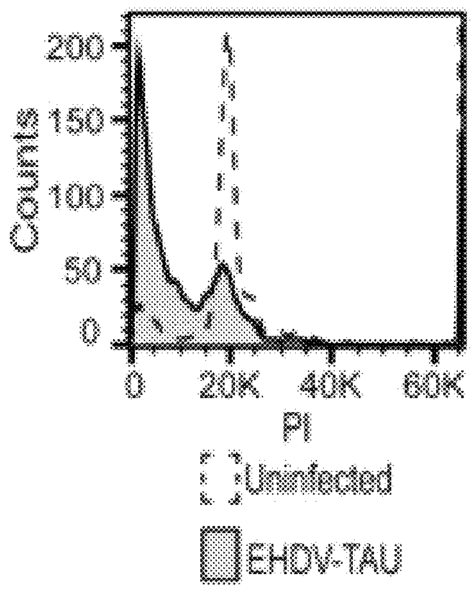

FIG. 7B is a representative FACS analysis quantifying the fraction of Sub-G1 cells upon infection with EHDV-TAU-LNCaP (moi 0.5, 48 hours).

Figure 7C:
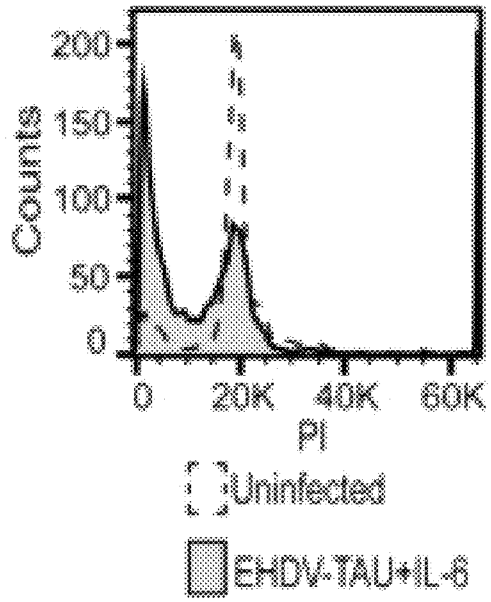

FIG. 7C is a representative FACS analysis quantifying the fraction of Sub-G1 cells upon infection with EHDV-TAU-LNCaP (moi 0.5, 48 hours) and treatment with IL-6 (5 ng/ml, 14 h pretreatment and throughout infection).

Figure 7D:
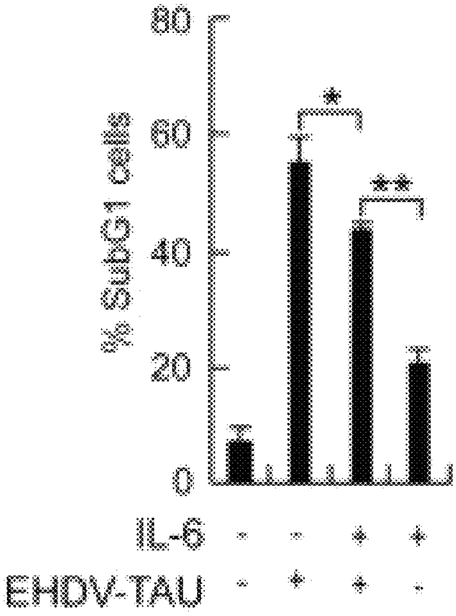

FIG. 7D shows mean±SD (n=3) of the representative results shown in FIGS. 7C and 7D. *p=0.04; **p<0.01.

Figure 7E:
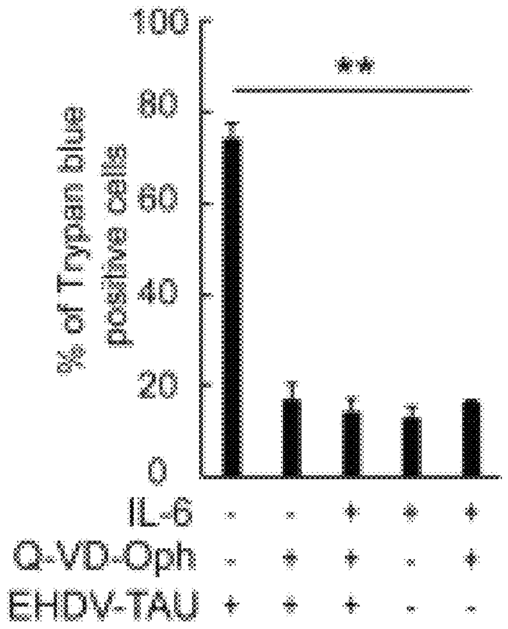

FIG. 7E shows trypan blue exclusion assay of cells treated, or not, with IL-6 (5 ng/ml, 14 hours pretreatment and throughout infection), and infected (or not) with EHDV-TAU-LNCaP (moi 0.5, 48 hours). In the presence of Q-VD-OPh (throughout pre-treatment and infection). **p<0.01.

Figure 7F:
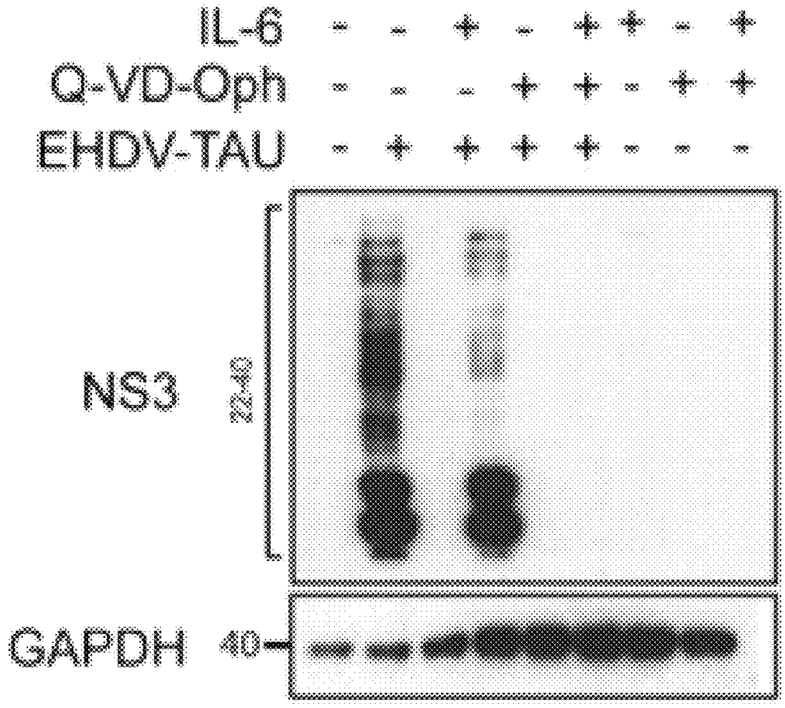

FIG. 7F shows immunoblot analysis of NS3 in LNCaP-JAK1 treated, or not, with IL-6 (5 ng/ml) and/or Q-VD-OPh (20 μM), and infected or not with EHDV-TAU-LNCaP (moi 0.5, 48 hours).

Figure 8:
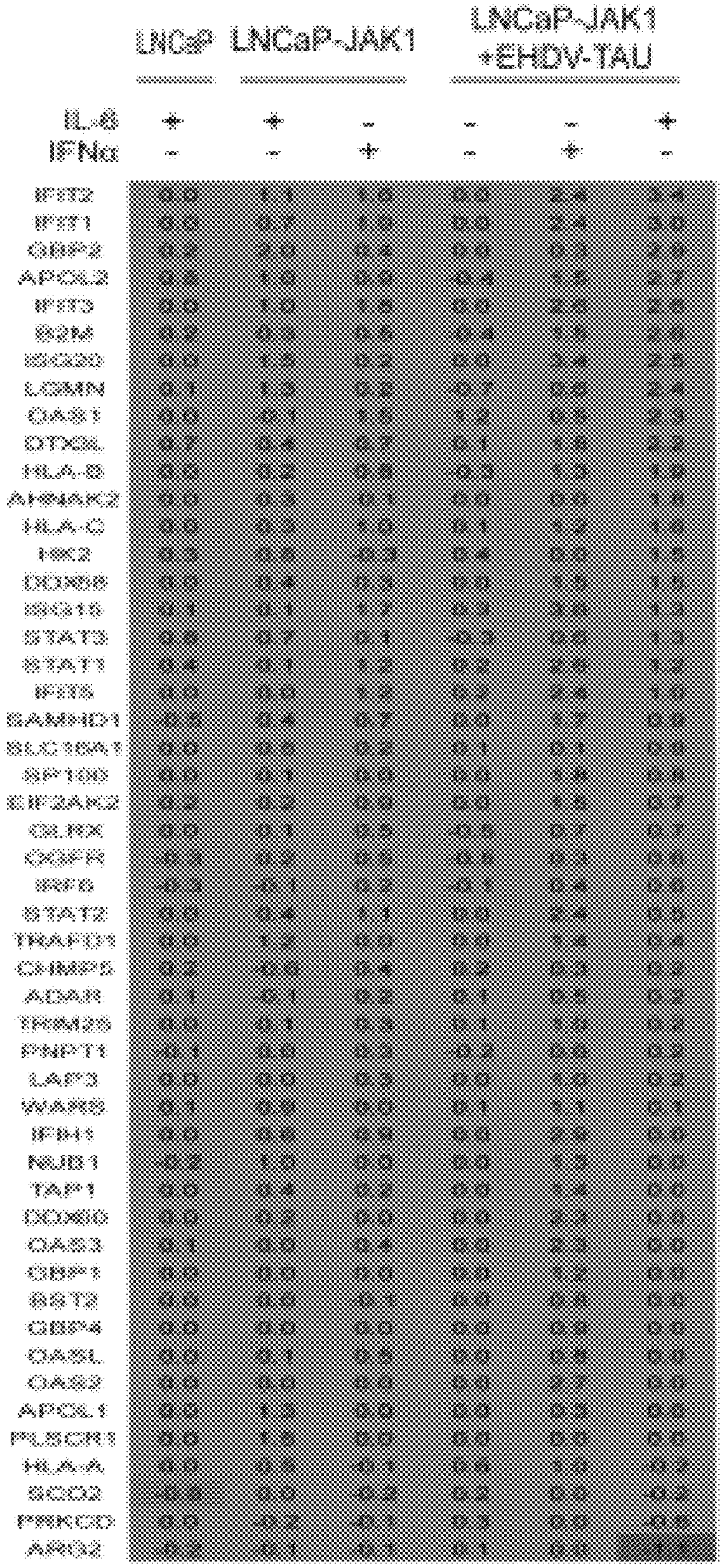

FIG. 8 is a heatmap of 50 ISGs in of IL-6-treated LNCaP-JAK1 cells that were differentially expresses after EHDV-TAU-LNCaP infection. The list of genes was generated by crossing the list of 363 differently expressed proteins with a list of 500 known ISGs. Sorting of the ISGs was according to the most extensively altered condition. Average (n=4); |Log 2 ratio| fold change in expression is presented.

FIGS. 9A-9D show IFNγ-induced STAT1 phosphorylation and partial rescue of LNCaP-JAK1 cells from EHDV-TAU-LNCaP-mediated death.

Figure 9A:
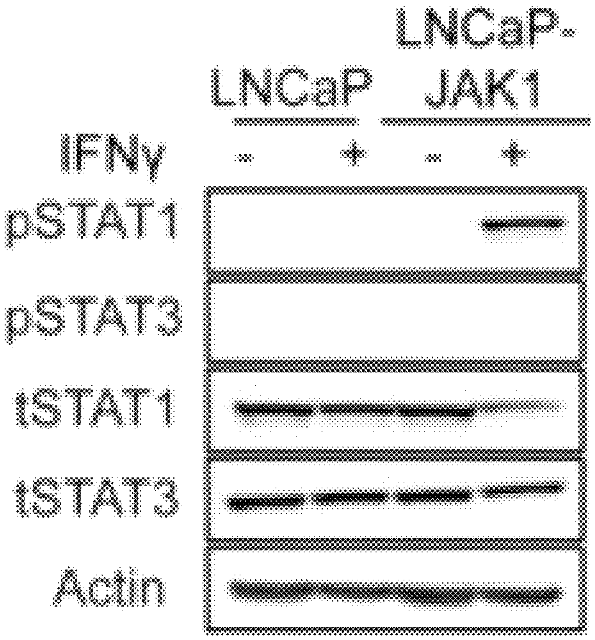

FIG. 9A shows an immunoblot analysis of STAT1 and STAT3 phosphorylation. LNCaP and LNCaP-JAK1 cells were exposed to 25 ng/ml of IFNγ for 20 minutes.

Figure 9B:
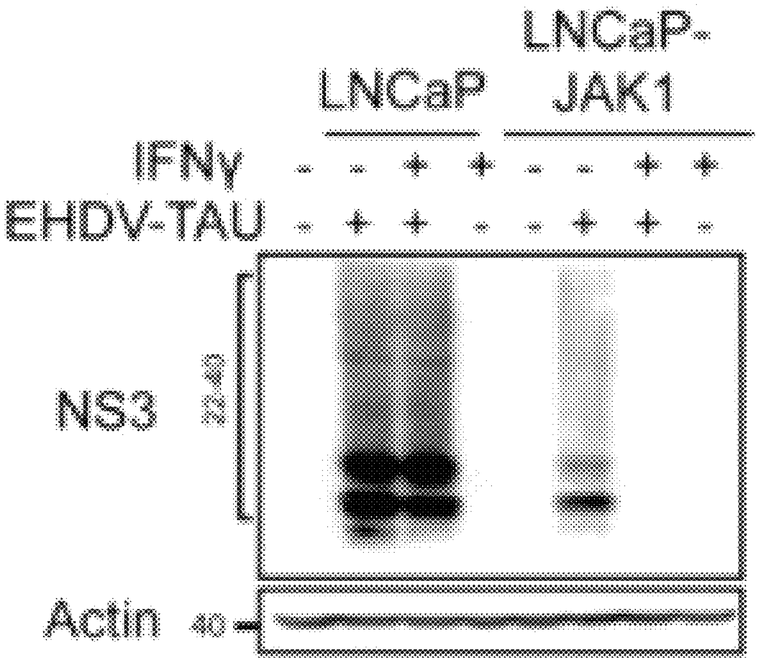

FIG. 9B shows an immunoblot analysis of NS3 in cells infected with EHDV-TAU-LNCaP and treated with IFNγ. LNCaP or LNCaP-JAK1 cells were treated or not with 25 ng/ml of IFNγ (14 hours pretreatment and throughout infection), and infected or not with EHDV-TAU-LNCaP (moi 0.5, 48 hours).

Figure 9C:
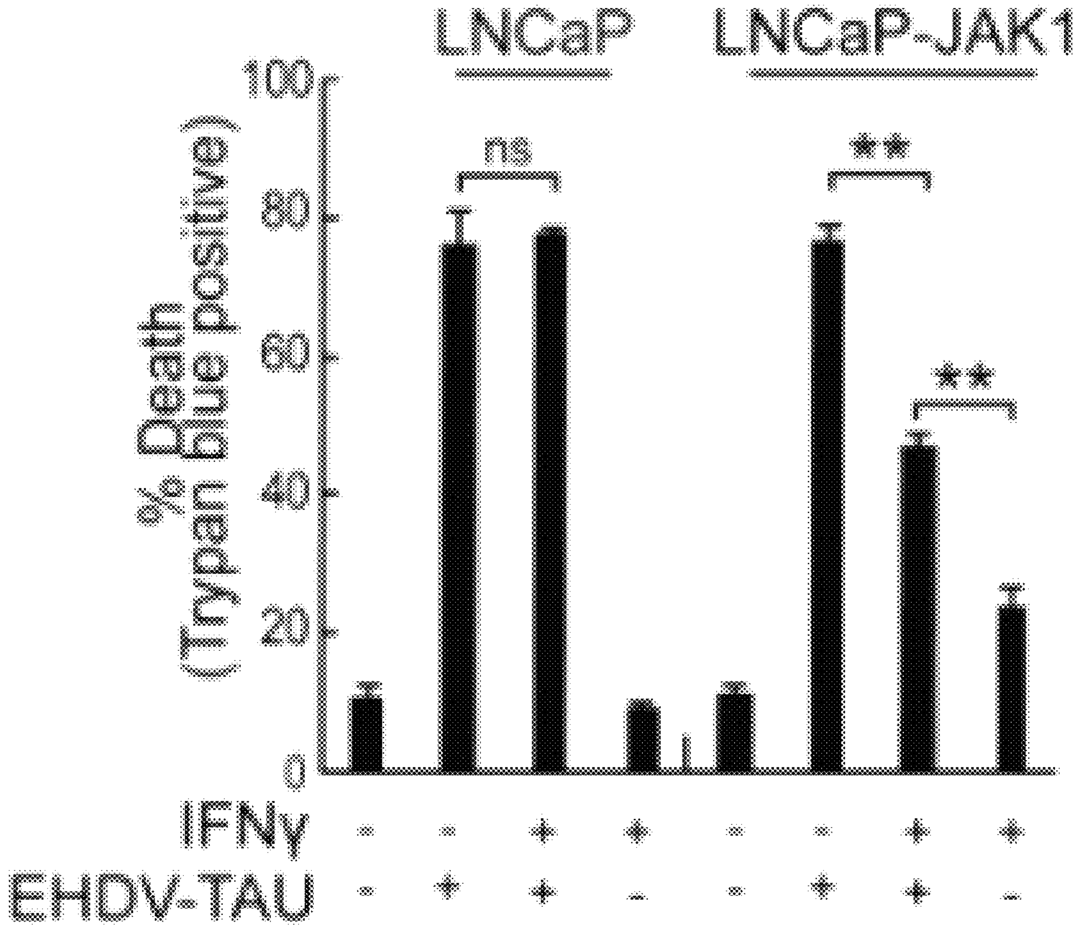

FIG. 9C shows trypan blue exclusion assay. The indicated cells were treated and infected as in FIG. 9B, and the percentage of dead cells was determined by trypan blue exclusion assay. Graph depicts mean±SE of the percentage of dead cells with and without IFNγ (n=3). **$p<0.005$; ns (non-significant).

Figure 9D:
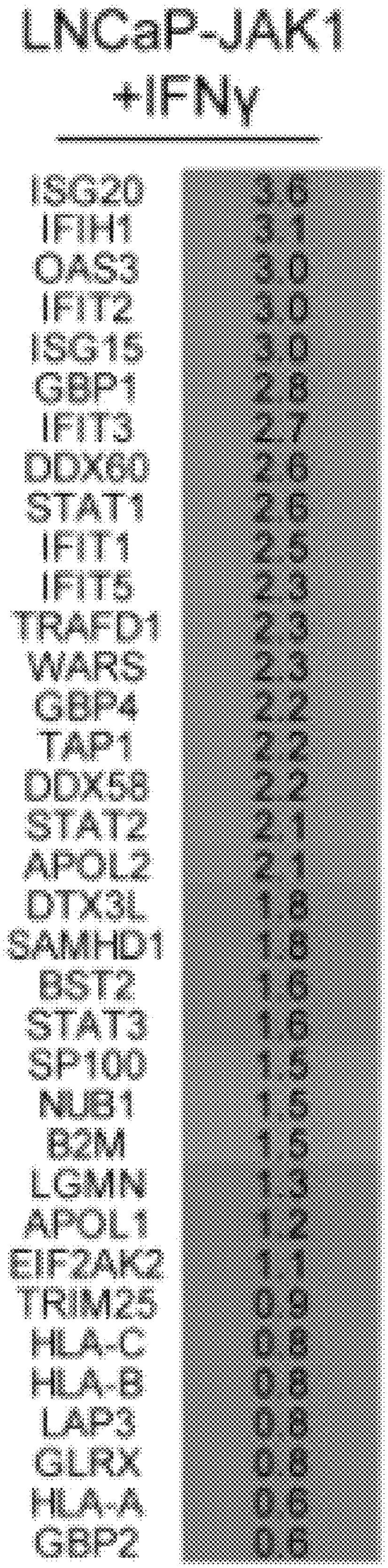

FIG. 9D is a heatmap of SILAC-measured expression of 35 upregulate ISGs in IFNγ treated LNCaP-JAK1 (25 ng/ml, 14 hours) relative to untreated LNCaP-JAK1 cells. ISG identification and values were as described in FIG. 8.

Figure 10A:
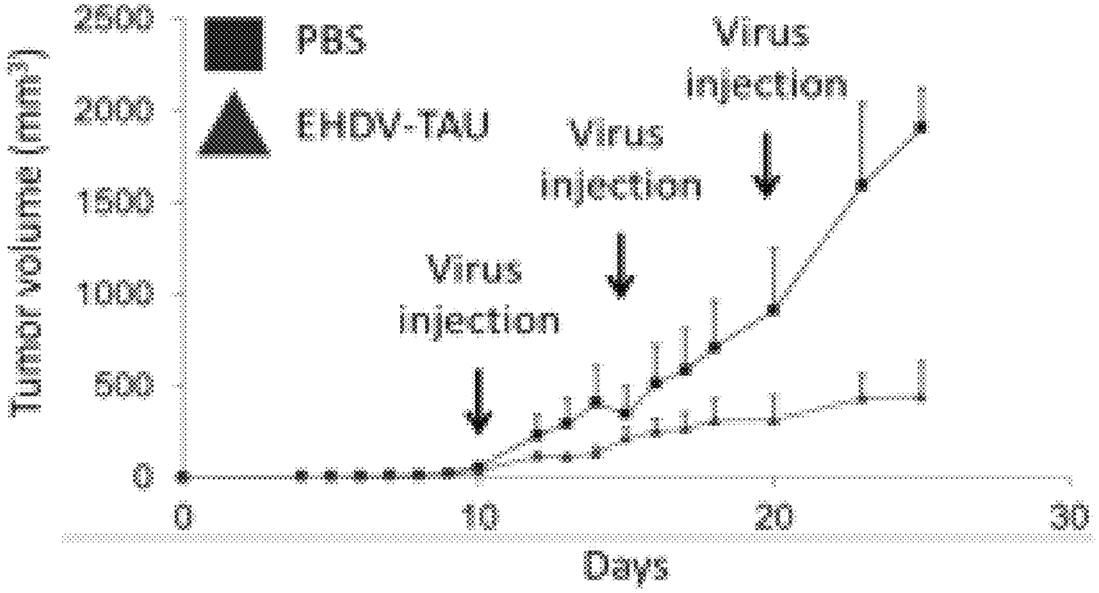
Figure 10B:
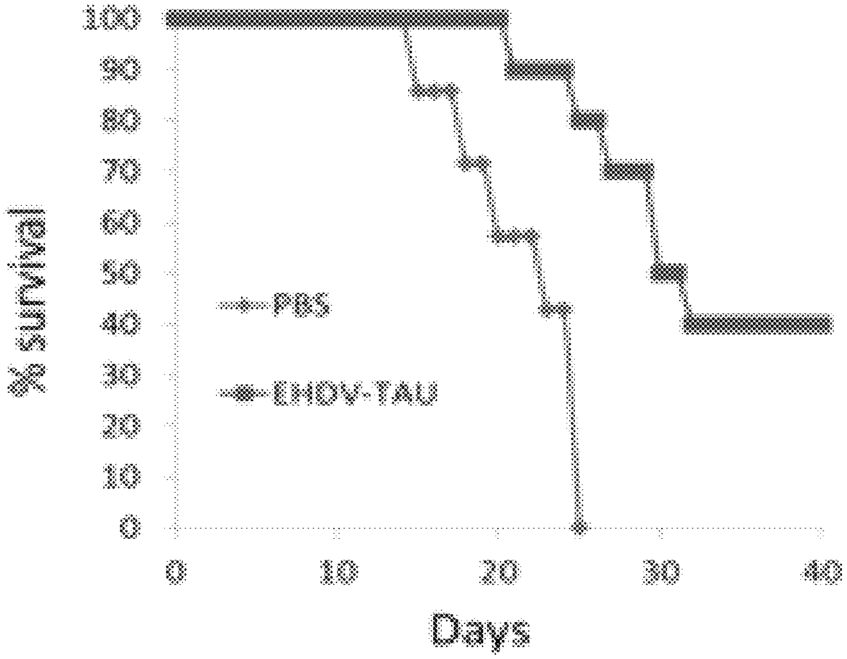
Figure 10C:
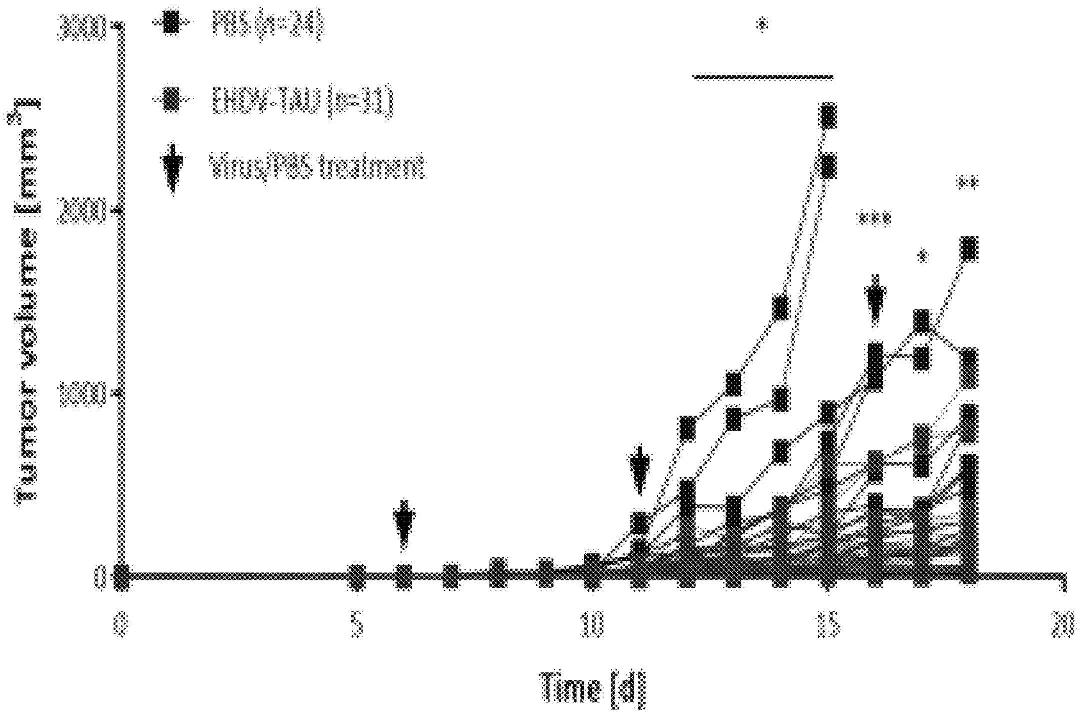

FIGS. 10A-10C show the in vivo oncolytic potential of EHDV-TAU-LNCaP in the B16 melanoma model.

FIG. 10A shows the growth of melanoma tumors in mice infected with EHDV-TAU-LNCaP. 17 C57BL/6 female mice (12 weeks old) were injected with $2\times10^6$ B16F10-mCherry murine melanoma cells. Tumor size was measured daily. After ~5 days, established sub-cutaneous (s.c.) B16 tumors were observed (~50 $mm^3$). Mice were divided into 2 groups: (I) 10 EHDV-TAU-LNCaP-infected mice; and (II) 7 PBS-injected mice, and treated with three successive (5 days apart), intra-tumor injections (indicated by an arrow), with either EHDV-TAU-LNCaP ($1\times10^8$ pfu in 50 μl PBS) or with 50 μl PBS (as injection control). Mice were weighed and tumor sizes were measured every day using calipers. Left upper graph depicts tumor volumes.

FIG. 10B shows the survival of the mice treated as described for FIG. 10A, which were terminated according to maximal tumor volume.

FIG. 10C shows a compilation of 3 independent experiments as described for FIG. 10A, in which tumor growth in individual mice is shown. *$p<0.05$; $p<0.01$; *$p<0.001$.

Figure 11A:
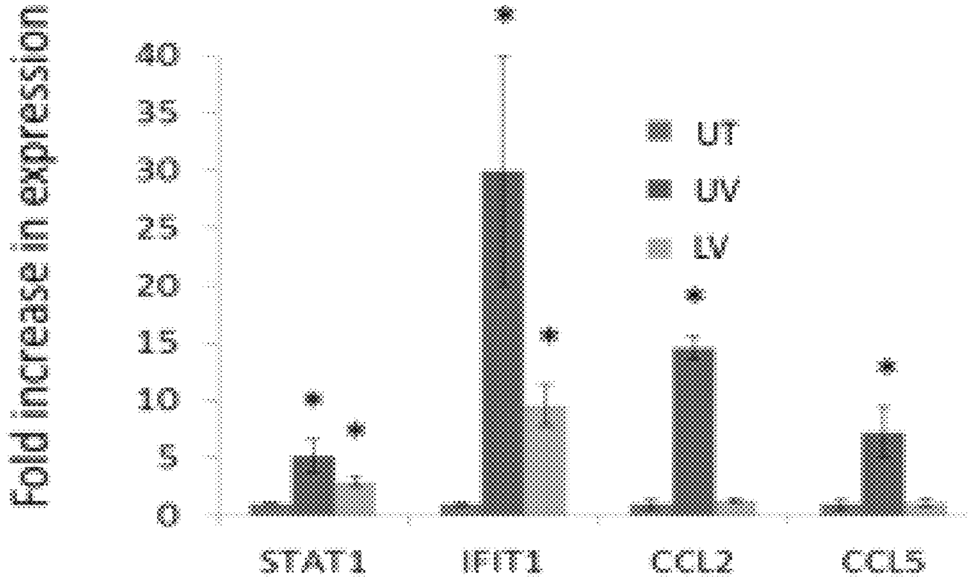
Figure 11B:
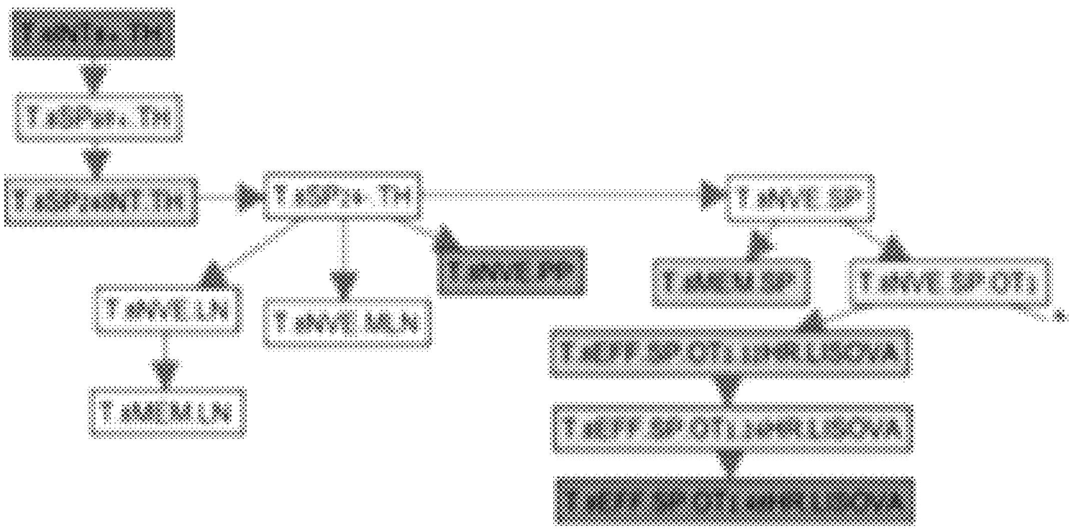

FIGS. 11A and 11B show the immune-stimulatory potential of EHDV-TAU-LNCaP-infected B16 cells and tumors.

FIG. 11A shows the fold increase in mRNA expression of the indicated genes in isolated bone marrow macrophages stimulated with condition media as indicated. Conditioned media of B16-F10 cells, infected (24 hours) or not (UT), with UV-inactivated EHDV-TAU-LNCaP (UV, 1 moi) or with replication competent EHDV-TAU-LNCaP (LV, 0.2 moi) were collected and used to stimulate isolated bone marrow macrophages for 9 hours. Gene expression was measured by qRT-PCR and expression levels were normalized to the housekeeping gene hypoxanthine phosphoribosyltransferase (HPRT). Graph depicts the mean±SD of the fold change in expression from 3 independent experiments. *$p<0.05$.

FIG. 11B shows analysis of computational deconvolution of gene expression in excised B16-F10 tumors, infected or not with EHDV-TAU-LNCaP, aimed at identification of immune cell types, carried out with ImmQuant. B16 tumors from C57BL/6 mice at 48 hours after intratumoral injection of PBS (control) or EHDV-TAU-LNCaP, were surgically excised and gene expression was measured by next generation sequencing.

Abbreviations: CCL (C-C motif chemokine ligand).

Figure 12:
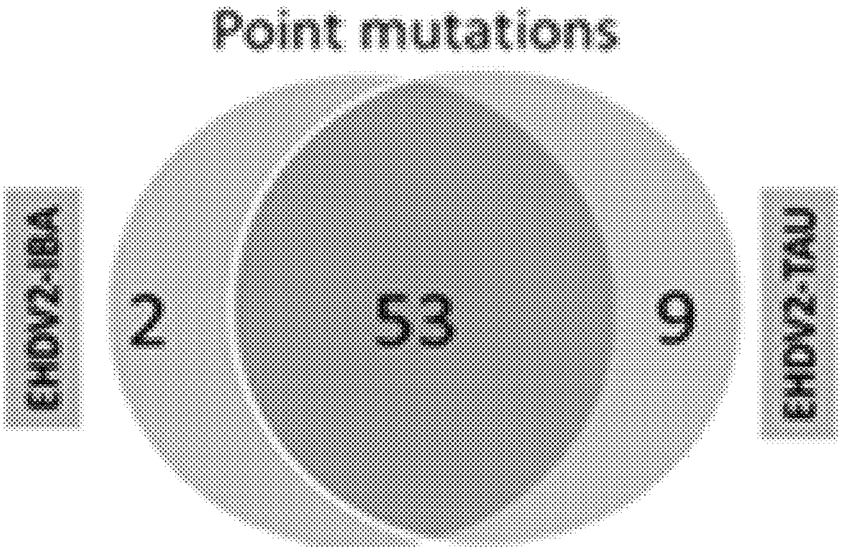

FIG. 12 shows the number and the overlap of point mutations of EHDV2-IBA (the cell adapted version of the EHDV2-Ibaraki virus) or EHDV-TAU-LNCaP relative to the published genomic sequence of EHDV2-Ibaraki virus. Sequences of EHDV2-IBA and EHDV2-TAU were determined by next generation sequencing (NGS).

FIGS. 13A-13D show the specificity of EHDV-TAU-LNCaP towards cancer cells relative to non-transformed human cells.

Figure 13A:
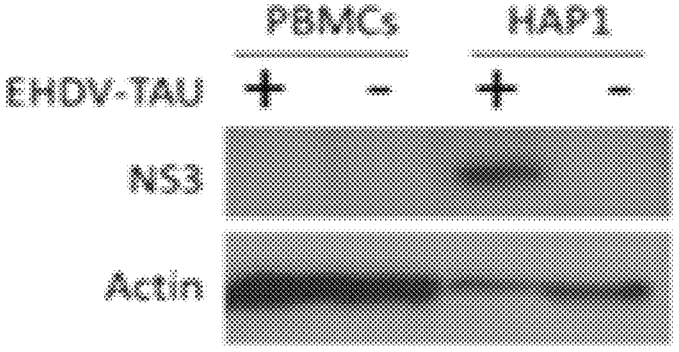

FIG. 13A shows immunoblot of peripheral blood mononuclear cells (PBMCs) or HAP1 leukemia cells, infected or not with EHDV-TAU-LNCaP (48 hours). Lysates were probed for NS3 and actin (as loading control).

Figure 13B:
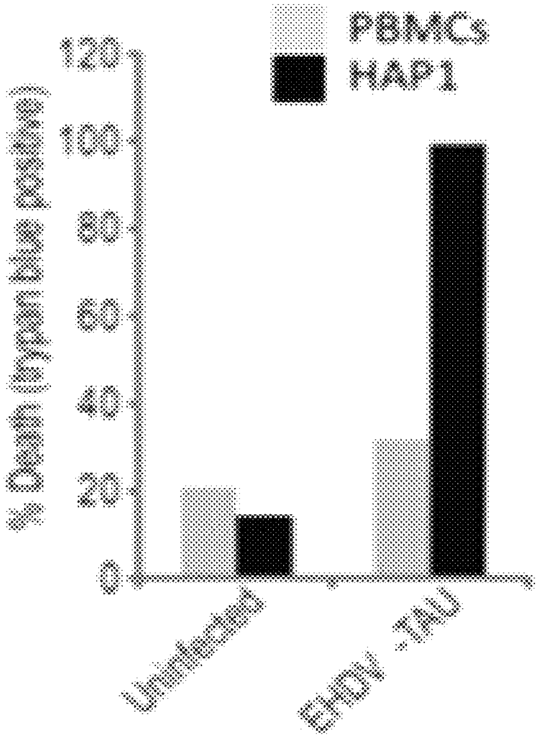

FIG. 13B shows the percent of trypan blue positive (i.e., dead) cells in infected and non-infected PBMC and HAP1 cell cultures.

Figure 13C:
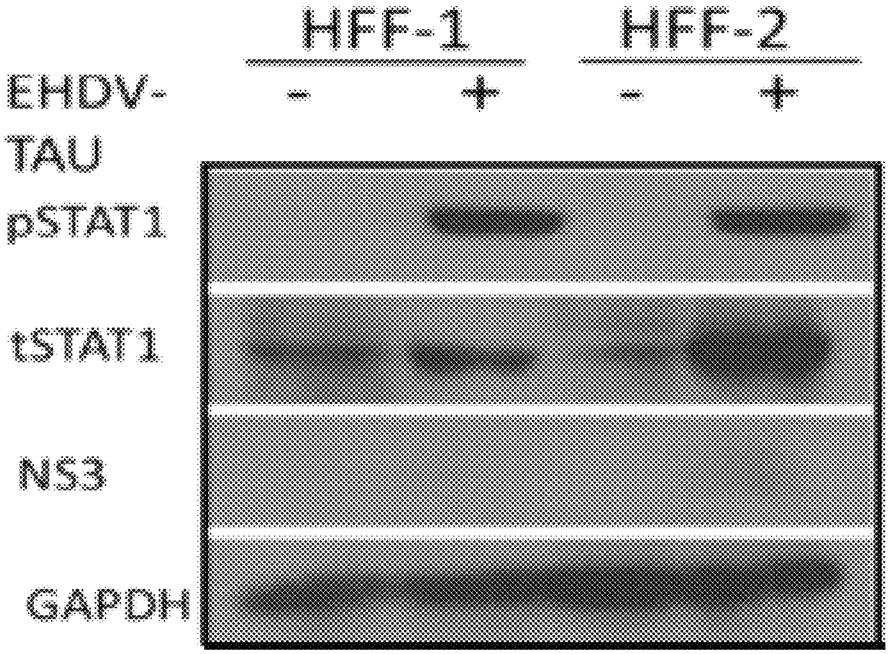

FIG. 13C shows immunoblot of human foreskin fibroblasts (HFF) cells, infected or not with EHDV-TAU-LNCaP (50 hours). Lysates were probed for NS3, total- and phospho-STAT1 and GAPDH (as loading control).

Figure 13D:
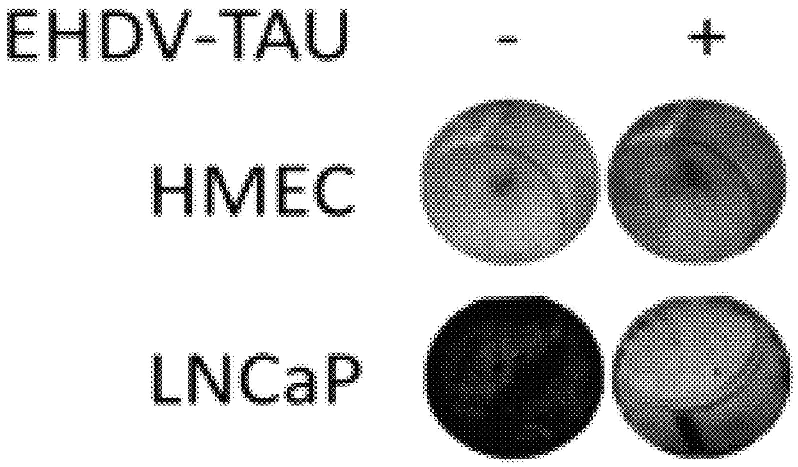

FIG. 13D shows crystal violet assessment of cell viability. Human immortalized endothelial cells (HMEC) or LNCaP cells were infected or not with EHDV-TAU-LNCaP. At 72 hours post infection the amount of viable cells in culture was assessed by staining with crystal violet.

FIGS. 14A-14D show the killing potential and the immune activation potential of EHDV-TAU-LNCaP in a human melanoma model or a human microglia model.

Figure 14A:
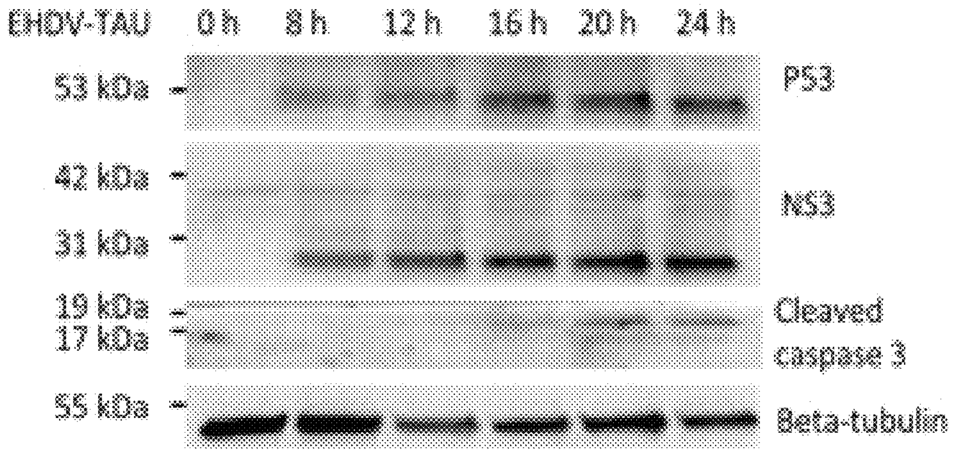

FIG. 14A shows protein expression, measured by immunoblotting with the indicated antibodies. A brain-metastatic variant of human melanoma cells (termed YDFR-CB3) were infected with EHDV-TAU-LNCaP at moi 1. Infection was stopped at every 4 hours.

Figure 14B:
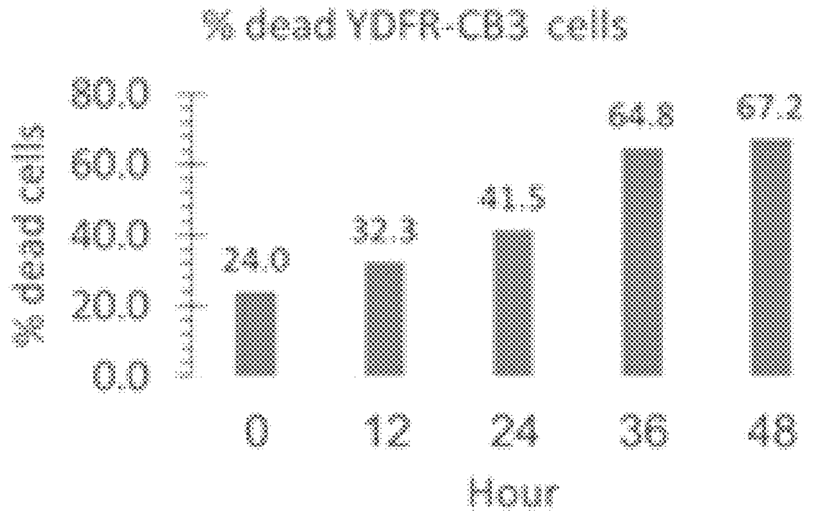

FIG. 14B shows the percentage of dead cells, assessed by methylene blue assay. YDFR-CB3 cells were infected with EHDV-TAU-LNCaP at moi 1. Infection was stopped at every 12 hours.

Figure 14C:
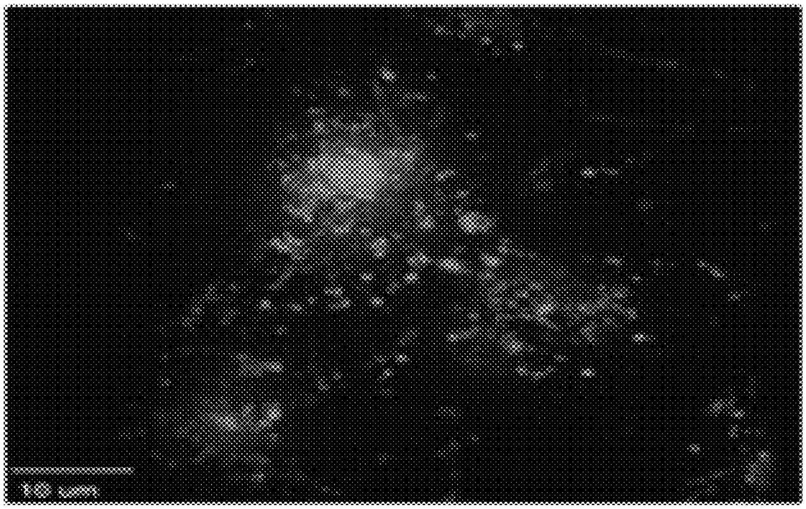

FIG. 14C is a representative image of YDFR-CB3 cells post infection. YDFR-CB3 cells expressing mCherry fluorescent protein were infected with EHDV-TAU-LNCaP at moi 1. After 48 hours infections the cells were imaged by spinning disk confocal microscopy.

Figure 14D:
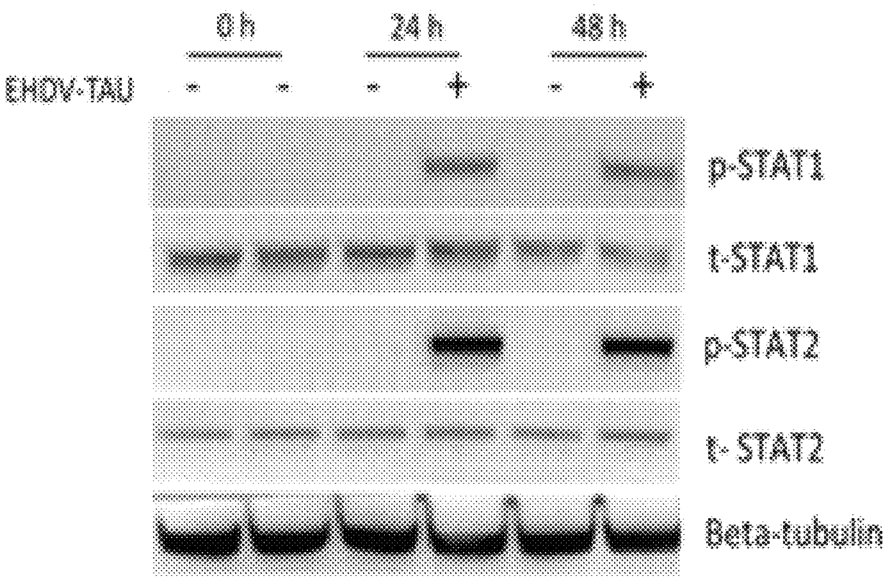

FIG. 14D shows protein expression, measured by immunoblotting with the indicated antibodies. YDFR-CB3 cells were infected (or not) with EHDV-TAU-LNCaP at moi 1 for the indicated time points. Cell media were collected and employed to activate immortalized human brain microglia cells (1 hour incubation, 1/3 dilution into full serum). Microglia cells were then lysed and immunoblotted with the indicated antibodies.

DETAILED DESCRIPTION

The present invention relates to Epizootic Hemorrhagic Disease virus-Tel Aviv University (EHDV-TAU), which is a novel oncolytic virus developed by a selection process (also termed "in-vitro evolution") of the Epizootic Hemorrhagic Disease Virus 2-Ibaraki strain. The modified virus shows efficacy and safety results in both in-vitro and in-vivo studies. EHDV-TAU has undergone pre-clinical testing, exhibiting efficacy, specificity and safety in cell culture and mouse tumor models. Specifically, the virus efficiently replicates in, and kills transformed cells, especially cells that show alterations in the innate-immune interferon-based antiviral response. In contrast, no enhanced killing was observed for infected, non-transformed cells and infected immunocompetent mice.

It should be noted that the Ibaraki strain of the Epizootic Hemorrhagic Disease virus (EHDV2-Ibaraki), having the RNA sequence as set forth in SEQ ID NO: 1, naturally infects ruminants, and not humans. Infecting human cells in vitro with EHDV2-Ibaraki produces a cell adapted viral strain named EHDV2-IBA. Further modifications of EHDV2-IBA result in novel oncolytic viral strains (EHDV-TAU) which can be directed to a specific cancer of choice. These modifications include, but are not limited to, chemical modifications, site-directed mutagenesis and/or in-vitro evolution. For example, the process of in-vitro evolution of EHDV2-IBA, having the RNA sequence as set forth in SEQ ID NO: 2, by its serial passaging in the human prostate cancer cell line LNCaP produces an oncolytic viral strain designated as EHDV-TAU-LNCaP, which specifically targets prostate cancer and has the RNA sequence as set forth in SEQ ID NO: 3. The unique features of EHDV-TAU-LNCaP, which are acquired during the evolution process, include the million fold increase in efficiency of production of viral progeny, while infecting LNCaP human prostate cancer cells.

Notably, EHDV-TAU doed not exist in nature, nor could naturally evolve.

It should be appreciated that the oncolytic virus of the invention, which is targeted to a specific cancer can infect and exert its oncolytic effects on other cancer cells. For example, EHDV-TAU-LNCaP, which is targeted to prostate cancer cells, shows beneficial effects in melanoma cells.

The adapted/modified viral strain advantages in the treatment of cancers reside in both intrinsic features of the original EHDV2-Ibaraki strain, and unique features acquired during the in-vitro selection (evolution) process. For example, the original EHDV2-Ibaraki strain provides the following essential features:

a. The veterinary origin of the EHDV2-Ibaraki strain means that there is no prior immunity in humans. This is a critical feature of the oncolytic virus of the invention, because the treated subjects do not have neutralizing antibodies that can bind the virus and limit its delivery, and their immune system cannot eradicate the viral infection.
b. The EHDV2-Ibaraki strain is able to manipulate cellular resources and milieu, including induction of apoptosis, autophagy and cell stress.
c. The EHDV2-Ibaraki strain is able to induce cytolysis.
d. The EHDV2-Ibaraki strain exhibits high rate of progeny production.
e. The molecular composition of the EHDV2-Ibaraki strain efficiently engages the innate immune anti-viral system.

Oncolytic virotherapy aims at the eradication of tumors through the selective infection and killing of cancer cells and the elicitation of anti-tumor immunity. Tumor-induced alterations to multiple molecular features of the cell autonomous antiviral response, including defects in JAK-STAT signaling, expose cancerous cells (e.g., PCa cells) to viral infection and viral-induced cell death. The ability of the oncolytic virus EHDV-TAU to exploit such alterations, and stimulate anti-tumor immunity, strengthens its efficiency as an anti-cancer therapeutic agent.

Accordingly, the present invention provides a therapeutic viral agent for oncolytic immune virotherapy of cancer. This form of therapy aims to directly and specifically kill cancer cells, while eliciting anti-tumor immunity.

In one aspect, the present invention relates to a method for treating cancer exhibiting at least one alteration in interferon signaling and/or the innate immune antiviral response, comprising administering EHDV-TAU, or a pharmaceutical composition comprising thereof, to a subject.

In another aspect, the invention relates to a pharmaceutical composition comprising an effective amount of the oncolytic virus EHDV-TAU and a pharmaceutically acceptable carrier or vehicle, for treating cancer exhibiting at least one alteration in interferon signaling and/or the innate immune antiviral response.

The expression "defects in interferon signaling and/or the innate immune antiviral response" or "alteration in interferon signaling and/or the innate immune antiviral response" refers to cells presenting reduced or enhanced signaling responses following stimulation with any of the members of the interferon family (e.g. interferon alpha, beta, gamma or delta) and/or cells that fail to counteract viral infection and replication. The alterations in the signaling responses include (but not restricted to) defective receptors (reduced or elevated expression levels and/or functions); defective signal mediators (e.g. reduced or elevated expression levels and functions of JAK and/or STAT proteins) and/or decrease or increase in the expression or function of interferon-stimulated genes (ISGs). The antiviral response may also include an alteration in additional signaling pathways and/or cellular effectors of the antiviral response, including sensors of pathogen-associated molecular patterns (PAMPS), restriction factors and/or signal mediators (e.g. NF-kB).

It should be noted that in addition to cells which are naturally deficient in interferon signaling, alterations in interferon signaling and/or the innate immune antiviral response may also be artificially induced in cells that are originally interferon competent, for example by applying CRISPR/Cas9-mediated knockout of JAK1 to DU145 prostate cancer cells.

The terms "treating" "treatment" or "therapy" as used herein means: (1) to ameliorate or prevent the cancer or one or more of the biological manifestations of the cancer, (2) to interfere with (i) one or more points in the biological cascade that leads to or is responsible for the cancer or (ii) one or more of the biological manifestations of the cancer, (3) to alleviate one or more of the symptoms, effects or side effects associated with the cancer or treatment thereof, or (4) to slow the progression of the cancer or one or more of the biological manifestations of the cancer. Prophylactic therapy is also encompassed by this term. The skilled artisan will appreciate that "prevention" refers to the prophylactic administration of an oncolytic virus to substantially diminish the likelihood or severity of a cancer or biological manifestation thereof, or to delay the onset of such cancer or biological manifestation thereof. Prophylactic therapy is appropriate, for example, when a subject is considered at high risk for developing cancer, such as when a subject has a strong family history of cancer or when a subject has been exposed to a carcinogen. For example, treatment of a tumor or metastasis in a subject according to the invention encompasses any manner of treatment that results in slowing of tumor growth, lysis of tumor cells, reduction in the size of the tumor, prevention of new tumor growth, or prevention of metastasis. These terms also include eliciting anti-tumor immunity in a subject.

The term "subject" as used herein refers to any mammal, including a human.

The phrase "therapeutically effective amount" as used herein refers to the amount of oncolytic virus that is sufficient to induce oncolysis, the disruption or lysis of a cancer cell, as well as slowing, inhibition or reduction in the growth or size of a tumor, and includes the eradication of the tumor in certain instances. The skilled person will appreciate that the therapeutically effective amount can be adjusted in accordance with standard practices as needed according to the cancer type and state, the administration mode, and/or the condition of subject.

The term "oncolytic virus" refers to a virus that replicate selectively in tumor cells in cancer cells. The oncolytic virus can kill a tumor cell following infection of the tumor cell either in vitro or in vivo, while showing no or minimal replication in non-cancerous cells. For example, an oncolytic virus can cause death of the tumor cell by lysing the tumor cell or inducing cell death of the tumor cell. As used herein, the term encompasses RNA vectors and viral particles of EHDV-TAU.

The term "modified virus", "adapted virus" or "recombinant virus" refers to a virus that is altered compared to a parental strain of the virus. Typically a modified virus has one or more truncations, mutations, insertions or deletions in the genome of virus.

The term "productive infection" as used herein refers to a viral infection of cells, resulting in the production of new virions, which in turn can infect other cells.

The term "abortive infection" or "non-productive infection" as used herein refers to viral infection of cells, wherein some or all viral components (e.g., RNA molecule) have been synthesized, but no new infective virions are produced.

It should be noted that the oncolytic virus of the invention can also induce a unique phenomenon termed "oncolysis by non-productive viral infection (ONPVI)". According to this type of oncolysis, the virus kills the target cancer cells without producing new infective virions. This phenomenon usually takes place in the presence of inflammatory cytokines (e.g., IL-6 or IFNγ), which are present in the tumor microenvironment. Therefore, a heterogenous tumor, in which some cells are defective in interferon signaling while others are not, EHDV-TAU exerts its anti-tumorigenic effect either by productive infection and killing of cells or by ONPVI.

Treatment regimens may vary, and often depend on tumor type, tumor location, disease progression, and health and age of the patient. The treatment according to the invention may include various "unit doses." As used herein, plaque forming unit (pfu) or infectious unit (IU) refers to the number of infectious or live viruses. It thus reflects the amount of active virus in the pharmaceutical composition administered to the subject. The pfu can be determined using a plaque formation assay or an end-point dilution assay, which are standard assays known to one of skill in the art. The quantity to be administered, and the particular route and formulation, are within the skill of those in the arts. Unit doses range from $10^3$, $10^4$, $10^5$, $10^6$, $10^7$, $10^8$, $10^9$, $10^{10}$, $10^{11}$, $10^{12}$, $10^{13}$ pfu and higher. Alternatively, at least about $1\times10^1$, $1\times10^2$, $1\times10^3$, $1\times10^4$, $1\times10^5$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or higher infectious viral particles or pfu, including all values and ranges between, can be delivered to the tumor or tumor site, or to other places in the body.

In one embodiment, a pharmaceutical composition comprising a pharmaceutically acceptable carrier and a single dose of at least about $1\times10^1$, $1\times10^2$, 1×103, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or more infectious viral particles or plaque forming units (pfu), including the various values and ranges there between is administered one or more times to the subject.

As used herein, the term "carrier" includes any and all solvents, vehicles, dispersion media, coatings, diluents, antibacterial and antifungal agents, isotonic and absorption delaying agents, buffers, carrier solutions, suspensions, colloids, and the like, compatible for administration to human subjects.

The cancers encompassed by the invention exhibit at least one alteration in the innate-immune interferon-based anti-viral response. According to a specific embodiment, the cancer is selected from prostate cancer, melanoma, renal cancer, breast cancer, lung cancer, liver cancer, colorectal cancer, gastric cancer, pancreatic cancer, bladder cancer, glioblastoma, head and neck cancer, myelomas, lymphomas and leukemias, as well as all types of malignancies exhibiting alterations in interferon signaling and/or the innate immune antiviral response.

The routes of administration of the oncolytic virus according to the invention and the pharmaceutical compositions comprising thereof, depend on type, stage and location the tumor, and the age and health of the subject. The administration modes include, e.g., parenteral, intra-tumoral, intradermal, transdermal, intravenous, intramuscular, intranasal, subcutaneous, percutaneous, intratracheal, intraperitoneal, intravesical, inhalation, perfusion, lavage, and oral administration. It should be noted that intra-tumoral administration can provide direct access to tumor tissue and be beneficial in reducing side effects.

Accordingly, the pharmaceutical composition comprising the oncolytic virus according to the invention is suitable for all forms of administration, including intra-tumoral, intravenous and parenteral administration, alone or in combination with additional delivery agents (e.g. cells or liposomes).

The oncolytic virus pharmaceutical compositions may also comprise pharmaceutically acceptable excipients for providing desirable pharmaceutical or pharmacodynamic properties, such as improved stability, rate of dissolution, and immediate or modified release into an the subject.

The oncolytic EHDV-TAU virus according to the present invention is useful in methods of treating cancer either as a single agent or in combination with other forms of therapy. Accordingly, the method of the invention further comprises administering to the subject a second cancer therapy that can be selected from is selected from virotherapy with other virus, chemotherapy, radiotherapy, immunotherapy, biological therapy, anti-angiogenic therapy, hormone therapy, antivascular therapy, therapy with cytostatic agents, therapy with epigenetics modifying agents, cryotherapy, toxin therapy and surgery, including combinations thereof. Thus, the modified EHDV-TAU according to the invention is suitable for combination therapy with other agents, such as other viruses, cytostatic agents, epigenetics modifying agents, chemical modifying agents of the interferon response, anti-angiogenic or immune therapies in patients with cancer.

In another aspect, the present invention relates to a cell infected ex-vivo with the oncolytic EHDV-TAU virus of the invention, or its products, for preventing or treating cancer, by administering the cell to a subject by any of the administration routes described above.

In one embodiment, the cell for ex-vivo infection is derived from a cancer tissue of a subject and is administered after infection to the same subject.

Specifically, the present invention relates to an adapted viral strain which has undergone the process of in-vitro evolution through serial passaging on LNCaP prostate cancer cell line. The serial passaging process involved the selection of individual viral plaques presenting the characteristics of increased effectiveness of infection/cell killing. The resulting virus strain was named EHDV-TAU-LNCaP. The segmented genome of EHDV-TAU-LNCaP, produced by the in-vitro selection process, is shown in SEQ ID NO: 3.

Accordingly, the invention provides an adapted oncolytic virus, termed EHDV-TAU-LNCaP, comprising the RNA sequence set forth in SEQ ID NO: 3.

EHDV-TAU-LNCaP that is obtained after serially passaging EHDV2-IBA in LNCaP cells for 16 times is characterized by several mutations compared to the original sequence of EHDV2-Ibaraki as shown in SEQ ID NO: 1. These mutations include at least the following nucleotide changes at the indicated positions of SEQ ID NO: 1:

Point Mutations:
Segment 1: T2666C, G3713A and G3888A
Segment 2: C3953T and A4893G
Segment 3: A7024G
Segment 5: A11751G
Segment 7: T16056C and G16094A
Segment 10: G18617A and G18920A
Deletions:
Segment 3: 6984-6989 CTACAC
Segment 6: 14526 G and 14618 G
Insertions:
Segment 6: 14519 G and 14608 G.

Accordingly, the sequence of the oncolytic EHDV-TAU virus comprises the at least the following mutations compared to the sequence of Epizootic Hemorrhagic Disease Virus 2-Ibaraki (EHDV2-Ibaraki) of SEQ ID NO: 1:

(i) point mutations at T2666C, G3713A, G3888A, C3953T, A4893G, A7024G, A11751G, T16056C, G16094A, G18617A and G18920A of SEQ ID NO: 1;
(ii) deletion of CTACAC at positions 6984-6989, deletion of G at position 14526 and deletion of G at position 14618 of SEQ ID NO: 1;
(iii) insertion of G at position 14519 and insertion of G at position 14608 of SEQ ID NO: 1.

However, it should be appreciated that the genome of EHDV-TAU-LNCaP comprises other mutations compared to the original sequence of EHDV2-Ibaraki. Additional, further mutations may occur following infection or serially passaging EHDV2-IBA in LNCaP cells for any number of times other than 16, or serially passaging EHDV2-IBA in any other cell type.

EHDV-TAU-LNCaP has been shown to exhibit the following features:

1. Dramatic increase in its titer compared to the parental strain (the Epizootic Hemorrhagic Disease Virus 2-Ibaraki strain) upon infection of LNCaP prostate cancer cell line.
2. Selectivity towards transformed human cell lines, namely exhibiting selectivity towards human cancer cell lines, especially those showing alterations in interferon response.
3. In vivo effectivity and safety. Experiments in a syngeneic and immunocompetent mouse model (B16 melanoma subcutaneous tumors in C57bl/6 mice) demonstrated the ability of the virus to inhibit tumor growth and extend mouse survival.

According to one aspect, the present application provides a process for the preparation of a cancer-specific oncolytic virus, having enhanced tropism to a target cancer type. The process comprises infecting human cells with Epizootic Hemorrhagic Disease Virus 2-Ibaraki (EHDV2-Ibaraki), to obtain a cell adapted EHDV2-Ibaraki (EHDV2-IBA) and further modifying EHDV2-IBA to target the specific cancer. Further modifying EHDV2-IBA includes, but is not limited to, a chemical modification, site-directed mutagenesis, in-vitro evolution or any combination thereof.

In one embodiment, the present application provides a process for the preparation of a cancer-specific oncolytic virus, having enhanced tropism to a target cancer type. The process comprises:

infecting human cells with Epizootic Hemorrhagic Disease Virus 2-Ibaraki (EHDV2-Ibaraki), to obtain a cell adapted EHDV2-Ibaraki (EHDV2-IBA); and
serially passaging EHDV2-IBA in vitro in cancer cells exhibiting defects in interferon signaling and/or the innate immune antiviral response.

In one embodiment, the oncolytic virus obtained by the process of the invention is EHDV-TAU-LNCaP, endowed with prostate cancer tropism. The cancer cells used for the preparation of EHDV-TAU-LNCaP is the prostate cancer cell line LNCaP.

In a specific embodiment, the step of serially passaging EHDV2-IBA in vitro in LNCaP cells comprises the steps of:

(i) infecting LNCaP cells by EHDV2-IBA;
(ii) sonicating the infected cells obtained in step (i) to release a viral progeny;
(iii) performing a plaque assay of the viral progeny obtained in step (ii) on naive LNCaP cells;
(iv) selecting and purifying a clonal viral strain from a plaque;
(v) repeating steps (i)-(iv) for between 10-20 times, thereby obtaining EHDV-TAU-LNCaP oncolytic virus.

In a further specific embodiment, step (v) is repeated 16 times.

It should be noted that the present invention further provides additional oncolytic viral strains, which are adapted for targeting a specific cancer. For example, the virus can be passaged in cancer cells of different origins, e.g. interferon-insensitive melanoma cells; and/or LNCaP cells with modified p53 responses (e.g. p53 knockout cells, or LNCaP cells expressing the E6/E7 HPV16 proteins). In addition, oncolytic viruses can be obtained by chemical or genetic modifications of the EHDV2-Ibaraki strain or EHDV2-IBA.

Each oncolytic viral strain of the invention may be designed for specific adaptation to any cancer type, thereby improving the treatment outcome. In one embodiment, the oncolytic viral strain is prepared by in vitro passaging an Ibaraki (IBA) strain of the Epizootic Hemorrhagic Disease virus (EHDV2-IBA) in a cancer cell line.

Accordingly, the present invention further relates to a molecular clone of EHDV-TAU (plasmid based, encoding for 10 dsRNA segments), which is optionally modified by site directed mutagenesis (instead of in-vitro evolution). Specific examples of genetic engineering modifications include, addition of a fluorescent protein for visualization, arming of the virus with immune modifiers (e.g. cytokines), and inactivation of viral proteins that mediate antagonism to anti-viral defenses (e.g. modification of the NS3 or NS4 non-structural viral proteins).

According to another aspect, the present invention provides a chemically modified EHDV-TAU. The virus is modified by chemical conjugation to proteins that form its outer-layers. These modifications may include, but are not restricted to, fluorescent tagging or biochemically active molecules which modify its interaction with cancer cells.

According to a further aspect, the invention provides EHDV-TAU viral strains that underwent ab-initio adaptation to different tumors through directed evolution in presence or absence of chemical modifiers of the interferon response, e.g. JAK inhibitors.

According to a still further aspect, the invention relates to an oncolytic EHDV-TAU virus for ex-vivo uses. In one embodiment, the virus is used to selectively eliminate cancer cells from a population of cells (termed purging). In another embodiment, the oncolytic virus serves as an agent in cell therapy, in which cells are infected in vitro by the virus and then applied to a patient.

In summary, in order to be clinically employable, oncolytic viruses need to discriminate between tumor and non-tumor cells. The fact that EHDV-TAU infection is blocked in non-tumorigenic cells, yet, efficiently kills either tumor cells defective in JAK1 signaling (killing that is accompanied by productive infection) or JAK1-positive tumor cells stimulated with cytokines such as IL-6 (killing that is accompanied by non-productive infection), clearly indicates that EHDV-TAU is as an efficient oncolytic agent for human malignancies.

The following examples, which further describe the invention, are offered by way of illustration and are not intended to limit the invention in any manner.

EXAMPLES

Materials and Methods

Cell culture and viruses—The identity of lymph node carcinoma of the prostate cells (LNCaP, ATCC® CRL-1740™) and castration resistant DU145 prostate cancer cells (ATCC® HTB-81™) was confirmed by short tandem repeat (STR) analysis at the biomedical core facility at the genomic center (Technion, Israel). Non-transformed human telomerase reverse transcriptase (hTERT)-immortalized prostate cancer cells (EP) and Baby Hamster Kidney cells (BHK-21) were also employed for plaque assays. LNCaP cells were cultured in Roswell Park Memorial Institute medium (RPMI 1640) supplemented with 2 mM L-glutamine, 10 mM HEPES, and 1 mM sodium pyruvate. BHK-21 cells were cultured in Modified Eagle's Medium (MEM), supplemented with 2 mM L-glutamine. DU145 cells were grown in Dulbecco's Modified Eagle's Medium (DMEM). Culture media were supplemented with 10% Fetal Calf Serum (FCS) and Penicillin-Streptomycin-Neomycin solution (culture reagents are from Beit Haemek Biological Industries). Cultures were grown at 37° C. and 5% CO2.

Viral infections—hMPV-GFP infections were carried for 6 hours in infection media containing RPMI (LNCaP) or DMEM (DU145) supplemented with 3% Fetal Calf Serum, 5 mM Glutamine and Penicillin-Streptomycin and 0.25 mg/ml Trypsin. To determine titer of hMPV-GFP, LNCaP cells were grown to 70% confluency in a 12-well plate, incubated with serial dilutions of the virus in infection media for 2 hours, prior to incubation of cells in medium supplemented with 10% FCS without trypsin for 24 hours. Cells were subsequently trypsinized, fixed in 2% paraformaldehyde and analyzed by fluorescence-activated cell sorting (FACS) to quantify the total number of GFP-positive cells. EHDV-TAU-LNCaP was generated by serial passaging of EHDV2-Ibaraki isolate on LNCaP cells for 16 times. Each of the 16 repetitions included: (i) infection of LNCaP cells; (ii) lysis of infected cells by sonication; (iii) plaque assay of the viral progeny on naive LNCaP cells; (iv) plaque-purification of the virus from largest plaques, for re-infection of LNCaP cells. GFP-expressing, VSV-G-pseudotyped-HIV-based vector (HIV-GFP) was also employed. Handling of all viruses was according to safety regulations of the Tel Aviv University.

Plaque assay—EHDV-TAU-LNCaP or EHDV2-Ibaraki were collected from infected LNCaP cell cultures (medium+cells). Virus was released from attached and detached cells by sonication. Serial dilutions were used to infect reporter cultures ($5\times10^5$ BHK cells/well; seeded in 12-well plates). One well was left uninfected as control. Plates were incubated with virus at 37° C. for 1 hour, after which the cells were washed and overlaid with 0.3% tragacanth (Sigma-Aldrich, cat. #G1128, St. Louis, Mo., USA) in MEM. After 4 days, cultures were fixed and stained with crystal violet (Sigma-Aldrich, cat. #C0775,St. Louis, Mo., USA)/formaldehyde. Virus titer (PFU/ml) was calculated according to number of plaques and dilution factor.

Antibodies—Anti-NS3 antibodies were previously described. Rabbit anti-phospho-Tyr701-STAT1, rabbit anti-STAT1, rabbit anti-phospho-Tyr690-STAT2, rabbit anti-phospho-N F-κB p65 (Ser 536) and rabbit anti-NF-κB p65, diluted 1:1000 for western blot and 1:200 for immunofluorescence, were from Cell Signaling (Beverly, Mass., USA). Rabbit anti-STAT2 (1:1000), rabbit anti-phospho-Tyr705-Stat3 (1:1000), mouse anti-STAT3 (1:1000), and rabbit anti-SOCS3 (1:1000) were from Cell Signaling. Mouse anti-phopho-ERK1/2 (Sigma-Aldrich; 1:500), rabbit anti-ERK1/2 (Santa-Cruz Biotechnology, 1:10000), rabbit-anti-JAK1 (Santa-Cruz Biotechnology, 1:400), rabbit anti-GAPDH (Abcam, 1:5000), mouse anti-GFP (MBL, 1:1000), HRP-conjugated secondary antibodies (Jackson ImmunoResearch Laboratories, cat. #115035003; 1:15000). Mouse anti-Actin, diluted 1:10000, was from MP Biomedicals (Santa Ana, Calif., USA, cat. #69100). Mouse anti-tubulin-α, diluted 1:1000, was from Biolegend (San Diego, Calif., USA, cat. #625901). Alexa-488 and Alexa-555 conjugated secondary antibodies, diluted 1:200, were from ThermoFisher (cat. #A27039 and A28175). HRP-conjugated secondary antibodies, diluted 1:15,000, were from Jackson ImmunoResearch Laboratories (West Grove, Pa., USA, cat. #115035003).

Drugs and Reagents—Reagents were employed at the following final concentrations: RG108 (200 μM); 5-Aza-2'-deoxycytidine (SAC, 20 μM); Trichostatin A (TSA, 0.1 μM); all purchased from Sigma-Aldrich (Sigma-Aldrich, St. Louis, Mo., USA, cat. #R8279, A3656 and T8552). Human interferon-α B2 (IFNαB2, 200 U/ml) was from PBL-assay science, Piscataway, N.J., USA, cat. #111051); DAPI (4',6-Diamidino-2-Phenylindole, Dihydrochloride, 1 μg/ml) was from Sigma-Aldrich (St. Louis, Mo., USA, cat. #D9542). Human tumor necrosis factor-α (TNF-α, 10 ng/ml) was from PeproTech NJ, USA, cat. #30001A. Human IL-6 (PeproTech, cat. #200-06), 5 ng/ml unless stated otherwise; human IFNγ (PeproTech, cat #300-02), 25 ng/ml. Quinolyl-valyl-O-methylaspartyl-[-2,6-difluorophenoxy]-methyl ketone (Q-VD-OPh; ApexBio Technology cat. #A1901), 20 μM; JAK inhibitor (Baricitinib, BioVision, cat. #2842), 0.5 μM.

FACS analysis—LNCaP cells, infected and treated with the indicated drugs, were fixed with 2% paraformaldehyde and analyzed by FACS for GFP fluorescence, using a FACSort apparatus (Becton Dickinson). Each independent experiment included also (i) uninfected LNCaP cells for background auto-fluorescence and (ii) hMPV-infected, non-treated LNCaP cells. LNCaP-JAK1 cells, pre-treated or not with 5 ng/ml IL-6 (for 16 hours) and infected (48 hours) with GFP-expressing VSV-G-pseudotyped-HIV (HIV-GFP) particles (Laham-Karam and Bacharach, 2007), were fixed with 2% paraformaldehyde and analyzed by FACS (Becton Dickinson) for GFP fluorescence. Uninfected LNCaP-JAK1 cells were used to determine background auto-fluorescence. Data were analyzed with the FlowJo software (BD Biosciences).

Immunobloting—Cell pellets were lysed in ice-cold RIPA buffer (150 mM NaCl, 1% NP-40, 0.5% deoxycholate, 0.1% sodium dodecylsulfate, 50 mM Tris-HCl pH 8.0) supplemented with protease inhibitor (Complete Protease Inhibitor Cocktail; Roche, cat. #11-697-498) and phosphatase inhibitor (Phosphatase Inhibitor Cocktail 2+3 (Sigma-Aldrich cat. #p5726, p0044) for 30 minutes on ice. Lysates were cleared by centrifugation (15 minutes, 16,000×g, 4° C.). For each lysate, protein concentration was determined using the Pierce BCA Protein Assay Kit (ThermoFisher, cat. #23225). 10-50 μg of protein (depending on experiment) were separated by sodium dodecyl sulfate polyacrylamide gel electrophoresis (SDS-PAGE) through 10% polyacrylamide gels and transferred to an Immobilon-P membrane (Millipore) according to the manufacturer's instructions. Membranes were blocked for 1 hour in TBST buffer (0.05 M Tris-HCl pH 7.5, 0.15 M NaCl, and 0.1% Tween 20) containing 5% milk, and blotted with primary antibodies overnight at 4° C. Secondary antibody linked to horseradish peroxidase was then added for 1 hour. Immunoreactive bands were detected with the Enhanced Chemiluminescence Substrate (Western Lightning Plus-ECL; PerkinElmer, cat. #NEL105001EA).

qRT-PCR—Total RNA was extracted from cells using EZ-RNA kit (Biological Industries, Israel, cat. #20-400-100) according to the manufacturer's instructions. First-strand cDNA synthesis was performed using the iScript cDNA Synthesis Kit (Bio Rad cat. #1708890) according to the manufacturer's instructions, with additional no-RNA control. Real-Time PCR analyses of mRNA levels of the genes of interest, relative to GAPDH mRNA levels were performed in triplicates, using Fast SYBR-green master mix (Applied Biosystems, cat. #4385612) with StepOnePlus Real-Time PCR System (Applied Biosystems, cat. #4376600). Primers were designed to span exon-exon junctions and to produce 80-140 bp amplicons. Gene expression values were calculated based on the comparative threshold cycle method.

The following primers were used:

```
JAK1
                                  (SEQ ID NO: 14)
fw:      5'GGAAGTGCGCTTCTCTG'3,

         (SEQ ID NOs: 14 and 15, respectively)
rev:     5'CTGCATTTATTCAGCTGTCC'3;

STAT1
         (SEQ ID NOs: 16 and 17, respectively)
fw:      5'TTCAGACCACAGACAACCT'3,

rev:     5'CTGTGTTCATCATACTGTCGA'3;

IFIT5
         (SEQ ID NOs: 18 and 19, respectively)
fw:      5'GCACTTTAAACAAGCTCCTCCTA'3,

rev:     5'CCAAGTTTGAGGAACAATGCT'3;
```

-continued

```
IRF7
         (SEQ ID NOs: 20 and 21, respectively)
fw:      5'CCCAGCAGGTAGCATTCCC'3,

rev:     5'GCAGCAGTTCCTCCGTGTAG'3;

SOCS3
         (SEQ ID NOs: 22 and 23, respectively)
fw:      5'GGAGACTTCGATTCGGGACC'3,

rev:     5'GAAACTTGCTGTGGGTGACC'3;

p21
         (SEQ ID NOs: 24 and 25, respectively)
fw:      5'CTGCCCAAGCTCTACCTTCC'3,

rev:     5'CAGGTCCACATGGTCTTCCT'3;

IRF9
         (SEQ ID NOs: 26 and 27, respectively)
fw:      5'TCCTCCAGAGCCAGACTACT'3,

rev:     5'CAATCCAGGCTTTGCACCTG'3;

RIG-I
         (SEQ ID NOs: 28 and 29, respectively)
fw:      5'GACCCTGGACCCTACCTACA'3,

rev:     5'CTCCATTGGGCCCTTGTTGT'3;

MX1
         (SEQ ID NOs: 30 and 31, respectively)
fw:      5'ATCAGCCTGCTGACATTGGG'3,

rev:     5'CCACATTACTGGGGACCACC'3;

DYSP5
         (SEQ ID NOs: 32 and 33, respectively)
fw:      5'GGATCCCTGTGGAAGACAGC'3,

rev:     5'CAGGACCTTGCCTCCCTTTT'3;
and

GAPDH
         (SEQ ID NOs: 34 and 35, respectively)
fw:      5'AGCCACATCGCTCAGACAC'3,

rev:     5'GCCCAATACGACCAAATCC'3.
```

Genomic DNA sequencing—Genomic DNA of LNCaP or DU145 was extracted with GenElute Mammalian Genomic DNA Miniprep Kit (Sigma, cat. #G1N70). Exons 5 and 9 of JAK1 (where the first exon of JAK1 sequence, according to Genbank accession: NM_002227, is counted as 1) were amplified from purified genomic DNA preparations, using the cognate primers as set forth in SEQ ID NOs: 4 and 5 (exon 5) or SEQ ID NOs: 6 and 7 (exon 9) and Phusion High-Fidelity DNA Polymerase (NEB, cat. #M05305). PCR products were separated by electrophoresis in agarose gels and purified using gel extraction kit (Qiagen, cat. #28704). Sequencing of the PCR products was carried out with ABI 3100 Genetic Analyzer machine.

Cloning—total RNA was extracted from DU145 cells or LNCaP cells treated with 5AC and TSA at the concentrations as described above, for 24 hours (this treatment was required to induce JAK1 mRNA to levels sufficient for cloning). cDNA was prepared and amplified with Phusion Polymerase (NEB), with primers flanking JAK1 exon 5 and exon 9 as set forth in SEQ ID NOs: 8 and 9. PCR products were gel-purified using gel extraction kit (Qiagen), and cloned into pJET1.2/blunt vector (CloneJET PCR Cloning Kitl; ThermoFisher, cat. #K1231). Plasmids were purified with GenElute Plasmid Miniprep Kit (Sigma, cat. #PLN10), and inserts were sequenced with the corresponding pJET primers, as set forth in SEQ ID NOs: 12 and 13, with an ABI 3100 Genetic Analyzer machine.

For generating LNCaP-JAK 1 cells, the following primers were used to amplify JAK1 coding sequence: Fw: 5'CTCGTACGCTTAATTAAC-GATGCAGTATCTAAATATAAAAGA'3 (SEQ ID NO: 10), rev: 5'GAGGGGCGGAATTCCGGATCTTATTT-TAAAAGTGCTTCAAAT'3 (SEQ ID NO: 11). PCR product was inserted into the BamHI site of pHR'-CMV-(ires)-neo vector using the Gibson Assembly method (New Englad Biolabs). Insert was sequenced to ensure the absence of mutations.

Microscopy—Images were acquired with a spinning disk confocal microscope (CSU-22 Confocal Head, Yokogawa; Axiovert 200M, Carl Zeiss MicroImaging) under control of SlideBook (Intelligent Imaging Innovations), with 63× oil immersion objective (Plan Apochromat, NA 1.4), Evolve camera (Photometrics) and laser illumination; or 10× air objective (Plan Apochromat, NA 0.25), EZ camera (Photometrics) and illumination with fluorescence lamp.

Live Microscopy—$4\times10^5$ LNCaP cells were plated on a 35 mm tissue-culture plate. 12-16 hours after plating, the cells were treated, or not, with EpMs (with or without IFNα, which was added 4 hours prior to infection) for 24 hours. hMPV-GFP infection was done in a final volume of 2 ml of infection media, supplemented with 50 mM HEPES. The cells were placed in a 37° C. chamber and bright-field and fluorescence images were taken in intervals of 10 minutes during 24 hours after infection. For analysis of GFP signal intensity, images were segmented according to specific GFP-signal intensity (same value for all conditions), and the values obtained were normalized to the number of cells in each timelapse. Analysis was done using the SlideBook (Intelligent Imaging Innovations) software.

Immunofluorescence—DU145 or LNCaP cells were seeded ($5\times10^4$ cells/well) onto glass coverslips placed in a 24-well plate, and were infected, or not, with EHDV-TAU-LNCaP, in the presence or absence of IFNα. At 44 hours post infection (hpi) or 2 hours (for IFNα treatment), cells were washed twice with cold PBS (4° C.), fixed (4% paraformaldehyde for 20 minutes), blocked and permeabilized (PBS 1%/BSA 0.1%/Triton 0.1% (PBS/BSA/T) for 30 minutes), and stained with polyclonal anti-NS3 (1:300 dilution in PBS/BSA/T). Alexa-488 or 555-conjugated goat-anti-rabbit antibodies (1:200 dilution in PBS/BSA/T) were used as secondary antibodies. In order to detect nuclear phosphorylated STAT1, cells were fixed (4% paraformaldehyde for 20 minutes) and permeabilized with ice-cold methanol (10 minutes at −20° C.). Cells were stained with Rabbit-anti phospho-Tyr701-STAT1 (1:100 dilution in PBS/BSA/T) for overnight at 4° C. Mounting was with Fluorescence Mounting Medium (Golden Bridge, Mukilteo, Wash., USA, cat. #E1818).

Trypan blue exclusion assay—$2\times10^5$ LNCaP cells/well in a 12-well plate were infected, or not, under the indicated experimental conditions. For each well, detached and attached cells were collected together and mixed with 0.5% trypan blue at a 1:1 ratio. Cells were classified by trypan blue exclusion by light microscopy. Trypan blue (0.5%) was from Beit Haemek Biological Industries, Israel (cat. #03-102-1B).

Cell proliferation assay—cells were plated for 72 hours in 96-well plate (5000 cells/well; six repetitions for each time point/condition). Cells were fixed (for 2 hours) every 24 hours with 4% formaldehyde, stained with 0.5% Methylene blue in 0.1 M Sodium Borate, and extracted with 0.1 M HCl. Absorbance was measured at 595 nm.

Cell cycle analysis—LNCaP-JAK1 cells, pre-treated (or not) with IL-6 (5 ng/ml, 16 hours) and infected (or not) with EHDV-TAU-LNCaP (48 hours, moi 0.5) were trypsinized, washed with cold phosphate-buffered saline (PBS) and fixed in ice-cold methanol (1 ml, 20 minutes, −20° C.). RPMI (supplemented with 10% FCS, 10 ml) was added post-fixation, after which cells were pelleted, washed twice with cold PBS and re-suspended in PBS supplemented with RNase A (20 μg/ml, 30 minutes). Following additional pelleting, cells were re-suspended in Propidium Iodide (P1) solution (50 μg/ml in PBS) and analyzed by FACS (Becton Dickinson).

Generation of a list of randomized 500 human genes. 19001 protein coding genes were downloaded from the HUGO Gene Nomenclature Committee (HGNC) website to an Excel sheet. The Excel RAND function was used to generate a randomize number for each of the genes, which were then sorted from the smallest to the largest value. The first 500 hundred genes were selected for farther analyses.

Generation of LNCaP-JAK1 cells—Lentiviral particles pseudotyped with the G-protein of the Vesicular Stomatitis Virus (VSV-G), harboring the pHR'-CMV-JAK1-(IRES)-neo lentivector, which encodes for the JAK1 and the neomycin resistance genes, were generated and used for infection. Infected cells were selected with 800 μg/ml G418 (Sigma-Aldrich, cat. #108321-42-2). Individual colonies were expanded and the presence and activity of JAK1 were evaluated by immunoblotting.

Luciferase assay—DU145 and LNCaP cells were co-transfected with pISRE-Luc (Clontech, PT3372-5W) and renilla luciferase plasmid (pRL-TK; Promega, E2241) as control (ISRE-interferon sequence response element). pISRE-Luc contains the firefly luciferase gene under the control of five copies of the ISRE-binding sequence, located upstream of the TATA-like promoter of the herpes simplex virus thymidine kinase. Transfections were carried out with PolyJet In Vitro DNA Transfection Reagent (SignaGen Laboratories, SL100688). Luciferase activity was detected with the Dual-Luciferase Reporter Assay System (Promega, E1910).

Generation of cells depleted for STAT1 or STAT3 expression—The Clustered Regularly Interspaced Short Palindromic Repeats (CRISPR)/CRISPR-associated nuclease (CRISPR/Cas9) system was employed for the knockout of endogenous STAT1 or STAT3 in LNCaP-JAK1 cells. Small guide RNAs (sgRNAs) targeting STAT1 (GAGGTCAT-GAAAACGGATGG), STAT3 (GCAGCTTGACACACGGTACC), or control GFP (GGGCGAGGAGCTGTTCACCG) genes (as set for the in SEQ ID NOs: 36 to 38, respectively) were designed using the crispr.mit.edu web tool and cloned into the BsmBI site of pXPR lenti-CRISPR plasmid (encoding for Puromycin resistance). Lentiviral particles containing the pXPR lentivectors and the above sgRNAs were prepared and used for infection of LNCaP-JAK1 cells. Clones were selected (2 μg/ml puromycin) and the absence of either STAT1 or STAT3 expression was evaluated by immunoblotting.

Stable Isotope Labeling by Amino Acids Analysis (S/LAC)—LNCaP and LNCaP-JAK1 cells were grown in RPMI devoid of lysine and arginine (Thermo, Cat. #A2494401), supplemented with 10% dialyzed FCS (Biological Industries, cat. #04-011-1A) and antibiotics for ten cell divisions (~3 weeks). "Heavy" culture medium was supplemented with $^{13}C_6{}^{15}N_2$-lysine (146 mg/ml, cat. #CNLM-291-H) and $^{13}C_6{}^{15}N_4$-arginine (84 mg/ml cat. #CNLM-539-H) both from Cambridge Isotope Laboratories. "Light" labeled culture medium was supplemented with unmodified lysine and arginine at the same concentrations. To avoid potential bias in the analysis, in any given condition, cultures were labeled with heavy (H) or light (L) amino acids; or with the reciprocal labeling. Each H-L pair was repeated twice. Thus, quantification of each condition was based on four independent replicates. Labeled cells, either treated or untreated, were trypsinized, counted, and washed twice in cold PBS. Samples were digested by trypsin and analyzed by Liquid chromatography tandem-mass spectrometry (LC-MS/MS) on Q Exactive hybrid quadrupole-Orbitrap mass spectrometer (Thermo Scientific). The data were analyzed and quantified with MaxQuant 1.5.2.8, using the human Uniprot database. Proteins were identified with false discovery rate (FDR)<0.01. Proteins that exhibited differential expression ($|Log_2$ ratio$|\geq 1.5$) in at least three out of four replicates, in any given condition, were chosen for further comparisons. Proteomic analysis of the samples was done at the biomedical core facility at the genomic center (Technion, Israel).

Statistical analysis—Data are expressed as means±standard deviation (SD) or means±Standard Error (SE). Significant differences in mean values were assessed by 1-tailed Student's t-test. A value of $p \leq 0.05$ was considered significant. All experiments were repeated at least three times.

Example 1

JAK1 Inactivating Mutations are Present in Subtypes of Prostate Cancers and in LNCaP Cells and Perturb IFN Signaling Due to the central role played by JAK1 in IFN signaling, the prevalence of JAK1 mutations was evaluated in prostate cancer by accessing the cBioPortal database. In a comprehensive TCGA cohort, composed of 333 patient samples, 3% of the samples presented deep deletions in JAK1 (bi-allelic deletion in copy number analysis, CNA), while an additional 10% of the samples presented shallow deletions (in one allele, Table 1). Further classification of this cohort into prostate cancer subtypes, revealed that 90% of the JAK1 deep deletions occurred in the 'ERG fusion' (erythroblast transformation-specific (ETS)-related gene fusion) subtype ($p=4.542e^{-3}$). These data indicate that genetic alterations to JAK1 are present in subtypes of prostate cancer cells.

TABLE 1

The prevalence of different JAK1 genetic contents (ranging from deep deletion to gain) in different subtypes of prostate cancer in a cohort of 333 patients; different shades of grey are indicative of the number of patient samples in a category.

| Tumor Subtype | Deep Deletion | Shallow Deletion | Diploid | Gain |
|---|---|---|---|---|
| 1-ERG | 8 | 15 | 128 | 1 |
| 2-ETV1 | 0 | 5 | 23 | 0 |
| 3-ETV4 | 1 | 2 | 11 | 0 |
| 4-FLI1 | 0 | 0 | 4 | 0 |
| 5-SPOP | 0 | 4 | 33 | 0 |
| 6-FOXA1 | 0 | 1 | 8 | 0 |
| 7-IDH1 | 0 | 0 | 3 | 0 |
| 8-other | 0 | 5 | 81 | 0 |

Figure 1A:
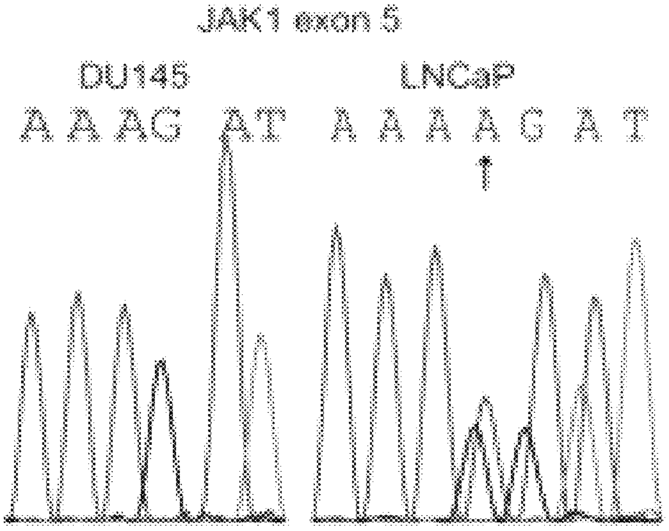
FIGS. 1A-1E show a correlation between deficient expression of Janus kinase 1 (JAK1) and lack of interferon (IFN) signaling in a subset of prostate cancer patient samples and in LNCaP cells.
Figure 1B:
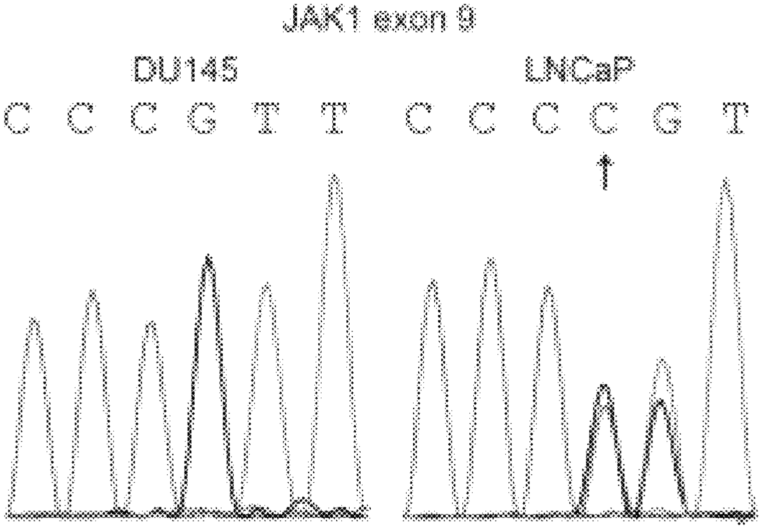

The presence of inactivating mutations was investigated in the genomic DNA of LNCaP and DU145 cells. DU145 is a prostate cancer cell line serving as a positive control due to its sensitivity to IFN. FIGS. 1A and 1B show the presence of the two frameshift mutations in JAK1 gene in LNCaP cells, due to insertions of A and C in exons 5 and 9, respectively. The two mutations are inactivation mutations that reduce the expression of JAK1 mRNA and protein product to below detection threshold. Therefore, LNCaP cells serve as a model system to phenocopy prostate cancers with deep deletions in JAK1.

In order to investigate whether JAK1 expression in LNCaP is also restricted by epigenetic silencing, LNCaP cells were treated by a combination of epigenetic modifiers (EpMs), i.e., 5-Aza -2'-deoxycytidine (5AC) and trichostatin A (TSA). In these treated cells, single JAK1 cDNA molecules amplified by RT-PCR were cloned, and the entire sequence encompassed between exon 5 and exon 9 was determined. These analyses revealed two different mutant JAK1 messages presenting either one of the missense mutations. The presence of two different JAK1 mRNA sequences in LNCaP cells demonstrates lack of physical linkage between the two inactivating mutations, indicating that the mutations are present on different alleles. Notably, spectral karyotyping demonstrated that 4 copies of chromosome 1 (where JAK1 is encoded) are present in LNCaP cells. These data demonstrate that the mutations in JAK1 gene occurred prior to chromosome duplication and that JAK1 inactivation in LNCaP cells emanates from overlapping genetic as well as epigenetic molecular mechanisms.

Figure 1C:
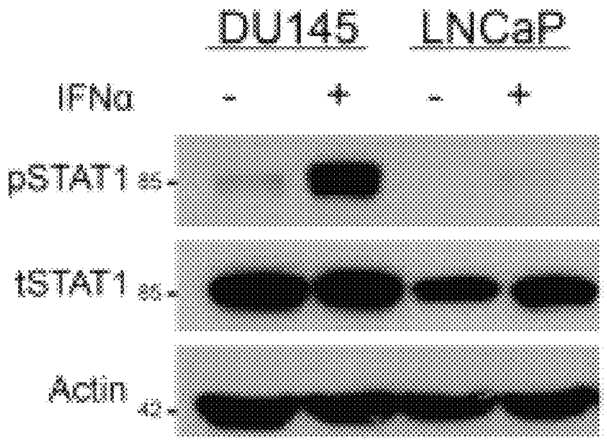
Figure 1D:
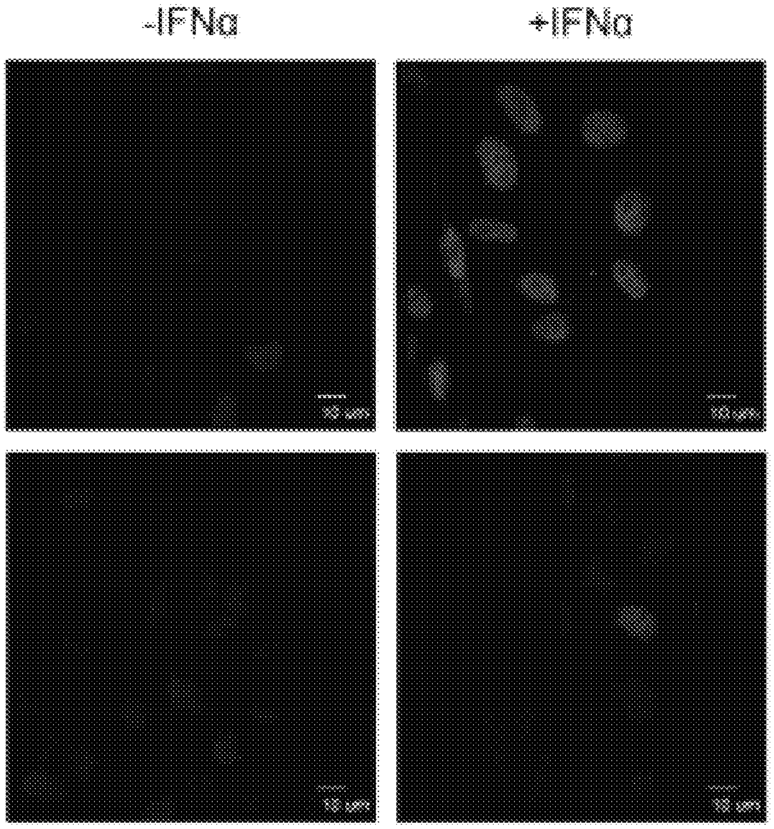
Figure 1E:
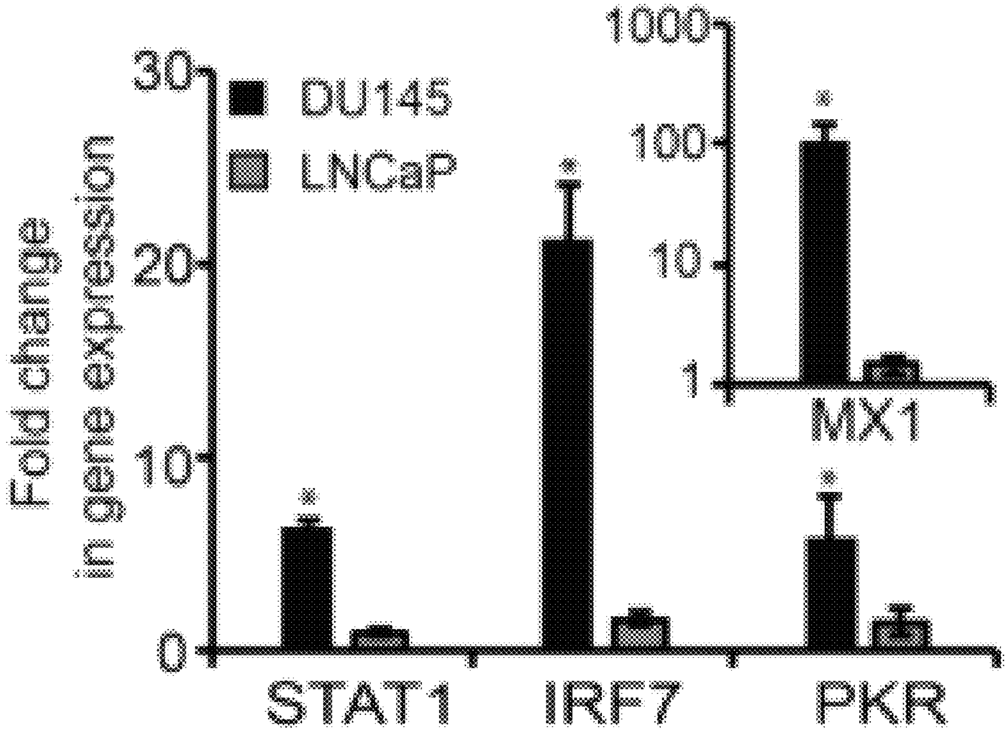

In order to test the consequences of lack of expression of functional JAK1 in LNCaP cells on IFN signaling, LNCaP and DU145 cells were stimulated with IFNα (200 U/ml for 4 hours). Levels of total STAT1 (tSTAT1) and phosphorylated STAT1 (pSTAT1) were analyzed by immunoblotting. FIG. 1C shows robust STAT1 phosphorylation in DU145 cells in response to IFNα, in contrast to only residual pSTAT1 levels in LNCaP cells. Similarly, when pSTAT1 levels were assayed at 30 minutes post stimulation with 200 U/ml IFNα, LNCaP cells exhibited only a 4.2±2.5 fold increase, while the increase in DU145 was much more robust (18±11 fold). Moreover, immunofluorescence analysis with antibodies against pSTAT1 in these cell lines, treated or untreated with IFNα, revealed widespread increase of pSTAT1 levels (glowing signal) and its nuclear localization, only in DU145 cells upon exposure to IFNα (FIG. 1D). Furthermore, prominent transcriptional activation of selected IFN-stimulated genes (ISGs), i.e., STAT1, interferon regulatory factor 7 (IRF7), protein kinase RNA-activated (PKR) and myxoma resistance protein 1 (MX1, also known as interferon-induced GTP-binding protein Mx1), was observed only in DU145 cells, and not LNCaP cells (FIG. 1E). To complement the results showing differential mRNA expression of ISGs in LNCaP and SU145 cells, the response of these cells to IFNα (200 U/ml for 4 hours) was measured with a reporter gene (luciferase) under the control of multiple interferon sequence response elements (ISREs). These experiments (n=2) revealed that prior to IFN stimulation DU145 cells exhibit a 2.4±0.2 fold higher activity of the reporter than LNCaP cells. Stimulation with IFN resulted in only residual (1.2±0.1 fold) activation in the latter cell line. These results confirm the low sensitivity of LNCaP cells to IFN, which correlates with the presence of JAK1 inactivating mutations.

Example 2

Components of the IFN System are Epigenetically Silenced in Prostate Tumors and in LNCaP Cells In order to explore the connection between epigenetic silencing and defective IFN response in prostate cancer patients, the extent of DNA methylation of ISGs in patient samples was estimated. For this purpose, the distribution of β values, representing methylation levels of 500 ISGs and of 500 randomly selected human genes ('random genes data-set'), were analyzed. As shown in FIG. 2A, there is a decrease in the portion of ISGs relative to the random gene dataset at low β values (0<β<0.2), and an increase in the portion of ISGs at β values ranging between 0.5 and 0.8. The increase in β values of the ISGs is indicative of a higher tendency of methylation of these genes, demonstrating that the expression of these genes is negatively regulated by epigenetics. Interestingly, a per-patient correlation of the average β value of the 'random gene data set' and of the ISG data set revealed a positive correlation (R=0.75) between both values (FIG. 2B). These results show that tumors with increased tendency for DNA methylation are characterized by increased methylation of ISGs. In order to estimate the extent of epigenetic silencing of ISGs in LNCaP cells, a list of 500 ISGs was compared with LNCaP-derived gene lists, consisting of 973 genes presenting modified expression following treatment with the DNA methyl transferase inhibitor 5AC and 812 genes with methylated promoters. As shown in FIG. 2C, a subgroup of 21 genes is common to all three categories, indicating that ISGs expression in LNCaP cells is epigenetically suppressed. Further analysis of the data retrieved from cBioPortal revealed deep deletions in several of the 21 gene group (FIG. 2D, black). For example, the ISGs MX1 and MX2 show deep co-deletions in 14% of prostate cancer patients. A probable explanation for the high prevalence of their co-deletion is that both MX1 and MX2 localize to the region between transmembrane protease, serine 2 (TMPRSS2) and ERG on chromosome 21. This region is deleted upon fusion of TMPRS22 and ERG, which is commonly found in prostate cancer. Similarly, the genes epithelial stromal interaction 1 (EPSTI1) and plant homeodomain (PHD) finger protein 11 (PHF11), which are also part of the 21 gene group, localize to chromosome 13 and are co-deleted in ~15% of prostate cancer patients (FIG. 2D). These data show that the interference with expression of ISGs in prostate cancer cells, via genetic and/or epigenetic mechanisms, may be a general feature of this malignancy, and may contribute to both oncogenesis and sensitization of prostate cancer cells to viral infection. These data also highlight LNCaP cells as a good model for prostate tumors, in which combinations of genetic and epigenetics alterations inactivate components of the IFN system.

The extent of methylation in patient-derived samples of the TCGA cohort was also evaluated for JAK1 and correlated to JAK1 expression levels. As control, a similar analysis was performed with the housekeeping gene glyceraldehyde 3-phosphate dehydrogenase (GAPDH). As shown in FIG. 3A, JAK1 exhibited higher levels of methylation than GADPH (β values of 0.78±0.05 for JAK1, as opposed to 0.033±0.006 for GAPDH) and stricter negative correlation between methylation and expression (Pearson's correlation of −0.5 for JAK1, as opposed to −0.2 for GAPDH). These data demonstrate that epigenetic modifications contribute to JAK1 down-regulation in prostate cancer patient samples. In order to probe for the epigenetic silencing of JAK1 in the LNCaP model, the cells were treated with different epigenetic modifiers (EpMs) that target either DNA methylation or histone de-acetylation. Specifically, SAC, RG108 (a specific inhibitor of DNA methyltransferase 1) or were employed. FIG. 3B shows that treatment of LNCaP cells with the EpMs resulted in low but measurable increases in JAK1 mRNA, confirming the contribution of epigenetic modifications to reduced expression of JAK1 message in this cell line. The low expression of JAK1 mRNA (normalized to GAPDH) in LNCaP cells, was further apparent upon the comparison of this normalized expression to the expression observed in DU145 cells (~180 fold higher in DU145, FIG. 3C).

Example 3

EHDV-TAU-LNCaP Successfully Infects LNCaP Cells and Induces Cell Death

The advantages of combining the beneficial features of both reoviruses and veterinary viruses were investigated. The cell-adapted Ibaraki strain of the Epizootic Hemorrhagic Disease virus (EHDV2-IBA) as set forth in SEQ ID NO: 2, which is cytolytic and induces apoptosis, necroptosis, autophagy and cell stress when infecting mammalian cells, was serially passaged in LNCaP cells (as schematically shown in FIG. 4A) in order to optimize its infection abilities of human cancer cells. Indeed, as shown in FIG. 4B, infection of LNCaP cells with the serially passaged virus (denominated 'EHDV-TAU-LNCaP') augmented the fold increase in titer of infected cultures by 6 orders of magnitude, at 60 hours post infection with 0.05 multiplicity of infection (m.o.i). The selectivity of EHDV-TAU-LNCaP to cancer cells was probed by infecting LNCaP cells and the immortalized, non-transformed prostate cells (EP cells) and measuring the synthesis of non-structural proteins as an indicator of productive infection. Infection of LNCaP cells with EHDV-TAU-LNCaP resulted in readily detectable levels of the non-structural protein 3 (NS3), while no NS3 was detected in EP-infected cultures (FIG. 4C). In accordance with the differential susceptibility of the two cell cultures towards EHDV-TAU-LNCaP infection, crystal-violet staining (at 45 hpi) of LNCaP- and EP-cell cultures infected with EHDV-TAU-LNCaP (m.o.i of 0.05) revealed extensive reduction in staining, namely, extensive cell death, of the infected LNCaP culture compared to the non-infected cells (FIG. 4D). By contrast, no reduction in staining was observed in infected EP culture. FIG. 4E shows the differential infection of LNCaP cells and in DU145 cells with EHDV-TAU-LNCaP. Infection of LNCaP cells with EHDV-TAU-LNCaP resulted in ample expression of NS3, while much lesser levels of NS3 were detected in DU145 infected cultures. In order to test whether EHDV-TAU-LNCaP elicits an IFN response in DU145 or LNCaP infected cells, the amount of pSTAT1 in presence or absence of EHDV-TAU-LNCaP infection was measured. EHDV-TAU-LNCaP induced readily detectable levels of pSTAT1 in DU145 cells, while no such signal was observed in the infected LNCaP cell culture. In order to examine whether IFN addition restricts EHDV-TAU-LNCaP infection, the percentage of NS3-positive DU145 or LNCaP infected cells was measured in the presence or absence of IFNα by immunofluorescence microscopy. As shown in FIGS. 4F and 4G, addition of IFNα abrogated the NS3 signal from EHDV-TAU-LNCaP-infected DU145 cultures, while having negligible effects on the infection of LNCaP cells. Taken together, the results indicate that even in the context of prostate cancer cells, EHDV-TAU-LNCaP infection is relatively restricted in cancer cells that retain functional IFN signaling.

Infection of LNCaP cells with EHDV-TAU-LNCaP resulted in a progressive accumulation of dead cells, peaking at ~72 hours. The mechanism of EHDV-TAU-LNCaP-induced death of LNCaP cells was investigated by treating infected cultures with either Q-VD-OPH (pan-caspase inhibitor) or Necrostatin-1 (necroptosis inhibitor). Each of the inhibitors led to a partial reduction in EHDV-TAU-LNCaP-induced cell death (FIG. 5A), indicating that EHDV-TAU-LNCaP kills LNCaP cells by both apoptotic and non-apoptotic pathways. The effects of EpMs and/or IFN on the ability of EHDV-TAU-LNCaP to kill LNCaP cells were then tested. Preliminary experiments demonstrated that the time-frame of the experiment (84 to 96 hours, including pre-treatments and infection), impeded the use of TSA, as it was toxic to LNCaP cells at longer incubation periods (in contrast to 48 hours incubation, as described in Example 2). Addition of IFN alone which was sufficient to significantly protect DU145 cells from death led only to a minimal reduction in EHDV-TAU-LNCaP-induced cell death of LNCaP cells (FIG. 5B). RG108 alone presented a partial protection of LNCaP cells, and this protection was increased upon combination treatment with RG108 and IFNα. 5AC partially sensitized cells to the protective effect of IFNα, as the combination of both agents reduced infection to a greater and significant degree, as compared to IFNα or 5AC alone. Yet, the combined treatment of IFN and 5AC offered a lesser protection to the cells from virus-induced death, compared to the combined treatment of IFNα and RG108. Together, these data demonstrate a mild anti-viral response elicited by EpMs in LNCaP cells, and the increase of such response in presence of IFNα. However, even the most effective anti-viral drug combination (IFN and RG108) did not block virus-induced cell death, but rather reduced it to half of the level observed in untreated, infected cells. The limited extent of the anti-viral effects of EpMs, IFNα or their combination indicates that genetic defects in JAK1/STAT1 signaling plays a prominent role in determining the susceptibility of a subset of prostate cancer cells to virotherapy, even under conditions of combined treatment with EpMs.

Example 4

JAK1 Expression in LNCaP Cells Restores IFNα-Mediated Cell Autonomous Antiviral State LNCaP cells were transduced with a lentivector encoding for JAK1. Single clones, resistant to G418, were selected and probed for JAK1 expression. A representative single clone, denoted LNCaP-JAK1, was selected for following experiments. In accordance with both epigenetic silencing and nonsense-mediated decay of the JAK1 message, JAK1 mRNA levels in LNCaP-JAK1 cells were comparable to the levels observed in DU145 cells, while in parental LNCaP cells, only very low levels of JAK1 mRNA were detected. These results indicated that ectopic expression of JAK1 in the selected colony falls within a physiological range. LNCaP-JAK1, LNCaP or DU145 cells were stimulated with IFNα (200 U/ml for 2 hours), and probed for the levels of tSTAT1, pSTAT1 and actin (as loading control) by immunoblotting. While LNCaP cells were insensitive to IFNα stimuli, LNCaP-JAK1 and DU145 cells showed dramatic increases in pSTAT1 levels upon stimulation (FIG. 6A). A slight IFNα-induced increase in tSTAT1 levels was also observed in LNCaP-JAK1 cells. Of note, IFNα also induced phosphorylation of STAT2. Moreover, qRT-PCR assessment of the levels of expression of two known ISGs, i.e., interferon induced protein with tetratricopeptide repeats 5 (IFIT5) and IRF7, showed a marked induction by IFNα in LNCaP-JAK1, but not in LNCaP cells (FIG. 6B). Moreover, IFNα-induced proteome changes in LNCaP-JAK1 cells, evaluated by stable isotope labeling with amino acids in cell culture (SILAC) analysis combined with mass-spectrometry (MS) and gene-ontology (GO) analysis revealed significant enrichment of ISGs (24.4%, $p<5E^{-10}$) in LNCaP-JAK1 compared to parental LNCaP cells. Together, these data show that ectopic expression of JAK1 restores IFNα signaling and ISG upregulation.

Next, the susceptibility of LNCaP-JAK1 cells to EHDV-TAU-LNCaP viral infection was tested, with or without IFNα treatment. As shown in FIG. 6C, LNCaP cells were highly susceptible to EHDV-TAU-LNCaP infection, as indicated by the high levels of expression and typical smear-like appearance of NS3, irrespective of IFNα treatment. In sharp contrast, infection of untreated LNCaP-JAK1 cells resulted in markedly lower NS3 expression. Baricitinib, a JAK1 inhibitor, fully restored the NS3 expression pattern and levels, to those observed in LNCaP cells. By contrast, IFNα abolished NS3 expression, in accord with a role for JAK1 in the inhibition of EHDV-TAU-LNCaP infection in LNCaP-JAK1 cells. In addition, IFNα inhibited production of infectious virions only in LNCaP-JAK1 cells (FIG. 6D). Moreover, only in IFNα-treated LNCaP-JAK1 cells, protection from EHDV-TAU-LNCaP-induced cell death was observed (FIG. 6E). These results indicate that restoration of JAK1 expression in LNCaP cells is sufficient to restrict productive infection of EHDV-TAU-LNCaP, even more so in presence of IFNα. These data support the specificity of EHDV-TAU-LNCaP towards tumors restricted in interferon-based antiviral responses.

Example 5

EHDV-TAU-LNCaP Induces Oncolysis by Non-Productive Viral Infection

IL-6 is a pleiotropic cytokine that plays key roles in infection and immunity by transducing signals via the JAK/STAT pathway. IL-6 was found to reduce productive EHDV-TAU-LNCaP infection of LNCaP-JAK1 cells, however, visual inspection of these infected cultures suggested massive cell death. In order to quantify this phenomenon, trypan blue exclusion assay was employed. As shown in FIG. 7A, while untreated and uninfected LNCaP-JAK1 cells showed only minimal loss of membrane impermeability (~10%), infection with EHDV-TAU-LNCaP, in the presence or absence of IL-6, resulted in a significant increase in loss of membrane impermeability (~75%). Notably, IL-6 alone had moderate effects on membrane impermeability of LNCaP-JAK1 cells. FIGS. 7B-7D show cell cycle analysis by FACS of cells stained with propidium iodide (PI). As shown in FIG. 7D, IL-6 treatment induced a slight increase in the percentage of cells exhibiting sub-G1 DNA content (namely, cells with fragmented DNA content showing a peak below the G1 peak). EHDV-TAU-LNCaP infection induced a marked increase in sub-G1 fraction. These results indicate that in both productive and abortive infections, EHDV-TAU-LNCaP is capable of inducing apoptosis in LNCaP-JAK1 cells. In order to examine whether caspases are involved in the death induced by the EHDV-TAU-LNCaP and IL-6 combination, caspase activity was blocked with the pan-caspase inhibitor Q-VD-OPh. As shown in FIG. 7E, caspase inhibition reduced the death of EHDV-TAU-LNCaP infected LNCaP-JAK1 cells to basal levels, regardless of the presence of IL-6. This is in conformity with the effect of Q-VD-OPh on cell viability in infections with the parental EHDV2-Ibaraki or with EHDV-TAU-LNCaP infection of LNCaP cells. In order to test whether inhibition of cell death rescues NS3 production in the presence of IL-6 in LNCaP-JAK1 cells, NS3 expression was probed upon exposure of these cells to different combinations of IL-6, Q-VD-OPh and EHDV-TAU-LNCaP. As shown in FIG. 7F, while rescuing cell viability, Q-VD-OPh failed to rescue NS3 expression in EHDV-TAU-LNCaP-infected, IL-6-treated cells. This shows that concerning EHDV-TAU-LNCaP, the IL-6-induced antiviral effect is not dependent on cell death.

To quantify changes in protein expression of LNCaP-based cells upon re-expression of JAK1, cytokine treatment and/or infection, SILAC was applied to cells stimulated with IFNα or IL-6 and infected or not with EHDV-TAU-LNCaP. In repeated experiments (n=4) ~3,800 proteins were identified by LC-MS/MS, of which 2658 proteins were shared by all experiments. 363 proteins of the shared proteins exhibited differential expression (|$Log_2$ ratio|≥0.5) in at least three out of four replicates in any given condition. Summing of the changes in expression for all proteins in each treatment revealed that the most extensive changes occurred for LNCaP-JAK1 cells, treated with IL-6 and infected with EHDV-TAU-LNCaP. Due to the crucial role of ISGs in regulating cellular antiviral state, the analyses was centered on the 50 ISGs products that were identified in the above 363 proteins. as shown in FIG. 8. LNCaP was compared to LNCaP-JAK1 cells, both treated or not with IL-6 (5 ng/ml; for 16 hours). Upon IL-6 treatment, only 3 ISGs were upregulated in LNCaP cells, as opposed to 16 ISGs that were upregulated in LNCaP-JAK1 cells (FIG. 8). This is in accordance with IL-6-mediated phosphorylation of STAT1 and inhibition of viral infection in LNCaP-JAK1 cells, but not LNCaP cells. As both IL-6 and IFNα induced antiviral states in LNCaP-JAK1 cells, the profiles of upregulated ISGs in each condition were compared. IFNα treatment of LNCaP-JAK1 cells induced 17 out of the 50 ISGs. Notably, comparison of these ISGs to the 16 ISGs induced by IL-6, revealed that only five, i.e., interferon induced protein with tetratricopeptide repeats (IFIT) 1, 2 and 3, apolipoprotein L2 (APOL2) and interferon induced with helicase C domain 1 (IFIH1), were common to both conditions. Thus, the two cytokines induce different, but partially overlapping sets of ISGs, correlating with the different sets of STATs activated by these cytokines.

Viral infection modifies the cellular response to cytokine signaling (e.g., through activation of pattern recognition receptors). Hence, the induction of ISGs by EHDV-TAU-LNCaP infection in the absence or presence of IL-6 or IFNα was investigated. EHDV-TAU-LNCaP infection of untreated LNCaP-JAK1 cells induced only two ISGs, namely, 2'-5'-oligoadenylate synthetase 1 (OAS1) and major histocompatibility complex, class I, A (HLA-A). This minimal induction, which failed to block productive infection in these cells, was potentiated by both IL-6 or IFNα, as 27 or 37 ISGs were induced by the combination of EHDV-TAU-LNCaP infection and each of these cytokines, respectively. Analysis of these two sets of ISGs revealed that the majority (20) of ISGs were shared, in accordance with the induction of antiviral state by both cytokines. The 17 ISGs unique to the IFNα+EHDV-TAU-LNCaP condition (IFIH1; TNF receptor associated factor (TRAF)-type zinc finger domain containing 1 (TRAFD1); interferon-induced protein 53 (WARS); negative regulator of ubiquitin like proteins 1 (NUB1); tripartite motif containing 25 (TRIM25); leucine aminopeptidase 3 (LAP3); transporter 1, ATP binding cassette subfamily B member (TAP1); DExD/H-Box Helicase 60 (DDX60); OAS3; guanylate binding protein 1 (GBP1); bone marrow stromal cell antigen 2 (BST2): GBP4, OAS-like (OASL); adenosine deaminase, RNA specific (ADAR): polyribonucleotide nucleotidyltransferase 1 (PNPT1); and OAS2), may contribute to the cytoprotective antiviral-state, induced by IFNα.

Analysis of the 363 proteins with significant changes in expression (in any condition), revealed 71 proteins showing reduced expression ($Log_2$ ratio≤−0.5) in the EHDV-TAU-LNCaP+IL-6 combination. GO annotation (statistical overrepresentation test) of this subset revealed overrepresentation for proteins involved in "DNA metabolic processes" ($p<10^{-8}$), "DNA replication" ($p<10^{-6}$), and "metabolic processes" ($p<10^{-5}$). Remarkably, only seven of these 71 proteins were downregulated in the IFNα+EHDV-TAU-LNCaP condition. Together, these results demonstrate the induction (in JAK1-expressing cells) of ISGs by cytokines (IL-6 and IFNα) and the augmentation of this induction by viral infection. The differences between cytoprotection of infected cells in the presence of IFNα, as opposed to viral-mediated oncolysis in the presence of IL-6 may stem from the down regulation of regulators of cellular metabolism by IL-6 and/or the upregulation of additional ISGs set by IFNα.

Further support for the prominent role of STAT1 activation in the restriction of EHDV-TAU-LNCaP infection in LNCaP-JAK1 cells and in EHDV-TAU-LNCaP induced oncolysis by non-productive infection comes from the observed effects of IFNγ, which are mediated through STAT1 homodimer formation. In LNCaP-JAK1 cells, IFNγ activated STAT1 (but not STAT3) (FIG. 9A), abrogated NS3 production in EHDV-TAU-LNCaP-infected cells (FIG. 9B) and supported oncolysis by non-productive viral infection (FIG. 9C). SILAC analyses of IFNγ-treated LNCaP-JAK1 cells revealed extensive ISGs induction (35 ISGs), demonstrating the ability of STAT1 homodimers to efficiently mediate activation of ISGs expression (FIG. 9D). These experiments demonstrate that STAT1 is necessary for the cell autonomous antiviral effect of IL-6. STAT3 partially contributes to EHDV-TAU-LNCaP-induced oncolysis in the presence of IL-6, which occurs in absence of productive infection.

Together, these results disclose the ability of EHDV-TAU-LNCaP to induce a unique phenomenon denoted "oncolysis by non-productive viral infection (ONPVI)", wherein the infection is carried out in the presence of inflammatory cytokines (e.g., IL-6 or IFNγ), which are predicted to be amply present in the tumor microenvironment. This supports the notion that in a heterogenous tumor, where some cells will be defective in interferon signaling while others will not, EHDV-TAU-LNCaP will be able to exert its anti-tumorigenic effect either by productive infection and killing of cells or by ONPVI.

Example 6

EHDV-TAU-LNCaP Successfully Induces Oncolysis in a B16 Melanoma Model In Vivo As shown in FIG. 10A, 3 successive intra-tumoral injections of EHDV-TAU-LNCaP into B16F10 subcutaneous tumors (employing PBS as a negative control), resulted in a significant reduction in tumor volume at multiple time points. Of note, EHDV-TAU-LNCaP-injected mice showed no weight loss, and remained active throughout the experiment, indicating that EHDV-TAU-LNCaP does not induce deleterious health effects in mice. NS3 protein and viral segements were successfully isolated from the tumors, indicative of productive intra-tumoral infection. FIG. 10C shows data of individual mice. As shown in FIG. 10B, intra-tumoral injection of EHDV-TAU-LNCaP significantly enhanced the survival of mice. Specifically, when tumors reached 1500 $mm^3$, mice were sacrificed according to animal care regulations. The lesser growth of EHDV-TAU-LNCaP infected tumors resulted in prolonged survival of the host animals.

Example 7

EHDV-TAU-LNCaP Induces Immune-Stimulating Secretion by B16 Melanoma Cells

In order to examine the potential of EHDV-TAU-LNCaP infected cells to alter the tumor-microenvironment through secreted factors, the conditioned media of untreated B16-F10 cells (UT), B16-F10 cells infected with UV-inactivated EHDV-TAU-LNCaP (UV) or with replication competent EHDV-TAU-LNCaP (LV) were collected. These conditioned media were used to stimulate freshly isolated bone marrow macrophages. As shown in FIG. 11A, the potential of both "live virus" and UV-inactivated virus to induce immune-stimulating secretion by B16 cells. Differences between UV and LV may stem from either differences in moi or reflect the effect of productive infection on the B16 response.

Next, B16 tumors were surgically excised from C57BL/6 mice, 48 hours after intratumoral injection of PBS (control) or EHDV-TAU-LNCaP, and analyzed for gene expression. Table 2 shows gene ontology analysis (with PANTHER) of genes that showed statistical enrichment in EHDV-TAU-LNCaP sample relative to control. Among the most highly induced genes were lymphocyte antigen 6 complex, locus C2 (Ly6C2), C-C motif chemokine ligand 21 (CCL21), indicating on the presence of lymphocytes, and IFIT1. Moreover, analysis of computational deconvolution of gene expression, aimed at identification of immune cell types identified an increase in effector T cells, a concomitant decrease in naïve/early T cells and an increase in Plasmacytoid Dendritic Cells (FIG. 11B), all in line with intratumoral activation of immune response by EHDV-TAU-LNCaP.

TABLE 2

Gene ontology analysis of genes showing statistical enrichment in EHDV-TAU-LNCaP-infected B16 cells relative to control.

| PANTHER GO-Slim Biological Process | Fold Enrichment | P-Value |
|---|---|---|
| response to interferon-gamma (GO: 0034341) | 11.96 | 4.61E−13 |
| cytokine-mediated signaling pathway (GO: 0019221) | 6.98 | 2.49E−11 |
| immune response (GO: 0006955) | 2.74 | 1.07E−09 |
| cellular defense response (GO: 0006968) | 4.58 | 3.23E−09 |
| immune system process (GO: 0002376) | 3.12 | 4.17E−09 |
| macrophage activation (GO: 0042116) | 6.17 | 2.17E−08 |
| cell-cell adhesion (GO: 0016337) | 4.21 | 3.62E−06 |
| locomotion (GO: 0040011) | 5.02 | 4.47E−06 |

Example 8

EHDV-TAU-LNCaP and EHDV2-IBA are Characterized by Mutations Compared to the Original Sequence of EHDV2 Ibaraki Following deep sequencing of sucrose gradient-purified virions stemming from infection of ovine kidney cells with EHDV2-IBA (IBA) or LNCaP cells with EHDV-TAU-LNCaP (TAU) the different viral strains were analyzed a total of 756,033 (EHDV2-IBA) or 985,924 (EHDV-TAU-LNCaP) reads, which were mapped to the original sequence of EHDV2 Ibaraki (according to Genbank accessions: AM745077-AM745086). As shown in Tables 3 and 4, as well as in FIG. 12, the average coverage (number of reads mapped to the original sequence per position) is 1,993.20 (±1,850.25) and 2,600.06 (±7,050.23) for EHDV2-IBA and EHDV-TAU-LNCaP, respectively. The median coverage is 1,398 and 1,370 for EHDV2-IBA and EHDV-TAU-LNCaP, respectively. In general, positions that are close to the termini of each segment show low coverage. Positions in which a prevalent change in base or codon triplet (compared to the original sequence) were identified in more than 80% of the reads. Positions covered by less than 100 reads were ignored.

TABLE 3

Distribution of the number and types of point mutations found in the genomes of cell adapted EHDV2-Ibaraki (IBA) or EHDV-TAU-LNCaP (TAU)

| | | IBA | | TAU | |
|---|---|---|---|---|---|
| Segment | Product | Total | Non Synonymous | Total | Non Synonymous |
| 1 (3,942 bp) | VP1 | 7 | 6 | 10 | 7 |
| 2 (3,002 bp) | VP2 | 7 | 4 | 8 | 5 |
| 3 (2,768 bp) | VP3 | 3 | 0 | 3 | 0 |
| 4 (1,983 bp) | VP4 | 1 | 0 | 1 | 0 |
| 5 (1,769 bp) | NS1 | 5 | 4 | 6 | 5 |
| 6 (1,641 bp) | VP5 | 5 | 4 | 4 | 3 |
| 7 (1,162 bp) | VP7 | 4 | 1 | 5 | 1 |
| 8 (1,186 bp) | NS2 | 4 | 2 | 4 | 2 |
| 9 (1,074 bp) | VP6, N54 | 6 | 4 | 6 | 4 |
| 10 (810 bp) | NS3 | 2 | 1 | 4 | 3 |
| TOTAL | | 44 | 26 | 51 | 30 |

TABLE 4

Insertion/deletion mutations in EHDV-TAU-LNCaP

| Segment | Type | Sequence Inserted/Deleted | Product |
|---|---|---|---|
| 6 | Insertion | G | VP5 |
| 6 | Deletion | G | VP5 |
| 6 | Insertion | G | VP5 |
| 6 | Deletion | G | VP5 |
| 3 | Deletion | CTACAC | VP3 |

Example 9

EHDV-TAU-LNCaP Infection is Selective Towards Cancer Cells Relative to Non-Transformed Human Cells As shown in FIGS. 13A and 13B, EHDV-TAU-LNCaP preferentially infected and kills HAP1 leukemia cells, while sparing peripheral blood mononuclear cells (PBMCs). In addition, EHDV-TAU-LNCaP failed to productively infect human foreskin fibroblasts (HFF), while eliciting an antiviral-interferon response (FIG. 13C). Furthermore, EHDV-TAU-LNCaP infection resulted in the complete death of the LNCaP culture, while the human immortalized endothelial cells (HMEC), which were rather translucent even without viral infection and thus give a faint signal, maintain viability (FIG. 13D).

Example 10

EHDV-TAU-LNCaP Induces Apoptosis of Human Brain-Metastatic Melanoma Cells and Activates Interferon Signaling Pathways in Brain Microglial Cells A brain-metastatic variant of human melanoma cells (termed YDFR-CB3) were infected with EHDV-TAU-LNCaP. As shown in FIG. 14A, EHDV-TAU-LNCaP infection of YDFR-CB3 cells led to a time- and infection-dependent increase in p53, the non-structural viral protein NS3 and cleaved caspase 3, indicating induction of apoptosis. Accordingly, time-dependent increase in dead cells was observed (FIG. 14B). Moreover, fluorescent imaging of infected YFDR-CB3 cells shows vesiculation of the cell in the context of its lytic death (FIG. 14C).

Next, conditioned media of YDFR-CB3 cells infected with EHDV-TAU-LNCaP were collected and employed to activate immortalized human brain microglia cells. As shown in FIG. 14D, both STAT1 and STAT2 were activated (by phosphorylation) in the stimulated microglia cells indicating that interferon signaling was induced by the conditioned medium.

While the invention has been described using some specific examples, many modifications and variations are possible. It is therefore understood that the invention is not intended to be limited in any way, other than by the scope of the appended claims.

The invention claimed is:

1. A method for treating cancer, comprising:

administering to a subject in need thereof a pharmaceutical composition comprising Epizootic Hemorrhagic Disease virus-Tel Aviv University LNCaP (EHDV-TAU-LNCaP) comprising the RNA sequence set forth in SEQ ID NO: 3, wherein the subject in need thereof is a subject having cancer exhibiting deficient interferon signaling.

2. The method of claim 1, wherein the cancer exhibiting deficient interferon signaling is selected from prostate cancer, melanoma, renal cancer, breast cancer, lung cancer, liver cancer, colorectal cancer, gastric cancer, pancreatic cancer, bladder cancer, glioblastoma, head and neck cancer, myeloma, lymphoma and leukemia.

3. The method of claim 1, wherein the pharmaceutical composition is administered parenterally, intra-tumorally, intradermally, transdermally, intravenously, intramuscularly, intranasaly, subcutaneously, percutaneously, intratracheally, intraperitoneally, intravesically, by inhalation, by perfusion, by lavage, or orally.

4. The method of claim 1, further comprising administering to the subject a second cancer therapy.

5. The method of claim 4, wherein the second cancer therapy is selected from virotherapy with another virus, chemotherapy, radiotherapy, immunotherapy, biological therapy, anti-angiogenic therapy, hormone therapy, anti-vascular therapy, therapy with a cytostatic agent, therapy with an epigenetic modifying agent, cryotherapy, toxin therapy, surgery and a chemical modification of the interferon response.

6. The oncolytic EHDV-TAU-LNCaP virus comprising the RNA sequence as set forth in SEQ ID NO: 3.

7. A cell infected ex-vivo with the oncolytic EHDV-TAU-LNCaP virus of claim 6, for preventing or treating cancer exhibiting deficient interferon signaling.

8. A pharmaceutical composition comprising an effective amount of the oncolytic EHDV-TAU-LNCaP virus of claim 6 and a pharmaceutically acceptable carrier or vehicle, for preventing or treating cancer exhibiting deficient interferon signaling and/or the innate immune antiviral response.

9. The pharmaceutical composition of claim 8 comprising from about $10^1$ pfu to about $1\times10^{15}$ pfu of the oncolytic EHDV-TAU-LNCaP virus.

10. The pharmaceutical composition of claim 8, wherein the composition is formulated for intra-tumoral, intra-venous or parenteral administration, alone or in combination with additional delivery agents.

* * * * *

SEQUENCE LISTING

```
<160> NUMBER OF SEQ ID NOS: 38

<210> SEQ ID NO 1
<211> LENGTH: 19337
<212> TYPE: DNA
<213> ORGANISM: Epizootic hemorrhagic disease virus
<220> FEATURE:
<221> NAME/KEY: misc_feature
<222> LOCATION: (1)..(19337)
<223> OTHER INFORMATION: Epizootic hemorrhagic disease virus, serotype
      2, strain Ibaraki (EHDV2-Ibaraki) RNA consensus sequence
<220> FEATURE:
<221> NAME/KEY: Segment 1
<222> LOCATION: (1)..(3942)
<220> FEATURE:
<221> NAME/KEY: Segment 2
<222> LOCATION: (3943)..(6944)
<220> FEATURE:
<221> NAME/KEY: Segment 3
<222> LOCATION: (6945)..(9712)
<220> FEATURE:
<221> NAME/KEY: Segment 4
<222> LOCATION: (9713)..(11695)
<220> FEATURE:
<221> NAME/KEY: Segment 5
<222> LOCATION: (11696)..(13464)
<220> FEATURE:
<221> NAME/KEY: Segment 6
<222> LOCATION: (13465)..(15105)
<220> FEATURE:
<221> NAME/KEY: Segment 7
<222> LOCATION: (15106)..(16267)
<220> FEATURE:
<221> NAME/KEY: Segment 8
<222> LOCATION: (16268)..(17453)
<220> FEATURE:
<221> NAME/KEY: Segment 9
<222> LOCATION: (17454)..(18527)
<220> FEATURE:
<221> NAME/KEY: Segment 10
<222> LOCATION: (18528)..(19337)
<300> PUBLICATION INFORMATION:
<308> DATABASE ACCESSION NUMBER: AM745077
<309> DATABASE ENTRY DATE: 2009-10-06
<313> RELEVANT RESIDUES IN SEQ ID NO: (1)..(3942)
<300> PUBLICATION INFORMATION:
<308> DATABASE ACCESSION NUMBER: AM745078
<309> DATABASE ENTRY DATE: 2009-10-06
<313> RELEVANT RESIDUES IN SEQ ID NO: (3943)..(6944)
<300> PUBLICATION INFORMATION:
<308> DATABASE ACCESSION NUMBER: AM745079
<309> DATABASE ENTRY DATE: 2009-10-06
<313> RELEVANT RESIDUES IN SEQ ID NO: (6945)..(9712)
<300> PUBLICATION INFORMATION:
<308> DATABASE ACCESSION NUMBER: AM745080
<309> DATABASE ENTRY DATE: 2009-10-06
<313> RELEVANT RESIDUES IN SEQ ID NO: (9713)..(11695)
<300> PUBLICATION INFORMATION:
<308> DATABASE ACCESSION NUMBER: AM745081
<309> DATABASE ENTRY DATE: 2009-10-06
<313> RELEVANT RESIDUES IN SEQ ID NO: (11696)..(13464)
<300> PUBLICATION INFORMATION:
<308> DATABASE ACCESSION NUMBER: AM745082
<309> DATABASE ENTRY DATE: 2009-10-06
<313> RELEVANT RESIDUES IN SEQ ID NO: (13465)..(15105)
<300> PUBLICATION INFORMATION:
```

<308> DATABASE ACCESSION NUMBER: AM745083
<309> DATABASE ENTRY DATE: 2009-10-06
<313> RELEVANT RESIDUES IN SEQ ID NO: (15106)..(16267)
<300> PUBLICATION INFORMATION:
<308> DATABASE ACCESSION NUMBER: AM745084
<309> DATABASE ENTRY DATE: 2009-10-06
<313> RELEVANT RESIDUES IN SEQ ID NO: (16268)..(17453)
<300> PUBLICATION INFORMATION:
<308> DATABASE ACCESSION NUMBER: AM745085
<309> DATABASE ENTRY DATE: 2009-10-06
<313> RELEVANT RESIDUES IN SEQ ID NO: (17454)..(18527)
<300> PUBLICATION INFORMATION:
<308> DATABASE ACCESSION NUMBER: AM745086
<309> DATABASE ENTRY DATE: 2009-10-06
<313> RELEVANT RESIDUES IN SEQ ID NO: (18528)..(19337)

<400> SEQUENCE: 1
gttaaaatgc aatggtcgca attaccgtgc aaggtgcaca gctcattaaa cgagtggttg 60
aaaggatata tcaaggaata acattcgaat tggataatgg catcacagaa ttttataaat 120
tttcagaaca tatcaggcgc ataagagaga aacacggagt gacatataag aggaaagcag 180
aggagataga gcacaacatt aaaatgagga aggaacaact gtttggattg cctgttttac 240
gtgattcaac ttgggaagaa atctttaata ttgactatag agatgatagt gtgatacagg 300
tatacatgaa tgcagtgctg cgccaggaag aattgaatcc ggaggaagaa ttcctgcgaa 360
attataaggt gcaaggcgaa catgctgggt tgacgcaatt tattgagcaa agagcgaaga 420
acgaaatgca aatatatgga gacataccaa tcaaagtttg ggccgccttt ctaattgaac 480
tggattcaga agttaaccac cagagtttag gggtgaaagt catgtcatcg ttcgtcaagc 540
gttatggaga gcctttccat cagggttttc gagatttatc aaacttagaa aggttcaacg 600
tatcatactc aacgccgctg ttgtttgaaa tgtgttgtat ggaatcaata ttagaacata 660
atattataat gcgcatgaag gaggagggag tacacaattt ggagtttggg gatgagaaaa 720
ttgatccaat agcactgttg cgcgaattgt ttattatatg tttgcctcac ccgaagaaaa 780
ttaataatat gttaagatcg ccatattcat ggttcgttaa attatggggg gtgggtgctg 840
accaagttac agtattgacg tcaggtgcag gcgacgatcg taattcgaaa gacgtttttt 900
atgacaaata tcaaacgaat acaaatcgtt acgtcaacat ttttaggtgt aaattctata 960
ctgaatcgca aaaatcgaat tcggagaagg ttgaagaggc gatcctatat tcgcaagaac 1020
tcggaatgca tcattatagc ttacccgtgt ttcaatcaat gttacgaaat gtatatacac 1080 ggcctttttta tccatttaaa caaagtaact tgatgttggc atcttttttg ctaagcttac 1140
aggtaataac aggttatggg cgtgcgtggg tgaaaaacgt tggtacagat ttcgagaagc 1200
agatgaagcc aacgcctgga aatctaatag cggaagtgtc agaacgaacg cgtgaaaact 1260
ttattcaagc ttataatgag gcgagagaaa agagggaaga gatagtgaaa cctgaagatt 1320
tatacacctc tatgctgaga ttggctcgaa atacgagttc aggattcgct gcggagatat 1380
taatacagaa gagatttggt cccaacaaaa gaaaggaatt cgttaaaatt aactcaagaa 1440
tcaaagcggt tgtcattttt acgcgcgggc atatagtttt cacacccgca gagctggaga 1500
agaagtacga tactaccgaa ttgtatcaga ctaagggttc aagggacgtt ccaattaaag 1560
caacacggac gatttactcg ataaatttat cggtattagt tccacagtta atagttacat 1620
tgccattaaa cgaatatttt gcacgagttg gtggaaacac ttcacccgag tataaaaaat 1680
tgggcggtaa aataatagta ggagatctcg aggcgacggg atctcgcgta attgatgcag 1740
cagattgctt cagaaatagc ggtgacaagg atatactcgt tattgctatt gattatagtg 1800
aatacgacac gcatttaact cgctataatt ttcggaaggg catgttagaa ggtattcgtg 1860

```
aagcgatgaa acattataaa gatttgagat atgatggcta cagcgtggat caaataatcg   1920
acttcggata tggcgaagaa cgtgttgcga aaacgctatg gaatggaaaa aggcatgtgt   1980
tcagaactac gttagataaa tatctgagtt tatcggaggc ggagagaata cagggagatt   2040
ttaaaacgcc taagggggta ttgcctgtta caacgataga cgttgcgaag aaaatcgaag   2100
ttagcgataa ttttaacaca ctggtatctg cgacggatgg aagtgacttg gcgttaatcg   2160
atactcactt atcgggcgaa aattcaacat tgatcgctaa ttctatgcat aataaggcta   2220
tcggcggttt aatacagagt gagctgcaaa aagagcacat gcatgatatc actttcctat   2280
cggaacaata tgtgggagat gatacgctat tctattgtaa acttcatact acggatagaa   2340
cgaaggtaca aaaaatgata acaacgattt ttgatacggt agcaaaatgt ggacatgaag   2400
cagcgccgag taaaacgatg ataacgccgt actcggtaga aaagacacaa acgcacgcga   2460
aacaaggtgt gtatgtacca caagatcgaa tgatgattat atcttctgaa cgacgcaaag   2520
acattgaaga tgtgcaaggg tacgttagat cacaggtgca aacaatggta acaaaagtga   2580
gtagaggttt ttgccatgat ttggcgcaaa tgattttaat gctgaaaacg acgtttattg   2640
gggcgtggaa gatgaaacgc actattaagg aaggtggaac atatcgagat cgtaaattcg   2700
actcgaatga agaagacggg tttacgttag taatgttgaa aaacccactt gctctctatg   2760
tgccgatagg gtggaacggt tatggtgcgc atcccgcagc gataaatatc gtcatgacag   2820
aggagatgtt cttagactcg atgtgtattg ggaaactaga tgaaataatg gctcctattt   2880
taaaaattaa aggaaagatc cctcctgcat ggaatgagac gcaagcagac aaacgcgcaa   2940
ttggatctga aacaaagatg gcattcttct ccaaaatggc gcgacccgct gtacaaattg   3000
ctctgaacaa ccgtgaaata atggatgccg tagaacatct acctttagga gatttctcgc   3060
caggacgttt gtctagaaca atgatgcata gtgcgttgct aaaggaatct aaagctcgat   3120
ccttgctagc cgctggatat gaattagact accaaaaatc aattaacgta tggttagaag   3180
atcaagttac ggtagcaatg cgtgaagagc cgggagttat ttcgacgtcc tatgggaagc   3240
tattcgactt atattttgaa gaagatatta tagaggcgcc atacatgttt ccagaccaaa   3300
atttatcgcc tcaattctat atccagaaga tgaagattgg accacgttgt agttcgcgca   3360
tccgtacgtc ttatgttgat aagattgatg ttattttgcg caaggatgta gtaatgcgcg   3420
gatttataac cgctaataca attttgaacg taatagagaa gttgggcacg aatcatactg   3480
cgagtgattt aacgacggta ttcacgttga tgaatattga gaataaagta gcagaggagc   3540
tttcggagta tatcacaagt gagaaaatta ggttcgacgc cttaaagctt ttaaagaaag   3600
gaatcgcggg cgatgaattc actatgtcgc ttgatatagc cacgcaagtt atggttgata   3660
agtatattaa gtatccgcat cagctgacca aaacggagct ggacgcagta gtgttatatt   3720
gttcgcaaat agtgatgttg agagcggcgt gcggactacc attgaagaga atgagattag   3780
ttgttttaga tgaggcaaaa cgacgtttca aagttagagc acagaggttt agaactcaca   3840
taccaagaat taaagtaatt aagaaactca tggatttgaa ccgtatgggt gttcgtcgtc   3900
tagaaaacca attcgtttag agcgcacccg cattacactt acgttaaatt gtccccagaa   3960
tggaggagat ttttataagc gtaattgata gcagtcagcg cgtaccgaaa cagttgtaca   4020
aagattatcc agtaattata gatgtcggac aacggaaagg tgaaaataga ttaccagtgg   4080
aacgattgga aggcaaaaac accatcgaac tgattcaggc agaagcgaga gatttatttc   4140
aatatgactc aaaagatgat tatgagataa tttttccaga tgcgttatca ataggcatac   4200
```

-continued

```
gtcgatatga ctggagacat aaagagttct caaggaatca aaatacaggc gatggtcgcg   4260
gattgatttc atcagatgat gcgtttgaag agttaatgcg tagctcaaat gcaaacgctc   4320
gagtaaaaac ggattttaat gaggagcata ttcatcacga attgtcatat tgtgacgttt   4380
atgtaaatgc gaccatagcg gaaactatag aaattagcgc tcataatagt gaaaagaagg   4440
attgttttca cggtgaagag acggcggtat ataatcatat gctaactgag gcgctatgca   4500
tcgggtcagg aacatgttat gatctggaag aacatgtcca gctcaaaacg atcggggagg   4560
taggcttacg tccacgcgac catgttgatg tttcaggaag aactcatcca aagggagaaa   4620
agatgataac aaggagattc ggaggtggcg agataaagac gctgaccaca agtataaacc   4680
cagatcaatt cgacttaaag aagaagattt ttaatgagga gatcgctatc acggtagaaa   4740
aacgcgactt aattaaatat gatgatgaaa taatgcagct tgatgaaata gctgtaaaat   4800
ggattcggaa tcagaacgcc gatgacctgg aaaaaatcat attattgctg gaagcaatag   4860
gagaaaagga taaacgtgtc gaaccggcta atacagaaga tatccgcaat aaattcaaaa   4920
ggaaattaca ggttaatctc cagaaaacgg atggtgaaat acgaaacata aggaattatc   4980
atcagcatgg tgaaccgaaa cggttggccg caatattaat attaacaatg tgcgacgtaa   5040
tgaaccgtgc catatgggga gataataggt ttaaactagt aagaggagtg tacaattatg   5100
ggaaatatag aatggggtcg gtttatcacg caatgcgaac agatatgatg tggcaactgc   5160
gatcaagtta tctagatacg tgtcctcgta tttgtgatag aagaaaatat ctaatgtacc   5220
gctataatta tttttcttta ggccgggaga cgggagattc tatatataaa tgggacatca   5280
ggactatgcg agacgacaag atgacaacaa gatcaaaggg atggcagtat ggagcaatag   5340
aggatgaaga ggaaagtgat gaagtgttaa tacatgattt tgatgaaggt aaatatgcag   5400
aatatatgca gcggataatt cagggaccat ggattgagaa agatggaatt gggattctaa   5460
tgaaagagca agcagcgatt gagctgtttg attttacgcg ggatgcttat gtagatgaag   5520
cgggtttcct gaggctgccc gcatattaca ataagctaat taaatcaact ttatatgaat   5580
cgtcttttaa ggtaagacgg gtagagatta cgcaaggtaa gagaccagat ccttggaccc   5640
aaaaaacgga ggatgaactg aagaaggaga acgagatgtg gcttttacct gtgtattcag   5700
ttgtggaccg agcgttctgt atgactggca atatattaag cactgcaaaa caggaacaaa   5760
gtgcacggtt tacagccata attgaggctt taaagaaaga gaagagagaa gtacgagaaa   5820
gatattcacg taatgatagt tacacttgcc caatgttaaa cgtatttaat tatacaggat   5880
ataggcagcg aaggttcgtt ttttcaatat taaaaaatca cctgccaaaa tatctactca   5940
tagacatgta cccagatgag gacatagaat acgatcctcg cgattataca gactgtatgg   6000
gaaaagaaga gattttgatg aagatgaaat cgatatttga ggtaatactt tatctaattc   6060
aaataggctt cgaaaaagag gtcgtagttc tgagcgaaga ggagatccgt gtgatgaaac   6120
atagaatgat aaagagagag caccgaaacg acatcatgag tacgcttttg ccggaatttt   6180
cgcggattat aaggagaggc gagaaaatgc aagaggtgga gaagaatgag gacctattac   6240
caatgtattt ctatcaatca ctcattttat caaacgaatt gatatatgaa aacgcgaata   6300
aatcgcatcc agttctcatg ttttgtgaaa aaagagtaag gatcgtccct attcagacga   6360
acgtttggcg aaaagatgtg cctctgcttt cttttctttt tgttttgaaa tatcatgcag   6420
gatggcgaag acgaggtgaa actattgaag aggacgttcg aacagtatgg ccacatttaa   6480
cgaagtattg gttaaatatc gaattcccac gcagggagat caccgattta acgttgatga   6540
gaatgcatcc attgaatacg cattttagca catattgctc gcgtatgtct gaggtatata   6600
```

-continued

```
gttttgcgtt acctatagta catccatcaa aaggtatcgt agttataggt atcattccgg   6660
atactatctc gaatgcccaa ggtttctcgg ttattaaaca aagatttcat tctgttgaac   6720
agtatgtaca tgcgcgaata attttaagag tgttggagaa tggtcacgtg agtgtctacg   6780
gcgatgggga tgtcaagtgt aatttattag agaagttttg ttgcggaagg aagtcgaaga   6840
tcgtaagagt taaactaaat ggaaaagtat acgcgaatcc agaaataatc tcaaaattaa   6900
tgaattaaac ccctgaccgg gtttactggg aacaacaaac ttacgttaaa tttccagagc   6960
gatggcggaa ccaccagatg cggctacacc taaaacaagt ccatatttaa agggagatga   7020
attatcgagc gacagtggcc cattactttc aatattcgct ttacaagaaa taatgcaaaa   7080
agtccgacag gcgcaatccg aatatgtagc agcgacaaaa gatgtcgacc taacaatacc   7140
tgatgttcaa aagataatcg atggagtgaa agagttagct tcagaaacaa tctataaagt   7200
tgtaaacaaa ccactgatat cgtatcgaca tatcgtgatg caatccagag atagattttt   7260
acgggttgat acttattatg aaagaatgtc agaagttggt gacaagatag atgaaaatga   7320
accggctaaa ttttatgaaa ccgtcatcaa gaaagttagg catttaagga ctgaaggcgc   7380
ttttgtttta cacaatatac caactagaga tcatagaggt atggagatag cggacccaga   7440
aattcttggt gttgatgtta agagtatatt gcctgttttg actgcggagc atcgtgctat   7500
ggtgcagcat atattagacg gagcaatcat agaaaacggt aacgttgcga cgcgtgatgt   7560
cgatgtatat ttaggcgctt gttcagagtc tgtatatcgc atatacaatc ggcttcaggg   7620
atatgttgag gcggtacaat tagaggagtt gcgggcggcg atcacgtggc ttgaaagact   7680
ggggagacgt aaacgtatga ccttttcgca ggagtttctc acagacttta gacgagcgga   7740
tacgatatgg gtattagcat tacagttgcc agcaaatccc cgtgtaattt gggatgtacc   7800
tagatgttca atagcaaacc taattatgaa tatagcgacg tgcttaccaa caggagaata   7860
tgtatctcca aatccgcgaa ttgcatcaat aacgcttacc cagagaataa caacgactgg   7920
cccttttgct atcttaactg gatcaactcc aactgctcaa caattagatg atgtgaggaa   7980
gatatattta gcgttaatgt tcccaggtca aataatctta gatttaaaaa tagatccggg   8040
tgagaggatg gacccagcgg tacgtatggt ggcgggggtt gttggtcatt taatgtttac   8100
agcgggacct aggtttacga acataaccca aaatatggca cgacagcttg atattgcctt   8160
agctgatttt cttctctaca tgtacaacac gaggatccag gttcaatatg gtccaacggg   8220
agaaccgcta gatttccgaa taggacgtgg gcagtatgat tgtaacgctt tccgcaccaa   8280
tttccaaact ggtgcgggat ataatggatg gggattagta gatgttgaaa atagagaacc   8340
agcaccatat gatcatgtac aacgctttat acgatattgt aacattgatt ccagagaact   8400
gatacaccca gcgacgttcg gtattggtat gaattattat tgttataacg aaatgttaag   8460
aatgctagtt gctgcaggaa aggatacgga ggcggccttc tttaggaaca tgttaccatt   8520
tcacatggtt agattcgcgc gtataaatca gataatcaac gaggacctac attcggcgtt   8580
ttcgatgcct gatgatcaat ttaatgtatt attagctaat atgatcgcag gcgcgcaaga   8640
aaggatggac cctgtggtat tggatattag ttggatttct atttggtacg cgttcaatcg   8700
atcttttgaa ccaacgcgca gaaatgagat gttagaaagt gcgccgctaa ttgagtctgt   8760
ttatgcgtca gaattgactg ttatgaaaac tgatatgcag cagatggcgt tgttacagcg   8820
tcgcttcccc gatgtgttag ttgaagcgag gccaacgcat ttttggaaag cggtaatgga   8880
ggtatctccg gaaccggtac gtgcaatcat ggatctagcg cattcgcaca gtttcataaa   8940
```

-continued

```
tattcgagat atgatgcgat ggatcggtct accttcaatg cagaactcga tgaagttggt   9000
tttagaagaa gaggcgtggg cggtggctaa tgatttcgaa gaattgatgt taacggatca   9060
agtgtacatg ttccgcgata tgctacctga accaaggtta gatgatattg aaaggttcag   9120
acaagaaggg ttttattaca caaatatgct agatggtcct ccagctatcg atcgagtagt   9180
gcagtataca tatgaagtag caaggttaca agcaaatatg ggtcaattac gggcggcttt   9240
acgaagaatt atggatgacg aaggttgggt taggttcgga ggtgtattaa gaaccgttcg   9300
agttaagttt ttcgattcgc ggccccctga ggagatacta caagcgctgc cgtttgatta   9360
tcagacgagt gagaaaggtg ggctaaccta tgctacgatt aaatatgcta atgacacgac   9420
gatatactac ctgatataca acgtagaata ctcgaatctt ccggattcgt tggtactaat   9480
taatccaacc tacgttatga ccaaggtttt cataaataag cgaatagttg aaagagtacg   9540
ggtgggacaa gcattagcgg ttatgaataa gcgtttcatt gcttataaag ggaagatgcg   9600
tatcatggat attacgcaag cgcttaaggt gggcaccaag ctagcagctc cgaccgtgta   9660
aatatctgcg accaatattt gcaccgagga aaagcactgg aaatacactt acgttaaaac   9720
atgccggagc cacatgcagt gatctatgtt acggaggaat tggtgcacct catcaaggaa   9780
agctatttac cgatttggga gatacggggc gatgaaactc taaatgaact atggctaaca   9840
aacggaaaat attcatcaga tgtatacgcg tatgggaaaa ttaataagtg gagttatcgc   9900
caactacgtg gacatggaat gatattcgta agtactaaga aaatgattca gttaaatgat   9960
gtattaatgt ccgtggatgt caggataccg cgtgaagtga caaagaacat agacgtcaaa  10020
gcattcgaat cgattgttgg gcgcaggaga ttaaaattaa ggaaggcgtt tggcgacatt  10080
ctacgcagct acgcatatag gaaagcgatt gtattacatg gaagtgaagc ggagactcta  10140
aataatgcaa acccgcgatt gcacaaagtt tatgggttac cgaaacagcc accattgtat  10200
tatgagagat taaatgcgga tggccattt atggacgaat ctactgacga gaaattagtt  10260
tcgatgcttg attacgccat ctatagctgt gaagaagtac attatgtagg aagcggggat  10320
ggccgtacgt taatgaattt tgcgaaacga tcaccagagc gtttccatcg aatcatatgg  10380
cacttatatg atccgatcgc taacgatatg aaatacaata acatatatgt tcatcgtacc  10440
tttgttaaca acaagcatga tgtaatgaag aatgtaaatc tattaaaacg agtggagagg  10500
ctgtttattt gggatgtttc aagcgatcgt ggtgacatgg atgacagaca gtgggaaaaa  10560
catagatttg cagaggatag aatgggggaa gagatagcga tgtccatgtc agggttgttc  10620
tcgatggcta taatcaaaca tcgcatacct cagtttatgg atcaatatca cgttgtatct  10680
acatacctaa taccacaacc aggagcgcct acagatatgt atgaattacg gaatattatg  10740
attttgagag gttatagtta tgttgaccga acacgacata ctgatgcaca ggtacacaca  10800
gtggtacaaa gggatgcgtg taaattagtc gagtggtatc atggacgtga aaaaggtaag  10860
aagttgaaga aaatgatttt cgaattctta catatagtcc gcgagaacgg attgtacgca  10920
gaaagtgaag aaccgcgagc ggacttattc tatttgacaa ataaatgcaa ttatgatatg  10980
tggagagagc agaagcgagt tttacggaca agtcaaattg ctacaatgtg ggtgggaggt  11040
gatcaattgt ttgattatga tgactattcg gcgcctcgtg cgttgcttat gctagaatgc  11100
tcgtatcccg atgtacgtat attagatggg aatggagcgg ttctgttttt aatatggaga  11160
tatccagata tttacaaaag aggcttaaat tatgatccca gctgggctat gaaatttgcg  11220
gttacgttaa aggaaccagt ccccgatccg cctgttcctg atatatcact gtgccggttc  11280
atcggactgc gagtcgaatc ctccttaatg agaatacaga atccgagagt tcatcaggtt  11340
```

-continued aacgatgagt taaagcgaat gggattagat gtgtcgggac atctgtatgt cacgttgctg 11400
agtggatcat atgtcacgga tctattgtgg tggtttaaaa tgatattaga gtggtcatca 11460
ttaaacaaaa atgagaagct ggatcaactt aagacatcga aggctgaagt aatcgaatgg 11520
aaggatgaga tggcagaacg gccatggcat gttcgaaatg atctgatagc ggcgctacga 11580
gaattcaaat ataagattca taaacgatgg gatgcaccca ttgagtcgtg gctagattta 11640
ttgcagcgtc tatagaatgt ggtagttctg gactaggcct gcatgttaca cctacgttaa 11700
aaagttcttc gtcgactgcc atcgagatgg agcgcttctt gagaaaatac aacatgaaca 11760
gttattatgc caatcatgtc aaaatgttta aagctttatc gccccagtgg acatgctcgc 11820
atttgagacg gaattgttta tttgatggag tatgtgccaa acagcacttt gaggaagtga 11880
tgaatcgtat aactgagagg aatgatccac atgccgctta taggttagca gaaatggctc 11940
ataatacaat gctggacaga gagaaagtgt ggctgcagtg ctataaaagc ttttcagaac 12000
catatgaaga aaacatagca gagaagattc aaatatgcgg ccgagaactt ttagacaaat 12060
acaaaaatag cgatatggtt acaaaaattg acaacatgat taaatatgac ccaacacgta 12120
ttgtactaaa tgataatttt tcggctttcc catatctata cattccagtc aattacggcc 12180
aaatgattca gccaattaga ataatgaggt ttagacaaat tggatattgc ttttatcagc 12240
cagatgcagc agatgactgg gttgctccag acatatatcc tatgcggaga cctagaatgg 12300
aaatatgccg tcgagtgatg gaagcggttg gaacgtgcgg ctttacagga ttcagtggac 12360
cggtgtttca aattatgttc ctaccaatac agatgctgcc atacatggaa aatgaaggat 12420
ttgccaggat aataaatagg tatgcccaaa tggcagttca gcaatatcta cgagttggat 12480
acatcgagga acgtcggtat gtgactcagt tgtttggaga ttgtccagcg ggagagttcc 12540
ctatgcacag tatgatgctc aggagatggg agaggaatgg gagatcacaa acactggttc 12600
agatgcggca cactatcgct ggaaacaagg agtggcaaac atggttgtta ccaatgatcc 12660
tggtgaggat tgccgtaaga gaaccagcaa attttgaata tgtcagagga tttgtacagg 12720
gcagacacaa atgtcaactg tgcttcctga aaaacggttg tgatcgtcag actttttatc 12780
atatagatgt gaggacatca gagatggtgg gttgtagtac agtgacagat atgatgatcg 12840
atgaacatgt cgacgcgtca ttaccagtgc aaaagatcaa acttaccggg gcagagcatt 12900
taggtcgagc aagtgatcat tatttcaagt ataatgctac aacagggatg gaagcgctga 12960
ttcgcaccgc aatacagatc catcgatggg tgagagggac tggagtgtgg gaaggtgatg 13020
aatggcagga aggggtttat ctgctggcta gggtattact acgttgggaa ttatcatcgc 13080
aggctcgatc tatcatgttc agactttttt gctttgtctg ttttggatat gcgccgcgaa 13140
aagatggaac gataccagat tggaaagatt tgggaacatt tttggatacg gtcctgaacg 13200
gaacggagct ggctgatgat gaagatgaaa cagtgactgg cattatgttt gagctgagcc 13260
gatgcgttat gacgctcgca tatgccgaga aagcgaaagt cgtaactttt aatgttccag 13320
aatgtgatga aggcgcggtt atgaacatcg tacaggcgat ggccaacatg tgggataact 13380
gaaaatgaca cttctttaaa ttacttatcc aaattcaaaa tttcctgaga ttcaattggc 13440
tctccattcg aactttacac ttacgttaaa aaggaggcac gttcttgcat catgggcaag 13500
attatcaaga aattgagcaa ggtaggcaaa aagattggag atgcgttaac atcgaatact 13560
gcgcaacgta tttataaaac aataggaaaa gcagcggaac gttttgcgga gagtgaaatc 13620
ggttcggccg cgattgatgg attgattcaa ggcacagtac aatctgtgat cacgggggag 13680

-continued

```
tcttatggtg aaactgtcaa acaagcggta ttattaaatg tgttgggagc gggagattca  13740
attccagatc ctttaagtcc aggagagcga ggtatgcaag ttaaaatcca agagttagaa  13800
gatgaggaga aaggaaacgc gatacggcaa cggcataatg acagaattat agaactattt  13860
agtaatgatt tagatgatgt gtatcggttc gcaacggcgc aaatcgcaga cgatgagttg  13920
aaagatgatc agtatgaaat tttagagaaa gctgtgaagt cttatggcaa agtgattgga  13980
gaagaggaac gaagattgaa acagctcaga gatgcattac agaaagagat ttcagatagg  14040
agtaaaattg agagagagat ggttgttgaa tatcgtaaca agattgaagc gttacgaggg  14100
gcgatagaaa ttgagtcaga aggtatgcag gaagaagcga tacaggagat tgcaagtatg  14160
agtgctgaca tattagaagc agcgtcagaa gaagttccct tcttcggagc aggcatggcg  14220
accgctatag cttcggcaag ggcggttgaa ggcggctata aactgaagaa agatataaac  14280
gcactgagtg gaatcgattt gagtcacctg aggactccta gaattgaacc tcaaacgctg  14340
gaagtgatcc tacggacacc agtcggtgca gaaattgatg atactaaact agttacaggt  14400
atagcggcga agatcgaggc tatagaagat aatcatcatg aagttgaaca tattgagaag  14460
cagatattac cacaaatcaa acaagctatg aaagaggatc acgaagctat aggaagtgag  14520
agaccgaaga ggattcttcc taaaactgct atgcgattta aagtgccatt aagccagcag  14580
ccacaaattc atatttacgc tgcaccttgg attcagagcg acgtgttcat attgcattgt  14640
gttgcaccac atcatgcgaa tgaatcgttc tttatgggat ttgatctgga gttggagtat  14700
gtattttacg aagatttgac acgtcattgg catgcgctcg gtggtgcaca ggaggcgaca  14760
ggcaggacgt ttcgagaagt ttatcgtgaa ttcttctcat tggctctaca gcaagaaggt  14820
gcgagcgtca tacatcaacg cagattagcg cgttcacgag gtgcgcaccc gatttattta  14880
ggagcgacgc actacgaagt atcatattct cagttgaaac gaaatgcact aaaactagtg  14940
aacgattctg aactgcaggt gcatgtgtta cgaggtccga aacatttcca aagacgtgca  15000
ataatgggtg cgattaaggt aggcctaagc ttaattggag agattgactt gcccgagttt  15060
atgcgttacg cgtgaaggcg gagtacgcga actccttaca cttacgttaa aatttggtga  15120
agatggacac gattgcagca agagctctga cagtcataaa agcttgtaat actttgaaag  15180
aagttagaat agtagtagaa tccaatgtgt tggaaattct tggaatagct attaacagat  15240
ataatgggct aactttgaga tcagtaacca tgcggccaac atcacaggaa caacgaaatg  15300
aaatgttctt tatgtgctta gatatgacgc tggctgcggc gaatttgaat atcggaaaca  15360
tatctccaga ctacatacaa aatttagcaa caattggggt tttagcgaca cctgaaatac  15420
cttatacaat ggaatcagcg aatgagattg cgaggatgag tggagagaca ggaacgtggg  15480
gaccagatcg ccaaccgttc ggctacttct taacggcagc tgaagttacg caacatggac  15540
gatttaggca acgcgcggga caaaatatca caaccgcggt tgtttcgtca actttggcgc  15600
aagtttcaat gaatgcagga gcgcgtggag atatccaagc gctctttcag aatcagaatg  15660
acccaattat gatttatttt gtttggagaa gaatagggac attttcaagc gcggcgggaa  15720
acgcacagga gacaccacaa ggagtaacat taaatgtggg aggtgtgaat atgagggcag  15780
gagtgatcgt ggcttatgac ggtcaagctc ccgtgaatgt aaacaatccg ggagcgggac  15840
caggtatgat agaaatagaa gtaatctact atttgagttt agataaaaca atgacccagt  15900
atccctcatt acaggcacag atttttaacg tctattcata taaaaatccg ttatggcacg  15960
gtctgcgggc ggcaatactc aacagaacaa cattaccgaa taatatccca ccaatatatc  16020
cacctaatga tcgtgaaaat gtcttattgc tgatattact ttcagctcta gcagatgctt  16080
```

-continued

```
ttagcgtact ggcgccagat tttaatctat tcggcgttgt accgatacaa ggtccaataa  16140
acagagctgt tgctcaaaac gcctatgtgt gagggctgtt atggcacggc ataacgctca  16200
catacgcccg tgtcattgtc gtggataacg ggtcatccat ttgcacgtct tcccaaattc  16260
aacttacgtt aaaaattcct tgtgcaatgg agcaaaagca aaggagattt acaaagaacg  16320
tattcgttct agatcaaaag cgaaaaacaa tatgtggtca aattgcatca aagaatgctc  16380
aaccttattg tcaaatcaaa attggaagaa atttcgcatt aaaagcggtg ccaacaccgg  16440
aaccaaaggg gtacgtttta gagattagtg aagttggttc gtatcgcatt caggatggca  16500
gtgatattat tagtctgatg atatcggcgg acggagttga agcaacgaca gagcgatggg  16560
aagaatggaa atttgagacg atctcgtgta ttccaatggc taccgtattg aatattaatg  16620
gtgctctaat tgatgcggag attaaaatat cgaaggggat gggcatggta ccaccgtaca  16680
caaggaatga ttttgacaga cgggagatgc cggaattacc cggcgttcaa aagtcaaaat  16740
atgatgtaaa agaattacgc caaaaaatca gagaagaacg tgaaaaagga aatgttgaat  16800
tacagcctaa gccaacgttt aaagcggaac gttggcatga acagcccgat tccgatgagg  16860
atcaaaatcc aatgaatcag gtggcagatg attgggcaga ggaggttcga aaacaagatg  16920
aggacgctgc gcgccgtaaa gcgttagaaa ctaaattgga ggaacagaga cgaagatatg  16980
aggcatttaa gatggagaat agaaggcaac aggaggaatt taagaaaacg tcagaggaac  17040
caaaagaaat gagagatcgg aagaaggagc cacagctaga agaggttatt gtcgaagatg  17100
aaggagaaga atctggtgag gaagagaccg ttagcgcatc gtacattacg tctaactata  17160
tagagcgcat aagtaaaatt cgaaaatcaa aagatgaacg attgtcaatg ctcgcgagta  17220
tgatgccgca acaggcgggt gaatttacat cgatgctatt caccaagaaa attaaatggg  17280
ataatgttcc gttgtattta atagacgagg ttcagaagaa atatgagtta cagagcgtag  17340
ggggttgtga tcgtgttgcc tttgtctcca aaggcacgaa cctaatcatt ttaccggtag  17400
gcgtctaaac cacgctgatg tagccgcgga caggggaagg gatttacact tacgttaaaa  17460
attgcgcatg tcagctgcgg ttttgctcgc acccggtgac gtgatccaat gttcgaccga  17520
ggaactaaaa caaagacaga tccagattca tttagttgat tgggataagg gagattcaaa  17580
ggaccaaaaa caaacagaac aatcagcgga taaactagat tcacagaagc agaatgagaa  17640
ggagacgcag aaagggagca aaaagggaga gacagatgag aaagatgcaa atgaagatga  17700
tgttcgacgc ttggatgcta cagtgggaca tcgaccaagc gataatcgat ctggagaacg  17760
ccagaaggga tctagcgacg gaggaggaag tgagactaag agaggagata gagatgatgc  17820
gtcaggaact ggaagcaatg gggccgatag agggagatgg atagtgggaa gcgaagaaat  17880
cgctcaatgt ctccagaatc ggtacggagt gagcatccct gtatacagag caggagcgac  17940
cggtacgttc ataaacattg agaagtcgct ccagaaggag ctgggtttca cacgtgaaat  18000
gatggcggaa cagacggaag cgctgcgagc tgtgaaggct gagatgaaga agaataaaaa  18060
cgagaaatct aaggacgcac cagcaacgca gaaccccagt tcagagagga aggggaaagg  18120
taggaaagat gataaagaag aagggataga gacagacgag gggatggttg aggtctcatc  18180
ctcaaaacaa acgttaagac tggctgttga agatgttatg agccagaaga aattactatc  18240
tatgataggg ggaggtgaaa gacgtgagga ggccacacgt gcgcgggaga cttcggttat  18300
gttagtttct aactcgaaag atgatgttga acgcgctaca gcatatttta cagctccaac  18360
gggggatact aactggaaag aagttgcacg gcttgccgct aaaagatcaa atatcatggc  18420
```

```
ttacacttca acggaagagg atgttaagaa gagcttcttg cacttgattg atcatctcta  18480

aagggtcagg gctgctgctt catggcacac gcgcaattta aacttacgtt aaaaagagat  18540

cggtaccatg ctatccagat tagtatcggg cacggagaca agaataaaca tgaaacaaag  18600

tgatgagatg agtttagtgc catatcaaga gcatgtaagg ccaccaagtt atgtaccaac  18660

agcgcccacg ccaacatcaa tgccaagggt tgcattggat atactcgaca aggcaatgtc  18720

aaatcaaacg ggtgcaacta tggcgcaaaa agtagagaag gttgcgtatg cgtcatacgc  18780

agaggcgttt agagatgatc tacggttgcg acagataaag aaacgtgtga atgagcaggt  18840

gttgccaaaa atgcgcgtgg agctaacaat gatgaaaaga aaacgtgcaa tggcacatat  18900

gatattgatt atcgctgcgg ttgttgccct aataacctcc gcgagcacac taacgagcga  18960

tttaggaatc attctaaaga atactaccgc aacggaaata atacagaaac agatcaaacc  19020

attttgcgct gcttttggca taataaattt agccgcaacg atgattatga tgtttatggc  19080

gaagaacgaa aaagtaataa gccagcggat tgaccataca agaaaggaga taatgaagaa  19140

agatgcatac aatgaggcgg tgaggatgag tataacggag cttagtgaag tacctttaga  19200

tggatttgac ataccgcctg aactgatcag atagagtggt gcccccaggt taccgtgatg  19260

tgagattggc aggtctcgac atggtgactc ctactgttgt atagcggggg agggtctgcc  19320

gatctcgaca cacttac                                                 19337
```

```
<210> SEQ ID NO 2
<211> LENGTH: 19337
<212> TYPE: DNA
<213> ORGANISM: Artificial Sequence
<220> FEATURE:
<223> OTHER INFORMATION: Cell-adapted EHDV2-Ibaraki (EHDV2-IBA) RNA
      consensus sequence
<220> FEATURE:
<221> NAME/KEY: Segment 1
<222> LOCATION: (1)..(3942)
<220> FEATURE:
<221> NAME/KEY: Segment 2
<222> LOCATION: (3943)..(6944)
<220> FEATURE:
<221> NAME/KEY: Segment 3
<222> LOCATION: (3945)..(9711)
<220> FEATURE:
<221> NAME/KEY: Segment 4
<222> LOCATION: (9712)..(11694)
<220> FEATURE:
<221> NAME/KEY: Segment 5
<222> LOCATION: (11695)..(13463)
<220> FEATURE:
<221> NAME/KEY: Segment 6
<222> LOCATION: (13464)..(15104)
<220> FEATURE:
<221> NAME/KEY: Segment 7
<222> LOCATION: (15105)..(16266)
<220> FEATURE:
<221> NAME/KEY: Segment 8
<222> LOCATION: (16267)..(17452)
<220> FEATURE:
<221> NAME/KEY: Segment 9
<222> LOCATION: (17453)..(18527)
<220> FEATURE:
<221> NAME/KEY: Segment 10
<222> LOCATION: (18528)..(19337)

<400> SEQUENCE: 2

gttaaaatgc aatggtcgca attaccgtgc aaggtgcaca gctcattaaa cgagtggttg     60

aaaggatata tcaaggaata acattcgaat tggataatgg catcacagaa ttttataaat    120

tttcagaaca tatcaggcgc ataagagaga aacacggagt gacatataag aggaaagcag    180
```

-continued

```
aggagataga gcacaacatt aaaatgagga aggaacaact gtttggattg cctgttttac    240
gtgattcaac ttgggaagaa atctttaata ttgactatag agatgatagt gttttacagg    300
tatacatgaa ttcagtgctg cgccaggaag aattgaatcc ggaggaagaa ttcctgcgaa    360
attataaggt gcaaggcgaa catgctgggt tgacgcaatt tattgagcaa agagcgaaga    420
acgaaatgca aatatatgga gacataccaa tcaaagtttg ggccgccttt ctaattgaac    480
tggattcaga agttaaccac cagagtttag gggtgaaagt catgtcatcg ttcgtcaagc    540
gttatggaga gcctttccat cagggttttc gagatttatc aaacttagaa aggttcaacg    600
tatcatactc aacgccgctg ttgtttgaaa tgtgttgtat ggaatcaata ttagaacata    660
atattataat gcgcatgaag gaggagggag tacacaattt ggagtttggg gatgagaaaa    720
ttgatccaat agcactgttg cgcgaattgt ttattatatg tttgcctcac ccgaagaaaa    780
ttaataatat gttaagatcg ccatattcat ggttcgttaa attatggggg gtgggtgctg    840
accaagttac agtattgacg tcaggtgcag gcgacgatcg taattcgaaa gacgtttttt    900
atgacaaata tcaaacgaat acaaatcgtt acgtcaacat ttttaagtgt aaattctata    960
ctgaatcgca aaaatcgaat tcggagaagg ttgaagaggc gatcctatat tcgcaagaac   1020
tcggaatgca tcattatagc ttacccgtgt ttcaatcaat gttacgaaat gtatatacac   1080
ggcctttttta tccatttaaa caaagtaact tgatgttggc atcttttttg ctaagcttac   1140
aggtaataac aggttatggg cgtgcgtggg tgaaaaacgt tggtacagat ttcgagaagc   1200
agatgaagcc aacgcctgga aatctaatag cggaagtgtc agaacgaacg cgtgaaaact   1260
ttattcaagc ttataatgag gcgagagaaa agagggaaga gatagtgaaa cctgaagatt   1320
tatacacctc tatgctgaga ttggctcgaa atacgagttc aggattcgct gcggagatat   1380
taatacagaa gagatttggt cccaacaaaa gaaaggaatt cgttaaaatt aactcaagaa   1440
tcaaagcggt tgtcattttt acgcgcgggc atatagtttt cacacccgca gagctggaga   1500
agaagtacga tactaccgaa ttgtatcaga ctaagggttc aagggacgtt ccaattaaag   1560
caacacggac gatttactcg ataaatttat cggtattagt tccacagtta atagttacat   1620
tgccattaaa cgaatatttt gcacgagttg gtggaaacac ttcacccgag tataaaaaat   1680
tgggcggtaa aataatagta ggagatctcg aggcgacggg atctcgcgta attgatgcag   1740
cagattgctt cagaaatagc ggtgacaagg atatactcgt tattgctatt gattatagtg   1800
aatacgacac gcatttaact cgctataatt ttcggaaggg catgttagaa ggtattcgtg   1860
aagcgatgaa acattataaa gatttgagat atgaaggcta cagcctggat caaataatcg   1920
acttcggata tggcgaagga cgtgttgcga aaacgctatg gaatggaaaa aggcatgtgt   1980
tcagaactac gttagataaa tatctgagtt tatcggaggc ggagagaata cagggagatt   2040
ttaaaacgcc taagggggta ttgcctgtta caacgataga cgttgcgaag aaaatcgaag   2100
ttagcgataa ttttaacaca ctggtatctg cgacggatgg aagtgacttg gcgttaatcg   2160
atactcactt atcgggcgaa aattcaacat tgatcgctaa ttctatgcat aataaggcta   2220
tcggcggttt aatacagagt gagctgcaaa aagagcacat gcatgatatc actttcctat   2280
cggaacaata tgtgggagat gatacgctat tctattgtaa acttcatact acggatagaa   2340
cgaaggtaca aaaaatgata acaacgattt ttgatacggt agcaaaatgt ggacatgaag   2400
cagcgccgag taaaacgatg ataacgccgt actcggtaga aaagacacaa acgcacgcga   2460
aacaaggtgt gtatgtacca caagatcgaa tgatgattat atcttctgaa cgacgcaaag   2520
acattgaaga tgtgcaaggg tacgttagat cacaggtgca aacaatggta acaaaagtga   2580
```

```
gtagaggttt ttgccatgat ttggcgcaaa tgattttaat gctgaaaacg acgtttattg   2640
gggcgtggaa gatgaaacgc actattaagg aaggtggaac atatcgagat cgtaaattcg   2700
actcgaatga agaagacggg tttacgttag taatgttgaa aaacccactt gctctctatg   2760
tgccgatagg gtggaacggt tatggtgcgc atcccgcagc gataaatatc gtcatgacag   2820
aggagatgtt cttagactcg atgtgtattg ggaaactaga tgaaataatg gctcctattt   2880
taaaaattaa aggaaagatc cctcctgcat ggaatgagac gcaagcagac aaacgcgcaa   2940
ttggatctga aacaaagatg gcattcttct ccaaaatggc gcgacccgct gtacaaattg   3000
ctctgaacaa ccgtgaaata atggatgccg tagaacatct acctttagga gatttctcgc   3060
caggacgttt gtctagaaca atgatgcata gtgcgttgct aaaggaatct aaagctcgat   3120
ccttgctagc cgctggatat gaattagact accaaaaatc aattaacgta tggttagaag   3180
atcaagttac ggtagcaatg cgtgaagagc cgggagttat ttcgacgtcc tatgggaagc   3240
tattcgactt atattttgaa gaagatatta taggggcgcc atacatgttt ccagaccaaa   3300
atttatcgcc tcaattctat atccagaaga tgaagattgg accacgttgt agttcgcgca   3360
tccgtacgtc ttatgttgat aagattgatg ttattttgcg caaggatgta gtaatgcgcg   3420
gatttataac cgctaataca attttgaacg taatagagaa gttgggcacg aatcatactg   3480
cgagtgattt aacgacggta ttcacgttga tgaatattga gaataaagta gcagaggagc   3540
tttcggagta tatcacaagt gagaaaatta ggttcgacgc cttaaagctt ttaaagaaag   3600
gaatcgcggg cgatgaattc actatgtcgc ttgatatagc cacgcaagtt atggttgata   3660
agtatattaa gtatccgcat cagctgacca aaacggagct ggacgcagta gtgttatatt   3720
gttcgcaaat agtgatgttg agagcggcgt gcggactacc attgaagaga atgagattag   3780
ttgttttaga tgaggcaaaa cgacgtttca aagttagagc acagaggttt agaactcaca   3840
taccaagaat taaagtaatt aagaaactca tggatttgaa ccgtatgagt gttcgtcgtc   3900
tagaaaacca attcgtttag agcgcacccg cattacactc acgccaaatc gttcccagaa   3960
tggaggagat ttttataagc gtaattgata gcagtcagcg cgtaccgaaa cagttgtaca   4020
aagattatcc agtaattata gatgtcggac aacggaaagg tgaaaataga ttaccagtgg   4080
aacgattgga aggcaaaaac accatcgaac tgattcaggc agaagcgaga gatttatttc   4140
aatatgactc aaaagatgat tatgagataa tttttccaga tgcgttatca ataggcatac   4200
gtcgatatga ctggagacat aaagagttct caaggaatca aaatacaggc gatggtcgcg   4260
gattgatttc atcagatgat gcgtttgaag agttaatgcg tagctcaaat gcaaacgctc   4320
gagtaaaaac ggattttaat gaggagcata ttcatcacga attgtcatat tgtgacgttt   4380
atgtaaatgc gaccatagcg gaaactatag aaattagcgc tcataatagt gaaaagaagg   4440
attgttttca cggtgaagag acagcggtat ataatcatat gctaactgag gcgctatgca   4500
tcgggtcagg aacatgttat gatctggaag aacatgtcca gctcaaaacg atcggggagg   4560
taggcttacg tccacgcgac catgttgatg tttcaggaag aactcatcca aagggagaaa   4620
agatgataac aaggagattc ggaggtggcg agataaagac gctgaccaca agtataaacc   4680
cagatcaatt cgacttaaag aagaagattt ttaatgagga gatcgctatc acggtagaaa   4740
aacgcgactt aattaaatat gatgatgaaa taatgcagct tgatgaaata gctgtaaaat   4800
ggattcggaa tcagaacgcc gatgacctgg aaaaaatcat attattgctg gaagcaatag   4860
gagaaaagga taaacgtgtc gaaccggcta atacagaagg tatccgcaat aaattcaaaa   4920
```

-continued

```
ggaaattaca ggttaatctc cagaaaacgg atggtgaaat acgaagcata aggaattatc   4980
atcagcatgg tgaaccgaaa cggttggccg caatattaat attaacaatg tgcgacgtaa   5040
tgaaccgtgc catatgggga gataataggt ttaaactagt aagaggagtg tacaattatg   5100
ggaaatatag aatggggtcg gtttatcacg caatgcgaac agatatgatg tggcaactgc   5160
gatcaagtta tctagatacg tgtcctcgta tttgtgatag aagaaaatat ctaatgtacc   5220
gctataatta tttttcttta ggccgggaga cgggagattc tatatataaa tgggacatca   5280
ggactatgcg agacgacaag atgacaacaa gatcaaaggg atggcagtat ggagcaatag   5340
aggatgaaga ggaaagtgat gaagtgttaa tacatgattt tgatgaaggt aaatatgcag   5400
aatatatgca gcggataatt cagggaccat ggattgagaa agatggaatt gggattctaa   5460
tgaaagagca agcagcgatt gagctgtttg attttacgcg ggatgcttat gtagatgaag   5520
cgggtttcct gaggctgccc gcatattaca ataagctaat taaatcaact ttatatgaat   5580
cgtcttttaa ggtaagacgg gtagagatta cgcaaggtaa gagaccagat ccttggaccc   5640
aaaaaacgga ggatgaactg aagaaggaga acgagatgtg gcttttacct gtgtattcag   5700
ttgtggaccg agcgttctgt atgactggca atatattaag cactgcaaaa caggaacaaa   5760
gtgcacggtt tacagccata attgaggctt taaagaaaga gaagagagaa gtacgagaaa   5820
gatattcacg taatgatagt tacacttgcc caatgttaaa cgtatttaat tatacaggat   5880
ataggcagcg aaggttcgtt ttttcaatat taaaaaatca cctgccaaaa aatctactca   5940
tagacatgta cccagatgag gacatagaat acgatcctcg cgattataca gactgtatgg   6000
gaaaagaaga gattttgatg aagatgaaat cgatatttga ggtaatactt tatctaattc   6060
aaataggctt cgaaaaagag gtcgtagttc tgagcgaaga ggagatccgt gtggtgaaac   6120
atagaatgat aaagagagag caccgaaacg acatcatgag tacgcttttg ccggaatttt   6180
cgcggattat aaggagaggc gagaaaatgc aagaggtgga gaagaatgag gacctattac   6240
caatgtattt ctatcaatca ctcattttat caaacgaatt gatatatgaa aacgcgaata   6300
aatcgcatcc agttcttatg ttttgtgaaa aaagagtaag gatcgtccct attcagacga   6360
acgtttggcg aaaagatgtg cctctgcttt cttttctttt tgttttgaaa tatcatgcag   6420
gatggcgaag acgaggtgaa actattgaag aggacgttcg aacagtatgg ccacatttaa   6480
cgaagtattg gttaaatatc gaattcccac gcagggagat caccgattta acgttgatga   6540
gaatgcatcc attgaatacg cattttagca catattgctc gcgtatgtct gaggtatata   6600
gttttgcgtt acctatagta catccatcaa aaggtatcgt agttataggt atcattccgg   6660
atactatctc gaatgcccaa ggtttctcgg ttattaaaca aagatttcat tctgttgaac   6720
agtatgtaca tgcgcgaata attttaagag tgttggagaa tggtcacgtg agtgtctacg   6780
gcgatgggga cgtcaagtgt aatttattag agaagttttg ttgcggaagg aagtcgaaga   6840
tcgtaagagt taaactaaat ggaaaagtat acgcgaatcc agaaataatc tcaaaattaa   6900
tgaattaaac ccctgaccgg gtttactggg aacaacaaac ttacgttaaa tttccagagc   6960
gatggcggaa ccaccagatg cggtgcggct aaaacaagtc catatttaaa gggagatgaa   7020
ttgtcgagcg acagtggccc attactttca atattcgctt tacaagaaat aatgcaaaaa   7080
gtccgacagg cgcaatccga atatgtagca gcgacaaaag atgtcgacct aacaatacct   7140
gatgttcaaa agataatcga tggagtgaaa gagttagctt cagaaacaat ctataaagtt   7200
gtaaacaaac cactgatatc gtatcgacat atcgtgatgc aatccagaga tagattttta   7260
cgggttgata cttattatga aagaatgtca gaagttggtg acaagataga tgaaaatgaa   7320
```

-continued

```
ccggctaaat tttatgaaac cgtcatcaag aaagttaggc atttaaggac tgaaggcgct   7380
tttgttttac acaatatacc aactagagat catagaggta tggagatagc ggacccagaa   7440
attcttggtg ttgatgttaa gagtatattg cctgttttga ctgcggagca tcgtgctatg   7500
gtgcagcata tattagacgg agcaatcata gaaaacggta acgttgcgac gcgtgatgtc   7560
gatgtatatt taggcgcttg ttcagagtct gtatatcgca tatacaatcg gcttcaggga   7620
tatgttgagg cggtacaatt agaggagttg cgggcggcga tcacgtggct tgaaagactg   7680
gggagacgta aacgtatgac cttttcgcag gagtttctca cagactttag acgagcggat   7740
acgatatggg tattagcatt acagttgcca gcaaatcccc gtgtaatttg ggatgtacct   7800
agatgttcaa tagcaaacct aattatgaat atagcgacgt gcttaccaac aggagaatat   7860
gtatctccaa atccgcgaat tgcatcaata acgcttaccc agagaataac aacgactggc   7920
ccttttgcta tcttaactgg atcaactcca actgctcaac aattagatga tgtgaggaag   7980
atatatttag cgttaatgtt cccaggtcaa ataatcttag atttaaaaat agatccgggt   8040
gagaggatgg acccagcggt acgtatggtg gcgggggttg ttggtcattt aatgtttaca   8100
gcgggaccta ggtttacgaa cataacccaa aatatggcac gacagcttga tattgcctta   8160
gctgattttc ttctctacat gtacaacacg aggatccagg ttcaatatgg tccaacggga   8220
gaaccgctag atttccgaat aggacgtggg cagtatgatt gtaacgcttt tcgcaccaat   8280
ttccaaactg gtgcgggata taatggatgg ggattagtag atgttgaaaa tagagaacca   8340
gcaccatatg atcatgtaca acgctttata cgatattgta acattgattc cagagaactg   8400
atacacccag cgacgttcgg tattggtatg aattattatt gttataacga aatgttaaga   8460
atgctagttg ctgcaggaaa ggatacggag gcggccttct ttaggaacat gttaccattt   8520
cacatggtta gattcgcgcg tataaatcag ataatcaacg aggacctaca ttcggcgttt   8580
tcgatgcctg atgatcaatt taatgtatta ttagctaata tgatcgcagg cgcgcaagaa   8640
aggatggacc ctgtggtatt ggatattagt tggatttcta tttggtacgc gttcaatcga   8700
tcttttgaac caacgcgcag aaatgagatg ttagaaagtg cgccgctaat tgagtctgtt   8760
tatgcgtcag aattgactgt tatgaaaact gatatgcagc agatggcgtt gttacagcgt   8820
cgcttccccg atgtgttagt tgaagcgagg ccaacgcatt tttggaaagc ggtaatggag   8880
gtatctccgg aaccggtacg tgcaatcatg gatctagcgc attcgcacag tttcataaat   8940
attcgagata tgatgcgatg gatcggttta ccttcaatgc agaactcgat gaagttggtt   9000
ttagaagaag aggcgtgggc ggtggctaat gatttcgaag aattgatgtt aacggatcaa   9060
gtgtacatgt tccgcgatat gctacctgaa ccaaggttag atgatattga aaggttcaga   9120
caagaagggt tttattacac aaatatgcta gatggtcctc cagctatcga tcgagtagtg   9180
cagtatacat atgaagtagc aaggttacaa gcaaatatgg gtcaattacg ggcggcttta   9240
cgaagaatta tggatgacga aggttgggtt aggttcggag gtgtattaag aaccgttcga   9300
gttaagtttt tcgattcgcg gccccctgag gagatactac aagcgctgcc gtttgattat   9360
cagacgagtg agaaaggtgg gctaacctat gccacgatta aatatgctaa tgacacgacg   9420
atatactacc tgatatacaa cgtagaatac tcgaatcttc cggattcgtt ggtactaatt   9480
aatccaacct acgttatgac caaggttttc ataaataagc gaatagttga aagagtacgg   9540
gtgggacaag cattagcggt tatgaataag cgtttcattg cttataaagg gaagatgcgt   9600
atcatggata ttacgcaagc gcttaaggtg ggcaccaagc tagcagctcc gaccgtgtaa   9660
```

-continued

```
atatctgcga ccaatatttg caccgaggaa aagcactgga aatacacgta cgttaaaaca   9720
tgccggagcc acatgcagta atctatgtta cggaggaatt ggtgcacctc atcaaggaaa   9780
gctatttacc gatttgggag atacggggcg atgaaactct aaatgaacta tggctaacaa   9840
acggaaaata ttcatcagat gtatacgcgt atgggaaaat taataagtgg agttatcgcc   9900
aactacgtgg acatggaatg atattcgtaa gtactaagaa aatgattcag ttaaatgatg   9960
tattaatgtc cgtggatgtc aggataccgc gtgaagtgac aaagaacata gacgtcaaag  10020
cattcgaatc gattgttggg cgcaggagat taaaattaag gaaggcgttt ggcgacattc  10080
tacgcagcta cgcatatagg aaagcgattg tattacatgg aagtgaagcg gagactctaa  10140
ataacgcaaa cccgcgattg cacaaagttt atgggctacc gaaacagcca ccattgtatt  10200
atgagagatt aaatgcggat gggccattta tggacgaatc tactgacgag aaattagttt  10260
cgatgcttga ttacgccatc tatagctgtg aagaagtaca ttatgtagga agcggggatg  10320
gccgtacgtt aatgaatttt gcgaaacgat caccagagcg tttccatcga atcatatggc  10380
acttatatga tccgatcgct aacgatatga aatacaataa catatatgtt catcgtacct  10440
ttgttaacaa caagcatgat gtaatgaaga atgtaaatct attaaaacga gtggagaggc  10500
tgtttatttg ggatgtttca agcgatcgtg gtgacatgga tgacagacag tgggaaaaac  10560
atagatttgc agaggataga atgggggaag agatagcgat gtccatgtca gggttgttct  10620
cgatggctat aatcaaacat cgcatacctc agtttatgga tcaatatcac gttgtatcta  10680
catacctaat accacaacca ggagcgccta cagatatgta tgaattacgg aatattatga  10740
ttttgagagg ttatagttat gttgaccgaa cacgacatac tgatgcacag gtacacacag  10800
tggtacaaag ggatgcgtgt aaattagtcg agtggtatca tggacgtgaa aaaggtaaga  10860
agttgaagaa aatgatttc gaattcttac atatagtccg cgagaacgga ttgtacgcag  10920
aaagtgaaga accgcgagcg gacttattct atttgacaaa taaatgcaat tatgatatgt  10980
ggagagagca gaagcgagtt ttacggacaa gtcaaattgc tacaatgtgg gtgggaggtg  11040
atcaattgtt tgattatgat gactattcgg cgcctcgtgc gttgcttatg ctagaatgct  11100
cgtatcccga tgtacgtata ttagatggga atggagcggt tctgtttttta atatggagat  11160
atccagatat ttacaaaaga ggcttaaatt atgatcccag ctgggctatg aaatttgcgg  11220
ttacgttaaa ggaaccagtc cccgatccgc ctgttcctga tatatcactg tgccggttca  11280
tcggactgcg agtcgaatcc tccttaatga gaatacagaa tccgagagtt catcaggtta  11340
acgatgagtt aaagcgaatg ggattagatg tgtcgggaca tctgtatgtc acgttgctga  11400
gtggatcata tgtcacggat ctattgtggt ggtttaaaat gatattagag tggtcatcat  11460
taaacaaaaa tgagaagctg gatcaactta agacatcgaa ggctgaagta atcgaatgga  11520
aggatgagat ggcagaacgg ccatggcatg ttcgaaatga tctgatagcg gcgctacgag  11580
aattcaaata taagattcat aaacgatggg atgcacccat tgagtcgtgg ctagatttat  11640
tgcagcgtct atagaatgtg gtagttctgg actaggcctg catgttacac ctacgttaaa  11700
aagtgcttcg tcgactgcca tcgagatgga gcgcttcttg agaaaataca acatgaacag  11760
ttattatgcc aatcatgtca aaatgtttaa agctttatcg ccccagtgga catgctcgca  11820
tttgagacgg aattgtttat ttgatggagt atgtgccaaa cagcactttg aggaagtgat  11880
gaatcgtata actgagagga atgatccaca tgccgcttat aggttagcag aaatggctca  11940
taatacaatg ctggacagag agaaagtgtg gctgcagtgc tataaaagct tttcagaacc  12000
atatgaagaa aacatagcag agaagattca aatatgcggc cgagaacttt tagacaaata  12060
```

caaaaatagc gatatggtta caaaaattga caacatgatt aaatatgacc caacacgtat 12120
tgtactagat gataattttt cggcttttcc atatctatac attccagtca attacggcca 12180
aatgattcag ccaattagaa taatgaggtt tagacaaatt ggatattgct tttatcagcc 12240
agatgcagca gatgactggg ttgctccaga catatatcct atgcggagac ctagaatgga 12300
aatatgccgt cgagtgatgg aagcggttgg aacgtgcggc tttacaggat tcagtggacc 12360
ggtgtttcaa attatgttcc taccaataca gatgctgcca tacatggaaa atgaaggatt 12420
tgccaggata ataaataggt atgcccaaat ggcagttcag caatatctac gagttggata 12480
catcgaggaa cgtcggtatg tgactcagtt gtttggagat tgtccagcgg gagagttccc 12540
tatgcacagt atgatgctca ggagatggga gaggaatggg agatcacaaa cactggttca 12600
gatgcggcac actatcgctg gaaacaagga gtggcaaaca tggttgttac caatgatcct 12660
ggtgaggatt gccgtaagag aaccagcaaa ttttgaatat gtcagaggat ttgtacaggg 12720
cagacacaaa tgtcaactgt gcttcctgaa aaacggttgt gatcgtcaga ctttttatca 12780
tatagatgtg aggacatcag agatggtggg ttgtagtaca gtgacagaag taatgatcga 12840
tgaacatgtc gacgcgtcat taccagtgca aaagatcaaa cttaccgggg cagagcattt 12900
aggtcgagca agtgatcatt atttcaagta taatgctaca acagggatgg aagcgctgat 12960
tcgcaccgca atacagatcc atcgatgggt gagagggact ggagtgtggg aaggtgatga 13020
atggcaggaa ggggtttatc tgctggctag ggtattacta cgttgggaat tatcatcgca 13080
ggctcgatct atcatgttca gacttttttg ctttgtctgt tttggatatg cgccgcgaaa 13140
agatggaacg ataccagatt ggaaagattt gggaacattt ttggatacgg tcctgaacgg 13200
aacggagctg gctgatgatg aagatgaaac agtgactggc attatgtttg agctgagccg 13260
atgcgttatg acgctcgcat atgccgagaa agcgaaagtc gtaactttta atgttccaga 13320
atgtgatgaa ggcgcggtta tgaacatcgc acaggcgatg gccaacatgt gggataactg 13380
aaaatgacac ttctttaaat tacttatcca aattcaaaat ttcctgagat tcaattggct 13440
ctccattcga actttacact tacgttaaaa aggaggcacg ttcttgcatc atgggcaaga 13500
ttatcaagaa attgagcaag gtaggcaaaa agattggaga tgcgttaaca tcgaatactg 13560
cgcaacgtat ttataaaaca ataggaaaag cagcggaacg ttttgcggag agtgaaatcg 13620
gttcggccgc gattgatgga ttgattcaag gcacagtaca atctgtgatc acgggggagt 13680
cttatggtga aactgtcaaa caagcggtat tattaaatgt gttgggagcg ggagattcaa 13740
ttccagatcc tttaagtcca ggagagcgag gtatgcaagt taaaatccaa gagttagaag 13800
atgaggagaa aggaaacgcg atacggcaac ggcataatga cagaattata gaactattta 13860
gtaatgattt agatgatgtg tatcggttcg caacggcgca aatcgcagac gatgagttga 13920
aagatgatca gtatgaaatt ttagagaaag ctgtgaagtc ttatggcaaa gtgattggag 13980
aagaggaacg aagattgaaa cagctcagag atgcattaca gaaagagatt tcagatagga 14040
gtaaaattga gagagagatg gttgttgaat atcgtaacaa gattgaagcg ttacgagggg 14100
cgatagaaat tgagtcagaa ggtatgcagg aagaagcgat acaggagatt gcaagtatga 14160
gtgctgacat attagaagca gcgtcagaag aagttccctt cttcggagca ggcatggcga 14220
ccgctatagc ttcggcaagg gcggttgaag gcggctataa actgaagaaa gtgataaacg 14280
cactgagtgg aatcgatttg agtcacctga ggactcctag aattgaacct caaacgctgg 14340
aagtgatcct acggacacca gccggtgcag agattgatga tactaaacta gttacaggta 14400

-continued

```
tagcggcgaa gatcgaggct atagaagata atcatcatga agttgaacat attgagaagc  14460
ggatattacc acaaatcaaa caagctatga aagaggatca cgaagctata ggaagtgagg  14520
agaccaagag gattcttcct aaaactgcta tgcgatttaa agtgccatta agccagcagc  14580
cacaaattca tatttacgct gcaccttggg attcagacga cgtgttcata ttgcattgtg  14640
ttgcaccaca tcatgcgaat gaatcgttct ttatgggatt tgatctggag ttggagtatg  14700
tattttacga agatttgaca cgtcattggc atgcgctcgg tggtgcacag gaggcgacag  14760
gcaggacgtt tcgagaagtt tatcgtgaat tcttctcatt ggctctacag caagaaggtg  14820
cgagcgtcat acatcaacgc agattagcgc gttcacgagg tgcgcacccg atttatttag  14880
gagcgacgca ctacgaagta tcatattctc agttgaaacg aaatgcacta aaactagtga  14940
acgattctga actgcaggtg catgtgttac gaggtccgaa acatttccaa agacgtgcaa  15000
taatgggtgc gattaaggta ggcctaagct taattcgaga gattgacttg cccgagttta  15060
tgcgttacgc gtgaaggcgg agtacgcgaa ctccttacac taactatgaa atttggtgaa  15120
aatggacacg attgcagcaa gagctctgac agtcataaaa gcttgtaata ctttgaaaga  15180
agttagaata gtagtagaat ccaatgtgtt ggaaattctt ggaatagcta ttaacagata  15240
taatgggcta actttgagat cagtaaccat gcggccaaca tcacaggagc aacgaaatga  15300
aatgttcttt atgtgcttag atatgacgct ggctgcggcg aatttgaata tcggaaacat  15360
atctccagac tacatacaaa atttagcaac aattggggtt ttagcgacac ctgaaatacc  15420
ttatacaatg gaatcagcga atgagattgc gaggatgagt ggagagacag gaacgtgggg  15480
accagatcgc caaccgttcg gctacttctt aacggcagct gaagttacgc aacatggacg  15540
atttaggcaa cgcgcgggac aaaatatcac aaccacggtt gtttcgtcaa ctttggcgca  15600
ggtttcaatg aatgcaggag cgcgtggaga tatccaagcg ctctttcaga atcagaatga  15660
cccaattatg atttattttg tttggagaag aatagggaca ttttcaagcg cggcgggaaa  15720
cgcacaggag acaccacaag gagtaacatt aaatgtggga ggtgtgaata tgagggcagg  15780
agtgatcgtg gcttatgacg gtcaagctcc cgtgaatgta aacaatccgg gagcgggacc  15840
aggtatgata gaaatagaag taatctacta tttgagttta gataaaacaa tgacccagta  15900
tccctcatta caggcacaga tttttaacgt ctattcatat aaaaatccgt tatggcacgg  15960
tctgcgggcg gcaatactca acagaacaac attaccgaat aatatcccac caatatatcc  16020
acctaatgat cgtgaaaatg tcttattgct gatattactt tcagctctag cagatgcttt  16080
tagcgtactg gctccagatt ttaatctatt cggcgtcgta ccgatacaag gtccaataaa  16140
cagagccgtt gctcaaaacg cctatgtgtg agggctgtta tggcacggca taacgctcac  16200
atacgcccgt gtcattgtcg tggataacgg gtcatccatt tgcacgtttt cccaaattca  16260
acttacgtta aaaatcccct gtgcaatgga gcaaaagcaa aggagattta caaagaacgt  16320
attcgttcta gatcaaaagc gaaaaacaat atgtggtcaa attgcatcaa agaatgctca  16380
accttattgt caaatcaaaa ttggaagaaa tttcgcatta aaagcggtgc caacaccgga  16440
accaaagggg tacgttttag agattagtga agttggttcg tatcgcattc aggatggcag  16500
tgatattatt agtctgatga tatcggcgga cggagttgaa gcaacgacag agcgatggga  16560
agaatggaaa tttgagacga tctcgtgtgt tccaatggct accgtattga atattaatgg  16620
tgctctaatt gatgcggaga ttaaaatatc gaaggggatg ggcatggtac caccgtacac  16680
aaggaatgat tttgacagac gggagatgcc ggaattacct ggcgttcaaa agtcaaaata  16740
tgatgtaaaa gaattacgcc aaaaaatcag agaagaacgt gaaaagggaa atgttgaatt  16800
```

-continued

```
acagcctaag ccaacgttta aagcggaacg ttggcatgaa cagcccgatt ccgatgagga  16860
tcaaaatcca atgaatcaga tggcagatga ttgggcagag gaggttcgaa aacaagatga  16920
ggacgctgcg cgccgtaaag cgttagaaac taaattggag gaacagagac gaagatatga  16980
ggcatttaag atggagaata gaaggcaaca ggaggaattt aagaaaacgt cagaggaacc  17040
aaaagaaatg agagatcgga agaaggagcc acagctagaa gaggttattg tcgaagatga  17100
aggagaagaa tctggtgagg aagagaccgt tagcgcatcg tacattacgt ctaactatat  17160
agagcgcata agtaaaattc gaaaatcaaa agatgaacga ttgtcaatgc tcgcgagtat  17220
gatgccgcaa caggcgggtg aatttacatc gatgctattc accaagaaaa ttaaatggga  17280
taatgttccg ttgtatttaa tagacgaggt tcagaagaaa tatgagttac agagcgtagg  17340
gggttgtgat cgtgttgcct ttgtctccaa aggcacgaac ctaatcattt taccggtagg  17400
cgtctaatcc acgctgatgt agccgcggat aggggaaggg atttacactt acgttacata  17460
tagcgcatgt cagctgcggt tttgctcgca cccggtgacg tgatccaatg ttcggccgag  17520
gaactaaaac aaagacagat ccagattcat ttagttgatt gggataaggg agattcaaag  17580
gaccaaaaac aaacagaaca atcagcggat aaactagatt cacagaagca gaatgagaag  17640
gagacacaga aagggagcaa aaaggaagag acagatgaga aagatgcaaa tgaagatgat  17700
gttcgacgct tggatgctac agtgggacat cgaccaagcg ataaacgatc tggagaacgc  17760
cagaagggat ctagcgacgg aggaggaagt gagactaaga gaggagatag agatgatgcg  17820
tcaggaactg gaagcaatgg ggccgataga gggagatgga tagtgggaag cgaagaaatt  17880
gctcaatgtc tccagaatcg gtacggagtg agcatccctg tatacagagc aggagcgacc  17940
ggtacgttca taaacattga gaagtcgctc cagaaggagc tgggtttcac acgtgaaatg  18000
atggcggaac agacggaagc gctgcgagct gtgaaggctg agatgaagaa gaataaaaac  18060
gagaaatcta aggacgcacc agcaacgcag aaccccagtt cagagaggaa ggggaaaggt  18120
aagaaagatg ataaagaaga agggatagag acagacgagg ggatggttga ggtctcatcc  18180
tcaaaacaaa cgttaagact ggctgttgaa gatgttatga gccagaagaa attactatct  18240
atgatagggg gaggtgaaag acgtgaggag gccacacgtg cgcgggagac ttcggttatg  18300
ttagtttcta actcgaaaga tgatgttgaa cgcgctacag catattttac agctccaacg  18360
ggggatacta actggaaaga agttgcacgg cttgccgcta aaagatcaaa tatcatggct  18420
tacacttcaa cggaagagga tgttaagaag agcttcttgc acttgattga tcatctctaa  18480
agggtccggg ctgctgcttc atggcacacg cgcgatttaa aactcacgat aaaaagagat  18540
cggtaccatg ctatccaggt tagtatcggg tacggagaca agaataaaca tgaaacaaag  18600
tgatgagatg agtttagtgc catatcaaga gaatgtaagg ccaccaagtt atgtaccaac  18660
agcgcccacg ccaacatcaa tgccaagggt tgcattggat atactcgaca aggcaatgtc  18720
aaatcaaacg ggtgcaacta tggcgcaaaa agtagagaag gttgcgtatg cgtcatacgc  18780
agaggcgttt agagatgatc tacggttgcg acagataaag aaacgtgtga atgagcaggt  18840
attgccaaaa atgcgcgtgg agctaacaat gatgaaaaga aaacgtgcaa tggcacatat  18900
gatattgatt atcgctgcgg ttgttgccct aataacctcc gcgagcacac taacgagcga  18960
tttaggaatc attctaaaga atactaccgc aacggaaata atacagaaac agatcaaacc  19020
attttgcgct gcttttggca taataaattt agccgcaacg atgattatga tgtttatggc  19080
gaagaacgaa aaagtaataa gccagcggat tgaccataca agaaaggaga taatgaagaa  19140
```

agatgcatac aatgaggcgg tgaggatgag tataacggag cttagtgaag tacctttaga 19200
tggatttgac ataccgcctg aactgatcag atagagtggt gcccccaggt taccgtgatg 19260
tgagattggc aggtctcgac atggtgactc ctactgttgt atagcggggg agggtttgcc 19320
gatctcgaca cactcac 19337

<210> SEQ ID NO 3
<211> LENGTH: 19336
<212> TYPE: DNA
<213> ORGANISM: Artificial Sequence
<220> FEATURE:
<223> OTHER INFORMATION: EHDV-TAU-LNCaP RNA consensus sequence
<220> FEATURE:
<221> NAME/KEY: Segment 1
<222> LOCATION: (1)..(3942)
<220> FEATURE:
<221> NAME/KEY: Segment 2
<222> LOCATION: (3943)..(6944)
<220> FEATURE:
<221> NAME/KEY: Segment 3
<222> LOCATION: (6945)..(9711)
<220> FEATURE:
<221> NAME/KEY: Segment 4
<222> LOCATION: (9712)..(11694)
<220> FEATURE:
<221> NAME/KEY: Segment 5
<222> LOCATION: (11695)..(13463)
<220> FEATURE:
<221> NAME/KEY: Segment 6
<222> LOCATION: (13464)..(15104)
<220> FEATURE:
<221> NAME/KEY: Segment 7
<222> LOCATION: (15105)..(16266)
<220> FEATURE:
<221> NAME/KEY: Segment 8
<222> LOCATION: (16267)..(17452)
<220> FEATURE:
<221> NAME/KEY: Segment 9
<222> LOCATION: (17453)..(18526)
<220> FEATURE:
<221> NAME/KEY: Segment 10
<222> LOCATION: (18527)..(19336)

<400> SEQUENCE: 3
gttaaaatgc aatggtcgca attaccgtgc aaggtgcaca gctcattaaa cgagtggttg 60
aaaggatata tcaaggaata acattcgaat tggataatgg catcacagaa ttttataaat 120
tttcagaaca tatcaggcgc ataagagaga aacacggagt gacatataag aggaaagcag 180
aggagataga gcacaacatt aaaatgagga aggaacaact gtttggattg cctgttttac 240
gtgattcaac ttgggaagaa atctttaata ttgactatag agatgatagt gttttacagg 300
tatacatgaa ttcagtgctg cgccaggaag aattgaatcc ggaggaagaa ttcctgcgaa 360
attataaggt gcaaggcgaa catgctgggt tgacgcaatt tattgagcaa agagcgaaga 420
acgaaatgca aatatatgga gacataccaa tcagagtttg ggccgccttt ctaattgaac 480
tggattcaga agttaaccac cagagtttag gggtgaaagt catgtcatcg ttcgtcaagc 540
gttatggaga gcctttccat cagggttttc gagatttatc aaacttagaa aggttcaacg 600
tatcatactc aacgccgctg ttgtttgaaa tgtgttgtat ggaatcaata ttagaacata 660
atattataat gcgcatgaag gaggagggag tacacaattt ggagtttggg gatgagaaaa 720
ttgatccaat agcactgttg cgcgaattgt ttattatatg tttgcctcac ccgaagaaaa 780
ttaataatat gttaagatcg ccatattcat ggttcgttaa attatggggg gtgggtgctg 840
accaagttac agtattgacg tcaggtgcag gcgacgatcg taattcgaaa gacgtttttt 900
atgacaaata tcaaacgaat acaaatcgtt acgtcaacat ttttaagtgt aaattctata 960

```
ctgaatcgca aaaatcgaat tcggagaagg ttgaagaggc gatcctatat tcgcaagaac   1020
tcggaatgca tcattatagc ttacccgtgt ttcaatcaat gttacgaaat gtatatacac   1080
ggccttttta tccatttaaa caaagtaact tgatgttggc atcttttttg ctaagcttac   1140
aggtaataac aggttatggg cgtgcgtggg tgaaaaacgt tggtacagat ttcgagaagc   1200
agatgaagcc aacgcctgga aatctaatag cggaagtgtc agaacgaacg cgtgaaaact   1260
ttattcaagc ttataatgag gcgagagaaa agagggaaga gatagtgaaa cctgaagatt   1320
tatacacctc tatgctgaga ttggctcgaa atacgagttc aggattcgct gcggagatat   1380
taatacagaa gagatttggt cccaacaaaa gaaaggaatt cgttaaaatt aactcaagaa   1440
tcaaagcggt tgtcattttt acgcgcgggc atatagtttt cacacccgca gagctggaga   1500
agaagtacga tactaccgaa ttgtatcaga ctaagggttc aagggacgtt ccaattaaag   1560
caacacggac gatttactcg ataaatttat cggtattagt tccacagtta atagttacat   1620
tgccattaaa cgaatatttt gcacgagttg gtggaaacac ttcacccgag tataaaaaat   1680
tgggcggtaa aataatagta ggagatctcg aggcgacggg atctcgcgta attgatgcag   1740
cagattgctt cagaaatagc ggtgacaagg atatactcgt tattgctatt gattatagtg   1800
aatacgacac gcatttaact cgctataatt ttcggaaggg catgttagaa ggtattcgtg   1860
aagcgatgaa acattataaa gatttgagat atgaaggcta cagcctggat caaataatcg   1920
acttcggata tggcgaagga cgtgttgcga aaacgctatg gaatggaaaa aggcatgtgt   1980
tcagaactac gttagataaa tatctgagtt tatcggaggc ggagagaata cagggagatt   2040
ttaaaacgcc taagggggta ttgcctgtta caacgataga cgttgcgaag aaaatcgaag   2100
ttagcgataa ttttaacaca ctggtatctg cgacggatgg aagtgacttg gcgttaatcg   2160
atactcactt atcgggcgaa aattcaacat tgatcgctaa ttctatgcat aataaggcta   2220
tcggcggttt aatacagagt gagctgcaaa aagagcacat gcatgatatc actttcctat   2280
cggaacaata tgtgggagat gatacgctat tctattgtaa acttcatact acggatagaa   2340
cgaaggtaca aaaaatgata acaacgattt ttgatacggt agcaaaatgt ggacatgaag   2400
cagcgccgag taaaacgatg ataacgccgt actcggtaga aaagacacaa acgcacgcga   2460
aacaaggtgt gtatgtacca caagatcgaa tgatgattat atcttctgaa cgacgcaaag   2520
acattgaaga tgtgcaaggg tacgttagat cacaggtgca aacaatggta acaaaagtga   2580
gtagaggttt ttgccatgat ttggcgcaaa tgattttaat gctgaaaacg acgtttattg   2640
gggcgtggaa gatgaaacgc actatcaagg aaggtggaac atatcgagat cgtaaattcg   2700
actcgaatga agaagacggg tttacgttag taatgttgaa aaacccactt gctctctatg   2760
tgccgatagg gtggaacggt tatggtgcgc atcccgcagc gataaatatc gtcatgacag   2820
aggagatgtt cttagactcg atgtgtattg ggaaactaga tgaaataatg gctcctattt   2880
taaaaattaa aggaaagatc cctcctgcat ggaatgagac gcaagcagac aaacgcgcaa   2940
ttggatctga aacaaagatg gcattcttct ccaaaatggc gcgacccgct gtacaaattg   3000
ctctgaacaa ccgtgaaata atggatgccg tagaacatct acctttagga gatttctcgc   3060
caggacgttt gtctagaaca atgatgcata gtgcgttgct aaaggaatct aaagctcgat   3120
ccttgctagc cgctggatat gaattagact accaaaaatc aattaacgta tggttagaag   3180
atcaagttac ggtagcaatg cgtgaagagc cgggagttat ttcgacgtcc tatgggaagc   3240
tattcgactt atattttgaa gaagatatta tagaggcgcc atacatgttt ccagaccaaa   3300
```

-continued

```
atttatcgcc tcaattctat atccagaaga tgaagattgg accacgttgt agttcgcgca   3360
tccgtacgtc ttatgttgat aagattgatg ttattttgcg caaggatgta gtaatgcgcg   3420
gatttataac cgctaataca attttgaacg taatagagaa gttgggcacg aatcatactg   3480
cgagtgattt aacgacggta ttcacgttga tgaatattga gaataaagta gcagaggagc   3540
tttcggagta tatcacaagt gagaaaatta ggttcgacgc cttaaagctt ttaaagaaag   3600
gaatcgcggg cgatgaattc actatgtcgc ttgatatagc cacgcaagtt atggttgata   3660
agtatattaa gtatccgcat cagctgacca aaacggagct ggacgcagta gtattatatt   3720
gttcgcaaat agtgatgttg agagcggcgt gcggactacc attgaagaga atgagattag   3780
ttgttttaga tgaggcaaaa cgacgtttca aagttagagc acagaggttt agaactcaca   3840
taccaagaat taaagtaatt aagaaactca tggatttgaa ccgtatgagt gttcgtcgtc   3900
tagaaaacca attcgtttag agcgcacccg cattacactt cagttaaatt gttcccagaa   3960
tggaggagat ttttataagc gtaattgata gcagtcagcg cgtaccgaaa cagttgtaca   4020
aagattatcc agtaattata gatgtcggac aacggaaagg tgaaaataga ttaccagtgg   4080
aacgattgga aggcaaaaac accatcgaac tgattcaggc agaagcgaga gatttatttc   4140
aatatgactc aaaagatgat tatgagataa tttttccaga tgcgttatca ataggcatac   4200
gtcgatatga ctggagacat aaagagttct caaggaatca aaatacaggc gatggtcgcg   4260
gattgatttc atcagatgat gcgtttgaag agttaatgcg tagctcaaat gcaaacgctc   4320
gagtaaaaac ggattttaat gaggagcata ttcatcacga attgtcatat tgtgacgttt   4380
atgtaaatgc gaccatagcg gaaactatag aaattagcgc tcataatagt gaaaagaagg   4440
attgttttca cggtgaagag acagcggtat ataatcatat gctaactgag gcgctatgca   4500
tcgggtcagg aacatgttat gatctggaag aacatgttca gctcaaaacg atcggggagg   4560
taggcttacg tccacgcgac catgttgatg tttcaggaag aactcatcca aagggagaaa   4620
agatgataac aaggagattc ggaggtggcg agataaagac gctgaccaca agtataaacc   4680
cagatcaatt cgacttaaag aagaagattt ttaatgagga gatcgctatc acggtagaaa   4740
aacgcgactt aattaaatat gatgatgaaa taatgcagct tgatgaaata gctgtaaaat   4800
ggattcggaa tcagaacgcc gatgacctgg aaaaaatcat attattgctg gaagcaatag   4860
gagaaaagga taaacgtgtc gaaccggcta atgcagaagg tatccgcaat aaattcaaaa   4920
ggaaattaca ggttaatctc cagaaaacgg atggtgaaat acgaagcata aggaattatc   4980
atcagcatgg tgaaccgaaa cggttggccg caatattaat attaacaatg tgcgacgtaa   5040
tgaaccgtgc catatgggga gataataggt ttaaactagt aagaggagtg tacaattatg   5100
ggaaatatag aatggggtcg gtttatcacg caatgcgaac agatatgatg tggcaactgc   5160
gatcaagtta tctagatacg tgtcctcgta tttgtgatag aagaaaatat ctaatgtacc   5220
gctataatta tttttcttta ggccgggaga cgggagattc tatatataaa tgggacatca   5280
ggactatgcg agacgacaag atgacaacaa gatcaaaggg atggcagtat ggagcaatag   5340
aggatgaaga ggaaagtgat gaagtgttaa tacatgattt tgatgaaggt aaatatgcag   5400
aatatatgca gcggataatt cagggaccat ggattgagaa agatggaatt gggattctaa   5460
tgaaagagca agcagcgatt gagctgtttg attttacgcg ggatgcttat gtagatgaag   5520
cgggtttcct gaggctgccc gcatattaca ataagctaat taaatcaact ttatatgaat   5580
cgtcttttaa ggtaagacgg gtagagatta cgcaaggtaa gagaccagat ccttggaccc   5640
aaaaaacgga ggatgaactg aagaaggaga acgagatgtg gcttttacct gtgtattcag   5700
```

-continued

```
ttgtggaccg agcgttctgt atgactggca atatattaag cactgcaaaa caggaacaaa   5760
gtgcacggtt tacagccata attgaggctt taaagaaaga gaagagagaa gtacgagaaa   5820
gatattcacg taatgatagt tacacttgcc caatgttaaa cgtatttaat tatacaggat   5880
ataggcagcg aaggttcgtt ttttcaatat taaaaaatca cctgccaaaa aatctactca   5940
tagacatgta cccagatgag gacatagaat acgatcctcg cgattataca gactgtatgg   6000
gaaaagaaga gattttgatg aatatgaaat cgatatttga ggtaatactt tatctaattc   6060
aaataggctt cgaaaaagag gtcgtagttc tgagcgaaga ggagatccgt gtggtgaaac   6120
atagaatgat aaagagagag caccgaaacg acatcatgag tacgcttttg ccggaatttt   6180
cgcggattat aaggagaggc gagaaaatgc aagaggtgga gaagaatgag gacctattac   6240
caatgtattt ctatcaatca ctcattttat caaacgaatt gatatatgaa aacgcgaata   6300
aatcgcatcc agttcttatg ttttgtgaaa aaagagtaag gatcgtccct attcagacga   6360
acgtttggcg aaaagatgtg cctctgcttt cttttctttt tgttttgaaa tatcatgcag   6420
gatggcgaag acgaggtgaa actattgaag aggacgttcg aacagtatgg ccacatttaa   6480
cgaagtattg gttaaatatc gaattcccac gcagggagat caccgattta acgttgatga   6540
gaatgcatcc attgaatacg cattttagca catattgctc gcgtatgtct gaggtatata   6600
gttttgcgtt acctatagta catccatcaa aaggtatcgt agttataggt atcattccgg   6660
atactatctc gaatgcccaa ggtttctcgg ttattaaaca aagatttcat tctgttgaac   6720
agtatgtaca tgcgcgaata attttaagag tgttggagaa tggtcacgtg agtgtctacg   6780
gcgatgggga cgtcaagtgt aatttattag agaagttttg ttgcggaagg aagtcgaaga   6840
tcgtaagagt taaactaaat ggaaaagtat acgcgaatcc agaaataatc tcaaaattaa   6900
tgaattaaac ccctgaccgg gtttactggg aacaacaaac tacggttaaa tttccagagc   6960
gatggcggaa ccaccagatg cggtgcggct aaaacaagtc catatttaaa gggagatgaa   7020
ttgtcgagcg acagtggccc attactttca atattcgctt tacaagaaat aatgcaaaaa   7080
gtccgacagg cgcaatccga atatgtagca gcgacaaaag atgtcgacct aacaatacct   7140
gatgttcaaa agataatcga tggagtgaaa gagttagctt cagaaacaat ctataaagtt   7200
gtaaacaaac cactgatatc gtatcgacat atcgtgatgc aatccagaga tagattttta   7260
cgggttgata cttattatga aagaatgtca gaagttggtg acaagataga tgaaaatgaa   7320
ccggctaaat tttatgaaac cgtcatcaag aaagttaggc atttaaggac tgaaggcgct   7380
tttgttttac acaatatacc aactagagat catagaggta tggagatagc ggacccagaa   7440
attcttggtg ttgatgttaa gagtatattg cctgttttga ctgcggagca tcgtgctatg   7500
gtgcagcata tattagacgg agcaatcata gaaaacggta acgttgcgac gcgtgatgtc   7560
gatgtatatt taggcgcttg ttcagagtct gtatatcgca tatacaatcg gcttcaggga   7620
tatgttgagg cggtacaatt agaggagttg cgggcggcga tcacgtggct tgaaagactg   7680
gggagacgta aacgtatgac cttttcgcag gagtttctca cagactttag acgagcggat   7740
acgatatggg tattagcatt acagttgcca gcaaatcccc gtgtaatttg ggatgtacct   7800
agatgttcaa tagcaaacct aattatgaat atagcgacgt gcttaccaac aggagaatat   7860
gtatctccaa atccgcgaat tgcatcaata acgcttaccc agagaataac aacgactggc   7920
ccttttgcta tcttaactgg atcaactcca actgctcaac aattagatga tgtgaggaag   7980
atatatttag cgttaatgtt cccaggtcaa ataatcttag atttaaaaat agatccgggt   8040
```

-continued gagaggatgg acccagcggt acgtatggtg gcgggggttg ttggtcattt aatgtttaca 8100
gcgggaccta ggtttacgaa cataacccaa aatatggcac gacagcttga tattgcctta 8160
gctgattttc ttctctacat gtacaacacg aggatccagg ttcaatatgg tccaacggga 8220
gaaccgctag atttccgaat aggacgtggg cagtatgatt gtaacgcttt tcgcaccaat 8280
ttccaaactg gtgcgggata taatggatgg ggattagtag atgttgaaaa tagagaacca 8340
gcaccatatg atcatgtaca acgctttata cgatattgta acattgattc cagagaactg 8400
atacacccag cgacgttcgg tattggtatg aattattatt gttataacga aatgttaaga 8460
atgctagttg ctgcaggaaa ggatacggag gcggccttct ttaggaacat gttaccattt 8520
cacatggtta gattcgcgcg tataaatcag ataatcaacg aggacctaca ttcggcgttt 8580
tcgatgcctg atgatcaatt taatgtatta ttagctaata tgatcgcagg cgcgcaagaa 8640
aggatggacc ctgtggtatt ggatattagt tggatttcta tttggtacgc gttcaatcga 8700
tcttttgaac caacgcgcag aaatgagatg ttagaaagtg cgccgctaat tgagtctgtt 8760
tatgcgtcag aattgactgt tatgaaaact gatatgcagc agatggcgtt gttacagcgt 8820
cgcttccccg atgtgttagt tgaagcgagg ccaacgcatt tttggaaagc ggtaatggag 8880
gtatctccgg aaccggtacg tgcaatcatg gatctagcgc attcgcacag tttcataaat 8940
attcgagata tgatgcgatg gatcggttta ccttcaatgc agaactcgat gaagttggtt 9000
ttagaagaag aggcgtgggc ggtggctaat gatttcgaag aattgatgtt aacggatcaa 9060
gtgtacatgt tccgcgatat gctacctgaa ccaaggttag atgatattga aaggttcaga 9120
caagaagggt tttattacac aaatatgcta gatggtcctc cagctatcga tcgagtagtg 9180
cagtatacat atgaagtagc aaggttacaa gcaaatatgg gtcaattacg ggcggcttta 9240
cgaagaatta tggatgacga aggttgggtt aggttcggag gtgtattaag aaccgttcga 9300
gttaagtttt tcgattcgcg gccccctgag gagatactac aagcgctgcc gtttgattat 9360
cagacgagtg agaaaggtgg gctaacctat gctacgatta aatatgctaa tgacacgacg 9420
atatactacc tgatatacaa cgtagaatac tcgaatcttc cggattcgtt ggtactaatt 9480
aatccaacct acgttatgac caaggttttc ataaataagc gaatagttga aagagtacgg 9540
gtgggacaag cattagcggt tatgaataag cgtttcattg cttataaagg gaagatgcgt 9600
atcatggata ttacgcaagc gcttaaggtg ggcaccaagc tagcagctcc gaccgtgtaa 9660
atatctgcga ccaatatttg caccgaggaa aagcactgga aatacaccta cgttaaaaca 9720
tgccggagcc acatgcagtg atctatgtta cggaggaatt ggtgcacctc atcaaggaaa 9780
gctatttacc gatttgggag atacggggcg atgaaactct aaatgaacta tggctaacaa 9840
acggaaaata ttcatcagat gtatacgcgt atgggaaaat taataagtgg agttatcgcc 9900
aactacgtgg acatggaatg atattcgtaa gtactaagaa aatgattcag ttaaatgatg 9960
tattaatgtc cgtggatgtc aggataccgc gtgaagtgac aaagaacata gacgtcaaag 10020
cattcgaatc gattgttggg cgcaggagat taaaattaag gaaggcgttt ggcgacattc 10080
tacgcagcta cgcatatagg aaagcgattg tattacatgg aagtgaagcg gagactctaa 10140
ataatgcaaa cccgcgattg cacaaagttt atgggctacc gaaacagcca ccattgtatt 10200
atgagagatt aaatgcggat gggccattta tggacgaatc tactgacgag aaattagttt 10260
cgatgcttga ttacgccatc tatagctgtg aagaagtaca ttatgtagga agcggggatg 10320
gccgtacgtt aatgaatttt gcgaaacgat caccagagcg tttccatcga atcatatggc 10380
acttatatga tccgatcgct aacgatatga aatacaataa catatatgtt catcgtacct 10440

```
ttgttaacaa caagcatgat gtaatgaaga atgtaaatct attaaagcga gtggagaggc  10500
tgtttatttg ggatgtttca agcgatcgtg gtgacatgga tgacagacag tgggaaaaac  10560
atagatttgc agaggataga atgggggaag agatagcgat gtccatgtca gggttgttct  10620
cgatggctat aatcaaacat cgcatacctc agtttatgga tcaatatcac gttgtatcta  10680
catacctaat accacaacca ggagcgccta cagatatgta tgaattacgg aatattatga  10740
ttttgagagg ttatagttat gttgaccgaa cacgacatac tgatgcacag gtacacacag  10800
tggtacaaag ggatgcgtgt aaattagtcg agtggtatca tggacgtgaa aaaggtaaga  10860
agttgaagaa aatgattttc gaattcttac atatagtccg cgagaacgga ttgtacgcag  10920
aaagtgaaga accgcgagcg gacttattct atttgacaaa taaatgcaat tatgatatgt  10980
ggagagagca gaagcgagtt ttacggacaa gtcaaattgc tacaatgtgg gtgggaggtg  11040
atcaattgtt tgattatgat gactattcgg cgcctcgtgc gttgcttatg ctagaatgct  11100
cgtatcccga tgtacgtata ttagatggga atggagcggt tctgttttta atatggagat  11160
atccagatat ttacaaaaga ggcttaaatt atgatcccag ctgggctatg aaatttgcgg  11220
ttacgttaaa ggaaccagtc cccgatccgc ctgttcctga tatatcactg tgccggttca  11280
tcggactgcg agtcgaatcc tccttaatga gaatacagaa tccgagagtt catcaggtta  11340
acgatgagtt aaagcgaatg ggattagatg tgtcgggaca tctgtatgtc acgttgctga  11400
gtggatcata tgtcacggat ctattgtggt ggtttaaaat gatattagag tggtcatcat  11460
taaacaaaaa tgagaagctg gatcaactta agacatcgaa ggctgaagta atcgaatgga  11520
aggatgagat ggcagaacgg ccatggcatg ttcgaaatga tctgatagcg gcgctacgag  11580
aattcaaata taagattcat aaacgatggg atgcacccat tgagtcgtgg ctagatttat  11640
tgcagcgtct atagaatgtg gtagttctgg actaggcctg catgttacac ctacgttaaa  11700
aagttcttcg tcgactgcca tcgagatgga gcgcttcttg agaagataca acatgaacag  11760
ttattatgcc aatcatgtca aaatgtttaa agctttatcg ccccagtgga catgctcgca  11820
tttgagacgg aattgtttat ttgatggagt atgtgccaaa cagcactttg aggaagtgat  11880
gaatcgtata actgagagga atgatccaca tgccgcttat aggttagcag aaatggctca  11940
taatacaatg ctggacagag agaaagtgtg gctgcagtgc tataaaagct tttcagaacc  12000
atatgaagaa aacatagcag agaagattca aatatgcggc cgagaacttt tagacaaata  12060
caaaaatagc gatatggtta caaaaattga caacatgatt aaatatgacc caacacgtat  12120
tgtactagat gataattttt cggcttttcc atatctatac attccagtca attacggcca  12180
aatgattcag ccaattagaa taatgaggtt tagacaaatt ggatattgct tttatcagcc  12240
agatgcagca gatgactggg ttgctccaga catatatcct atgcggagac ctagaatgga  12300
aatatgccgt cgagtgatgg aagcggttgg aacgtgcggc tttacaggat tcagtggacc  12360
ggtgtttcaa attatgttcc taccaataca gatgctgcca tacatggaaa atgaaggatt  12420
tgccaggata ataaataggt atgcccaaat ggcagttcag caatatctac gagttggata  12480
catcgaggaa cgtcggtatg tgactcagtt gtttggagat tgtccagcgg gagagttccc  12540
tatgcacagt atgatgctca ggagatggga gaggaatggg agatcacaaa cactggttca  12600
gatgcggcac actatcgctg gaaacaagga gtggcaaaca tggttgttac caatgatcct  12660
ggtgaggatt gccgtaagag aaccagcaaa ttttgaatat gtcagaggat ttgtacaggg  12720
cagacacaaa tgtcaactgt gcttcctgaa aaacggttgt gatcgtcaga ctttttatca  12780
```

-continued

```
tatagatgtg aggacatcag agatggtggg ttgtagtaca gtgacagaag taatgatcga  12840
tgaacatgtc gacgcgtcat taccagtgca aaagatcaaa cttaccgggg cagagcattt  12900
aggtcgagca agtgatcatt atttcaagta taatgctaca acagggatgg aagcgctgat  12960
tcgcaccgca atacagatcc atcgatgggt gagagggact ggagtgtggg aaggtgatga  13020
atggcaggaa ggggtttatc tgctggctag ggtattacta cgttgggaat tatcatcgca  13080
ggctcgatct atcatgttca gactttttttg ctttgtctgt tttggatatg cgccgcgaaa  13140
agatggaacg ataccagatt ggaaagattt gggaacattt ttggatacgg tcctgaacgg  13200
aacggagctg gctgatgatg aagatgaaac agtgactggc attatgtttg agctgagccg  13260
atgcgttatg acgctcgcat atgccgagaa agcgaaagtc gtaactttta atgttccaga  13320
atgtgatgaa ggcgcggtta tgaacatcgc acaggcgatg gccaacatgt gggataactg  13380
aaaatgacac ttctttaaat tacttatcca aattcaaaat ttcctgagat tcaattggct  13440
ctccattcga actttacact tacgttaaaa tggaggcacg ttcttgcatc atgggcaaga  13500
ttatcaagaa attgagcaag gtaggcaaaa agattggaga tgcgttaaca tcgaatactg  13560
cgcaacgtat ttataaaaca ataggaaaag cagcggaacg ttttgcggag agtgaaatcg  13620
gttcggccgc gattgatgga ttgattcaag gcacagtaca atctgtgatc acgggggagt  13680
cttatggtga aactgtcaaa caagcggtat tattaaatgt gttgggagcg ggagattcaa  13740
ttccagatcc tttaagtcca ggagagcgag gtatgcaagt taaaatccaa gagttagaag  13800
atgaggagaa aggaaacgcg atacggcaac ggcataatga cagaattata gaactattta  13860
gtaatgattt agatgatgtg tatcggttcg caacggcgca aatcgcagac gatgagttga  13920
aagatgatca gtatgaaatt ttagagaaag ctgtgaagtc ttatggcaaa gtgattggag  13980
aagaggaacg aagattgaaa cagctcagag atgcattaca gaaagagatt tcagatagga  14040
gtaaaattga gagagagatg gttgttgaat atcgtaacaa gattgaagcg ttacgagggg  14100
cgatagaaat tgagtcagaa ggtatgcagg aagaagcgat acaggagatt gcaagtatga  14160
gtgctgacat attagaagca gcgtcagaag aagttccctt cttcggagca ggcatggcga  14220
ccgctatagc ttcggcaagg gcggttgaag gcggctataa actgaagaaa gtgataaacg  14280
cactgagtgg aatcgatttg agtcacctga ggactcctag aattgaacct caaacgctgg  14340
aagtgatcct acggacacca gccggtgcag agattgatga tactaaacta gttacaggta  14400
tagcggcgaa gatcgaggct atagaagata atcatcatga agttgaacat attgagaagc  14460
agatattacc acaaatcaaa caagctatga aagaggatca cgaagctata ggaagtgagg  14520
agaccaagag gattcttcct aaaactgcta tgcgatttaa agtgccatta agccagcagc  14580
cacaaattca tatttacgct gcaccttggg attcagacga cgtgttcata ttgcattgtg  14640
ttgcaccaca tcatgcgaat gaatcgttct ttatgggatt tgatctggag ttggagtatg  14700
tattttacga agatttgaca cgtcattggc atgcgctcgg tggtgcacag gaggcgacag  14760
gcaggacgtt tcgagaagtt tatcgtgaat tcttctcatt ggctctacag caagaaggtg  14820
cgagcgtcat acatcaacgc agattagcgc gttcacgagg tgcgcacccg atttatttag  14880
gagcgacgca ctacgaagta tcatattctc agttgaaacg aaatgcacta aaactagtga  14940
acgattctga actgcaggtg catgtgttac gaggtccgaa acatttccaa agacgtgcaa  15000
taatgggtgc gattaaggta ggcctaagct taattcgaga gattgacttg cccgagttta  15060
tgcgttacgc gtgaaggcgg agtacgcgaa ctccttacac ttacgttaaa atttggtgaa  15120
aatggacacg attgcagcaa gagctctgac agtcataaaa gcttgtaata ctttgaaaga  15180
```

-continued

```
agttagaata gtagtagaat ccaatgtgtt ggaaattctt ggaatagcta ttaacagata  15240
taatgggcta actttgagat cagtaaccat gcggccaaca tcacaggaac aacgaaatga  15300
aatgttcttt atgtgcttag atatgacgct ggctgcggcg aatttgaata tcggaaacat  15360
atctccagac tacatacaaa atttagcaac aattggggtt ttagcgacac ctgaaatacc  15420
ttatacaatg gaatcagcga atgagattgc gaggatgagt ggagagacag gaacgtgggg  15480
accagatcgc caaccgttcg gctacttctt aacggcagct gaagttacgc aacatggacg  15540
atttaggcaa cgcgcgggac aaaatatcac aaccacggtt gtttcgtcaa ctttggcgca  15600
ggtttcaatg aatgcaggag cgcgtggaga tatccaagcg ctctttcaga atcagaatga  15660
cccaattatg atttattttg tttggagaag aatagggaca ttttcaagcg cggcgggaaa  15720
cgcacaggag acaccacaag gagtaacatt aaatgtggga ggtgtgaata tgagggcagg  15780
agtgatcgtg gcttatgacg gtcaagctcc cgtgaatgta aacaatccgg gagcgggacc  15840
aggtatgata gaaatagaag taatctacta tttgagttta gataaaacaa tgacccagta  15900
tccctcatta caggcacaga tttttaacgt ctattcatat aaaaatccgt tatggcacgg  15960
tctgcgggcg gcaatactca acagaacaac attaccgaat aatatcccac caatatatcc  16020
acctaatgat cgtgaaaatg tcttattgct gatactactt tcagctctag cagatgcttt  16080
tagcgtactg gcaccagatt ttaatctatt cggcgtcgta ccgatacaag gtccaataaa  16140
cagagctgtt gctcaaaacg cctatgtgtg agggctgtta tggcacggca taacgctcac  16200
atacgcccgt gtcattgtcg tggataacgg gtcatccatt tgcacgtttt cccaaattca  16260
acttacgtta aagattccct gtgcaatgga gcaaaagcaa aggagattta caaagaacgt  16320
attcgttcta gatcaaaagc gaaaaacaat atgtggtcaa attgcatcaa agaatgctca  16380
accttattgt caaatcaaaa ttggaagaaa tttcgcatta aaagcggtgc caacaccgga  16440
accaaagggg tacgttttag agattagtga agttggttcg tatcgcattc aggatggcag  16500
tgatattatt agtctgatga tatcggcgga cggagttgaa gcaacgacag agcgatggga  16560
agaatggaaa tttgagacga tctcgtgtgt tccaatggct accgtattga atattaatgg  16620
tgctctaatt gatgcggaga ttaaaatatc gaaggggatg ggcatggtac caccgtacac  16680
aaggaatgat tttgacagac gggagatgcc ggaattacct ggcgttcaaa agtcaaaata  16740
tgatgtaaaa gaattacgcc aaaaaatcag agaagaacgt gaaaagggaa atgttgaatt  16800
acagcctaag ccaacgttta aagcggaacg ttggcatgaa cagcccgatt ccgatgagga  16860
tcaaaatcca atgaatcaga tggcagatga ttgggcagag gaggttcgaa aacaagatga  16920
ggacgctgcg cgccgtaaag cgttagaaac taaattggag gaacagagac gaagatatga  16980
ggcatttaag atggagaata gaaggcaaca ggaggaattt aagaaaacgt cagaggaacc  17040
aaaagaaatg agagatcgga agaaggagcc acagctagaa gaggttattg tcgaagatga  17100
aggagaagaa tctggtgagg aagagaccgt tagcgcatcg tacattacgt ctaactatat  17160
agagcgcata agtaaaattc gaaaatcaaa agatgaacga ttgtcaatgc tcgcgagtat  17220
gatgccgcaa caggcgggtg aatttacatc gatgctattc accaagaaaa ttaaatggga  17280
taatgttccg ttgtatttaa tagacgaggt tcagaagaaa tatgagttac agagcgtagg  17340
gggttgtgat cgtgttgcct ttgtctccaa aggcacgaac ctaatcattt taccggtagg  17400
cgtctaatcc acgctgatgt agccgcggat aggggaaggg atttacactt acgttaaaaa  17460
ttgcgcatgt cagctgcggt tttgctcgca cccggtgacg tgatccaatg ttcggccgag  17520
```

-continued

```
gaactaaaac aaagacagat ccagattcat ttagttgatt gggataaggg agattcaaag  17580
gaccaaaaac aaacagaaca atcagcggat aaactagatt cacagaagca gaatgagaag  17640
gagacacaga aagggagcaa aaaggaagag acagatgaga aagatgcaaa tgaagatgat  17700
gttcgacgct tggatgctac agtgggacat cgaccaagcg ataaacgatc tggagaacgc  17760
cagaagggat ctagcgacgg aggaggaagt gagactaaga gaggagatag agatgatgcg  17820
tcaggaactg gaagcaatgg ggccgataga gggagatgga tagtgggaag cgaagaaatt  17880
gctcaatgtc tccagaatcg gtacggagtg agcatccctg tatacagagc aggagcgacc  17940
ggtacgttca taaacattga gaagtcgctc cagaaggagc tgggtttcac acgtgaaatg  18000
atggcggaac agacggaagc gctgcgagct gtgaaggctg agatgaagaa gaataaaaac  18060
gagaaatcta aggacgcacc agcaacgcag aaccccagtt cagagaggaa ggggaaaggt  18120
aagaaagatg ataaagaaga agggatagag acagacgagg ggatggttga ggtctcatcc  18180
tcaaaacaaa cgttaagact ggctgttgaa gatgttatga gccagaagaa attactatct  18240
atgatagggg gaggtgaaag acgtgaggag gccacacgtg cgcgggagac ttcggttatg  18300
ttagtttcta actcgaaaga tgatgttgaa cgcgctacag catattttac agctccaacg  18360
ggggatacta actggaaaga agttgcacgg cttgccgcta aaagatcaaa tatcatggct  18420
tacacttcaa cggaagagga tgttaagaag agcttcttgc acttgattga tcatctctaa  18480
agggtccggg ctgctgcttc atggcacacg cgcgatttaa acttacgtta aaaagagatc  18540
ggtaccatgc tatccagatt agtatcgggt acggagacaa gaataaacat gaaacaaagt  18600
gatgagatga gtttaatgcc atatcaagag aatgtaaggc caccaagtta tgtaccaaca  18660
gcgcccacgc caacatcaat gccaagggtt gcattggata tactcgacaa ggcaatgtca  18720
aatcaaacgg gtgcaactat ggcgcaaaaa gtagagaagg ttgcgtatgc gtcatacgca  18780
gaggcgttta gagatgatct acggttgcga cagataaaga aacgtgtgaa tgagcaggtg  18840
ttgccaaaaa tgcgcgtgga gctaacaatg atgaaaagaa aacgtgcaat ggcacatatg  18900
atattgatta tcgctgcgat tgttgcccta ataacctccg cgagcacact aacgagcgat  18960
ttaggaatca ttctaaagaa tactaccgca acggaaataa tacagaaaca gatcaaacca  19020
ttttgcgctg cttttggcat aataaattta gccgcaacga tgattatgat gtttatggcg  19080
aagaacgaaa aagtaataag ccagcggatt gaccatacaa gaaaggagat aatgaagaaa  19140
gatgcataca atgaggcggt gaggatgagt ataacggagc ttagtgaagt acctttagat  19200
ggatttgaca taccgcctga actgatcaga tagagtggtg cccccaggtt accgtgatgt  19260
gagattggca ggtctcgaca tggtgactcc tactgttgta tagcggggga gggtttgccg  19320
atctcgacac actacc                                                  19336
```

```
<210> SEQ ID NO 4
<211> LENGTH: 20
<212> TYPE: DNA
<213> ORGANISM: Artificial Sequence
<220> FEATURE:
<223> OTHER INFORMATION: JAK1-exon5 forward cloning primer

<400> SEQUENCE: 4

ttcattttcc tgccttccag                                                20
```

```
<210> SEQ ID NO 5
<211> LENGTH: 20
<212> TYPE: DNA
<213> ORGANISM: Artificial Sequence
```

-continued

<220> FEATURE:
<223> OTHER INFORMATION: JAK1-exon5 reverse cloning primer

<400> SEQUENCE: 5
ccacaaactc cagcttctcc 20

<210> SEQ ID NO 6
<211> LENGTH: 20
<212> TYPE: DNA
<213> ORGANISM: Artificial Sequence
<220> FEATURE:
<223> OTHER INFORMATION: JAK1-exon9 forward cloning primer

<400> SEQUENCE: 6
ctgaagctct cttcccacga 20

<210> SEQ ID NO 7
<211> LENGTH: 20
<212> TYPE: DNA
<213> ORGANISM: Artificial Sequence
<220> FEATURE:
<223> OTHER INFORMATION: JAK1-exon9 reverse cloning primer

<400> SEQUENCE: 7
ctaaaacacg ggctctctgc 20

<210> SEQ ID NO 8
<211> LENGTH: 20
<212> TYPE: DNA
<213> ORGANISM: Artificial Sequence
<220> FEATURE:
<223> OTHER INFORMATION: JAK1-exon5 to exon9 forward cloning primer

<400> SEQUENCE: 8
tccaaatcgc accatcaccg 20

<210> SEQ ID NO 9
<211> LENGTH: 21
<212> TYPE: DNA
<213> ORGANISM: Artificial Sequence
<220> FEATURE:
<223> OTHER INFORMATION: JAK1-exon5 to exon9 reverse cloning primer

<400> SEQUENCE: 9
ggtgcagctc cacctcagca c 21

<210> SEQ ID NO 10
<211> LENGTH: 42
<212> TYPE: DNA
<213> ORGANISM: Artificial Sequence
<220> FEATURE:
<223> OTHER INFORMATION: JAK1 forward cloning primer

<400> SEQUENCE: 10
ctcgtacgct taattaacga tgcagtatct aaatataaaa ga 42

<210> SEQ ID NO 11
<211> LENGTH: 42
<212> TYPE: DNA
<213> ORGANISM: Artificial Sequence
<220> FEATURE:
<223> OTHER INFORMATION: JAK1 reverse cloning primer

<400> SEQUENCE: 11
gaggggcgga attccggatc ttattttaaa agtgcttcaa at 42

<210> SEQ ID NO 12
<211> LENGTH: 23
<212> TYPE: DNA
<213> ORGANISM: Artificial Sequence
<220> FEATURE:
<223> OTHER INFORMATION: pJET1.2 vector forward sequencing primer

<400> SEQUENCE: 12
cgactcacta tagggagagc ggc 23

<210> SEQ ID NO 13
<211> LENGTH: 24
<212> TYPE: DNA
<213> ORGANISM: Artificial Sequence
<220> FEATURE:
<223> OTHER INFORMATION: pJET1.2 vector reverse sequencing primer

<400> SEQUENCE: 13
aagaacatcg attttccatg gcag 24

<210> SEQ ID NO 14
<211> LENGTH: 17
<212> TYPE: DNA
<213> ORGANISM: Artificial Sequence
<220> FEATURE:
<223> OTHER INFORMATION: JAK1 forward qPCR primer

<400> SEQUENCE: 14
ggaagtgcgc ttctctg 17

<210> SEQ ID NO 15
<211> LENGTH: 20
<212> TYPE: DNA
<213> ORGANISM: Artificial Sequence
<220> FEATURE:
<223> OTHER INFORMATION: JAK1 reverse qPCR primer

<400> SEQUENCE: 15
ctgcatttat tcagctgtcc 20

<210> SEQ ID NO 16
<211> LENGTH: 19
<212> TYPE: DNA
<213> ORGANISM: Artificial Sequence
<220> FEATURE:
<223> OTHER INFORMATION: STAT1 forward qPCR primer

<400> SEQUENCE: 16
ttcagaccac agacaacct 19

<210> SEQ ID NO 17
<211> LENGTH: 21
<212> TYPE: DNA
<213> ORGANISM: Artificial Sequence
<220> FEATURE:
<223> OTHER INFORMATION: STAT1 reverse qPCR primer

<400> SEQUENCE: 17
ctgtgttcat catactgtcg a 21

<210> SEQ ID NO 18
<211> LENGTH: 23
<212> TYPE: DNA
<213> ORGANISM: Artificial Sequence
<220> FEATURE:
<223> OTHER INFORMATION: IFIT5 forward qPCR primer

<400> SEQUENCE: 18
gcactttaaa caagctcctc cta 23

<210> SEQ ID NO 19
<211> LENGTH: 21
<212> TYPE: DNA
<213> ORGANISM: Artificial Sequence
<220> FEATURE:
<223> OTHER INFORMATION: IFIT5 reverse qPCR primer

<400> SEQUENCE: 19
ccaagtttga ggaacaatgc t 21

<210> SEQ ID NO 20
<211> LENGTH: 19
<212> TYPE: DNA
<213> ORGANISM: Artificial Sequence
<220> FEATURE:
<223> OTHER INFORMATION: IRF7 forward qPCR primer

<400> SEQUENCE: 20
cccagcaggt agcattccc 19

<210> SEQ ID NO 21
<211> LENGTH: 20
<212> TYPE: DNA
<213> ORGANISM: Artificial Sequence
<220> FEATURE:
<223> OTHER INFORMATION: IRF7 reverse qPCR primer

<400> SEQUENCE: 21
gcagcagttc ctccgtgtag 20

<210> SEQ ID NO 22
<211> LENGTH: 20
<212> TYPE: DNA
<213> ORGANISM: Artificial Sequence
<220> FEATURE:
<223> OTHER INFORMATION: SOCS3 forward qPCR primer

<400> SEQUENCE: 22
ggagacttcg attcgggacc 20

<210> SEQ ID NO 23
<211> LENGTH: 20
<212> TYPE: DNA
<213> ORGANISM: Artificial Sequence
<220> FEATURE:
<223> OTHER INFORMATION: SOCS3 reverse qPCR primer

<400> SEQUENCE: 23
gaaacttgct gtgggtgacc 20

<210> SEQ ID NO 24
<211> LENGTH: 20
<212> TYPE: DNA
<213> ORGANISM: Artificial Sequence
<220> FEATURE:
<223> OTHER INFORMATION: p21 forward qPCR primer

<400> SEQUENCE: 24
ctgcccaagc tctaccttcc 20

<210> SEQ ID NO 25

```
<211> LENGTH: 20
<212> TYPE: DNA
<213> ORGANISM: Artificial Sequence
<220> FEATURE:
<223> OTHER INFORMATION: p21 reverse qPCR primer

<400> SEQUENCE: 25

caggtccaca tggtcttcct                                                   20


<210> SEQ ID NO 26
<211> LENGTH: 20
<212> TYPE: DNA
<213> ORGANISM: Artificial Sequence
<220> FEATURE:
<223> OTHER INFORMATION: IRF9 forward qPCR primer

<400> SEQUENCE: 26

tcctccagag ccagactact                                                   20


<210> SEQ ID NO 27
<211> LENGTH: 20
<212> TYPE: DNA
<213> ORGANISM: Artificial Sequence
<220> FEATURE:
<223> OTHER INFORMATION: IRF9 reverse qPCR primer

<400> SEQUENCE: 27

caatccaggc tttgcacctg                                                   20


<210> SEQ ID NO 28
<211> LENGTH: 20
<212> TYPE: DNA
<213> ORGANISM: Artificial Sequence
<220> FEATURE:
<223> OTHER INFORMATION: RIG-I forward qPCR primer

<400> SEQUENCE: 28

gaccctggac cctacctaca                                                   20


<210> SEQ ID NO 29
<211> LENGTH: 20
<212> TYPE: DNA
<213> ORGANISM: Artificial Sequence
<220> FEATURE:
<223> OTHER INFORMATION: RIG-I reverse qPCR primer

<400> SEQUENCE: 29

ctccattggg cccttgttgt                                                   20


<210> SEQ ID NO 30
<211> LENGTH: 20
<212> TYPE: DNA
<213> ORGANISM: Artificial Sequence
<220> FEATURE:
<223> OTHER INFORMATION: MX1 forward qPCR primer

<400> SEQUENCE: 30

atcagcctgc tgacattggg                                                   20


<210> SEQ ID NO 31
<211> LENGTH: 20
<212> TYPE: DNA
<213> ORGANISM: Artificial Sequence
<220> FEATURE:
<223> OTHER INFORMATION: MX1 reverse qPCR primer

<400> SEQUENCE: 31
```

-continued ccacattact ggggaccacc 20

<210> SEQ ID NO 32
<211> LENGTH: 20
<212> TYPE: DNA
<213> ORGANISM: Artificial Sequence
<220> FEATURE:
<223> OTHER INFORMATION: DUSP5 forward qPCR primer

<400> SEQUENCE: 32
ggatccctgt ggaagacagc 20

<210> SEQ ID NO 33
<211> LENGTH: 20
<212> TYPE: DNA
<213> ORGANISM: Artificial Sequence
<220> FEATURE:
<223> OTHER INFORMATION: DUSP5 reverse qPCR primer

<400> SEQUENCE: 33
caggaccttg cctccctttt 20

<210> SEQ ID NO 34
<211> LENGTH: 19
<212> TYPE: DNA
<213> ORGANISM: Artificial Sequence
<220> FEATURE:
<223> OTHER INFORMATION: GAPDH forward qPCR primer

<400> SEQUENCE: 34
agccacatcg ctcagacac 19

<210> SEQ ID NO 35
<211> LENGTH: 19
<212> TYPE: DNA
<213> ORGANISM: Artificial Sequence
<220> FEATURE:
<223> OTHER INFORMATION: GAPDH reverse qPCR primer

<400> SEQUENCE: 35
gcccaatacg accaaatcc 19

<210> SEQ ID NO 36
<211> LENGTH: 20
<212> TYPE: DNA
<213> ORGANISM: Artificial Sequence
<220> FEATURE:
<223> OTHER INFORMATION: STAT1-targeting small guide RNA (sgRNA)

<400> SEQUENCE: 36
gaggtcatga aaacggatgg 20

<210> SEQ ID NO 37
<211> LENGTH: 20
<212> TYPE: DNA
<213> ORGANISM: Artificial Sequence
<220> FEATURE:
<223> OTHER INFORMATION: STAT3-targeting small guide RNA (sgRNA)

<400> SEQUENCE: 37
gcagcttgac acacggtacc 20

<210> SEQ ID NO 38
<211> LENGTH: 20
<212> TYPE: DNA

-continued

```
<213> ORGANISM: Artificial Sequence
<220> FEATURE:
<223> OTHER INFORMATION: GFP-targeting small guide RNA (sgRNA)

<400> SEQUENCE: 38

gggcgaggag ctgttcaccg                                                   20
```